(12) United States Patent
Ansell et al.

(10) Patent No.: US 12,237,080 B2
(45) Date of Patent: Feb. 25, 2025

(54) METHODS AND APPARATUSES FOR ESTIMATING BLADDER STATUS

(71) Applicant: University of Central Lancashire, Preston (GB)

(72) Inventors: Darren William Ansell, Lancashire (GB); Caroline Sanders, Prince George (CA); Peter Leather, Liverpool (GB); Mahdi Amina, Preston (GB); Kaya Kuru, Preston (GB)

(73) Assignee: University of Central Lancashire, Preston (GB)

( * ) Notice: Subject to any disclaimer, the term of this patent is extended or adjusted under 35 U.S.C. 154(b) by 0 days.

(21) Appl. No.: 17/875,004

(22) Filed: Jul. 27, 2022

(65) Prior Publication Data
US 2023/0162853 A1   May 25, 2023

Related U.S. Application Data

(63) Continuation of application No. 15/747,696, filed as application No. PCT/GB2016/052271 on Jul. 25, 2016, now Pat. No. 11,482,327.

(30) Foreign Application Priority Data

Jul. 27, 2015   (GB) .................................. 1513208

(51) Int. Cl.
*A61B 5/00*   (2006.01)
*A61B 5/20*   (2006.01)
(Continued)

(52) U.S. Cl.
CPC ............. *G16H 40/67* (2018.01); *A61B 5/002* (2013.01); *A61B 5/202* (2013.01); *A61B 5/204* (2013.01);
(Continued)

(58) Field of Classification Search
None
See application file for complete search history.

(56) References Cited

U.S. PATENT DOCUMENTS 11,482,327 B2   10/2022   Ansell et al.
2003/0013959 A1   1/2003   Grunwald et al.
(Continued)

FOREIGN PATENT DOCUMENTS

EP   0271214 A2   6/1988
GB   2497790 A   6/2013
(Continued)

OTHER PUBLICATIONS

International Search Report and Written Opinion of PCT/GB2016/052271 dated Dec. 8, 2016, 19 Pages.
(Continued)

*Primary Examiner* — Amal Aly Farag
(74) *Attorney, Agent, or Firm* — NIXON PEABODY LLP

(57) ABSTRACT

The present invention relates to methods and apparatuses for estimating the status of a bladder, especially with respect to the likelihood of an imminent voiding of the bladder. The apparatuses carry out computer-implemented methods of estimating a bladder status employing a bladder monitor which collects bladder data (e.g. using ultrasound) and transmits the bladder data to a data processor for algorithmic conversion to a bladder status. Such algorithms may be trained and tuned to a particular person's bladder. Having established a bladder status based on otherwise esoteric bladder data, the data processor may then trigger an alert signal where the bladder status meets particular criteria indicating an imminent voiding event. Such a trigger signal may be used to alert a nocturnal enuresis patient to an impending void so that they can be awoken before any bedwetting occurs.

30 Claims, 26 Drawing Sheets

(51) Int. Cl.
*A61B 8/00* (2006.01)
*A61B 8/14* (2006.01)
*G08B 21/18* (2006.01)
*G16H 40/63* (2018.01)
*G16H 40/67* (2018.01)
*G16H 50/20* (2018.01)
*G16H 50/30* (2018.01)

(52) U.S. Cl.
CPC .......... *A61B 5/7267* (2013.01); *A61B 5/7275* (2013.01); *A61B 8/14* (2013.01); *A61B 8/4227* (2013.01); *G08B 21/18* (2013.01); *G16H 40/63* (2018.01); *G16H 50/20* (2018.01); *G16H 50/30* (2018.01); *A61B 5/0002* (2013.01); *A61B 5/6874* (2013.01)

(56) References Cited

U.S. PATENT DOCUMENTS

| | | |
|---|---|---|
| 2003/0084906 A1 | 5/2003 | Roe |
| 2006/0276707 A1 | 12/2006 | Ya'Akov et al. |
| 2007/0073361 A1* | 3/2007 | Goren ................ A61B 5/4035 600/509 |
| 2008/0177398 A1 | 7/2008 | Gross et al. |
| 2008/0300449 A1 | 12/2008 | Gerber et al. |
| 2011/0004123 A1 | 1/2011 | Companion |
| 2011/0119212 A1 | 5/2011 | De Bruin et al. |
| 2011/0124955 A1 | 5/2011 | Ciquin et al. |
| 2012/0064520 A1 | 3/2012 | Aharonov et al. |
| 2012/0268278 A1 | 10/2012 | Lewis |
| 2013/0023786 A1 | 1/2013 | Mani et al. |
| 2013/0046150 A1 | 2/2013 | Devanaboyina |
| 2013/0079621 A1 | 3/2013 | Shoham et al. |
| 2013/0289446 A1* | 10/2013 | Stone .................... A61B 5/725 600/595 |
| 2016/0000378 A1 | 1/2016 | Hall et al. |
| 2018/0214122 A1 | 8/2018 | Ansell et al. |

FOREIGN PATENT DOCUMENTS

| | | |
|---|---|---|
| JP | H07136167 A | 5/1995 |
| JP | H08280676 A | 10/1996 |
| JP | 2002516691 A | 6/2002 |
| JP | 2002369810 A | 12/2002 |
| JP | 2010504578 A | 2/2010 |
| WO | 20004017834 A1 | 3/2004 |
| WO | 2005034717 A2 | 4/2005 |
| WO | 2005099582 A1 | 10/2005 |
| WO | 2007130167 A1 | 11/2007 |
| WO | 2008144449 A2 | 11/2008 |
| WO | 2017017426 A1 | 2/2017 |

OTHER PUBLICATIONS

Search Report of GB1513208.7, dated Nov. 20, 2015, 5 Pages.
Miller, Is Your BMI a lie? Formula that calculates healthy weight is flawed, says Oxford Professor, New York Daily News, 2013.
Notice of Allowance for U.S. Appl. No. 15/747,696 dated Jan. 25, 2018, 10 pages.

* cited by examiner

METHODS AND APPARATUSES FOR ESTIMATING BLADDER STATUS

CROSS-REFERENCE TO RELATED APPLICATIONS

This application is a continuation of U.S. patent application Ser. No. 15/747,696 filed Jan. 25, 2018, issued as U.S. Pat. No. 11,482,327 on Oct. 25, 2022, which is a National Phase of International Application No. PCT/GB2016/052271 filed Jul. 25, 2016, which designated the U.S. and that International Application was published under PCT Article 21 (2) in English. This application also includes a claim of priority under 35 U.S.C. § 119 (a) and § 365 (b) to British patent application No. GB 1513208.7 filed Jul. 27, 2015, the entirety of which is hereby incorporated by reference.

INTRODUCTION

The present invention relates to methods and apparatuses for estimating the status of a bladder, especially with respect to the likelihood of an imminent voiding of the bladder. More particularly the present invention relates to methods and apparatuses for treating urinary incontinence, suitably by providing pre-void alerts that allow a patient to void in a dignified manner.

BACKGROUND

Urinary incontinence, or involuntary urination, is a condition that blights many lives in people of all ages. Perhaps the most recognised types of urinary incontinence include: nocturnal enuresis (bedwetting), urge incontinence (overactive bladder), stress incontinence (inadequate bladder closure due to weak pelvic floor muscles), overflow incontinence (inadequate bladder contraction or urethral blockage), mixed incontinence (complicated by urinary retention), structural incontinence (caused by structural factors, such as ectopic ureter, fistulas, and the like), transient incontinence (a temporary form caused by factors such as medications, mental impairment, stool impaction), double incontinence (both urinal and fecal incontinence), and functional incontinence (difficulty reaching the bathroom in time—usually precipitated by certain medications or health issues—e.g. dementia).

Common treatments for these conditions may include: prescribed exercise, such as pelvic floor muscle training and bladder training; behaviour management; electrical stimulation treatments; urine collecting devices such as urinary bags; absorbent undergarments (e.g. diapers); fixer-occluder devices (which physically restricts urethra); catheters; and surgery. Effective and safe drug treatments remain elusive, though fesoterodine, tolterodine and oxybutynin are sometimes used in therapy.

Nocturnal enuresis (i.e. bedwetting or night-time urinary incontinence) is a special type of urinary incontinence involving involuntary urination during sleep in patients of an age beyond that which bladder control is usually well established. Those diagnosed with primary nocturnal enuresis (PNE) are child patients (typically aged 5 or above, or even 7 and above) who have yet to experience a prolonged period of dryness, whereas secondary nocturnal enuresis (SNE) is a further sub-category ascribed to (adult or child) patients who relapse into bedwetting following a prolonged period of dryness or otherwise experience involuntary bedwetting, usually as a result of a medical condition, such as a bladder infection.

Nocturnal enuresis is the involuntary discharge of urine at night in a child aged 5 years or older in the absence of congenital or acquired defects of the central nervous system or urinary tract.[1] The causing factors associated with nocturnal enuresis can be found in Kalyanakrishnan's study.[2] Children without any previous dry period for >6 months are said to have primary enuresis.[3]

Nocturnal enuresis affects 15% to 20% of 5-year-old children, 5% of 10-year-old children, and 1% to 2% of people aged 15 years and older. Though, in the absence of treatment, 15% of affected children become dry each year[4], nocturnal enuresis is a widespread problem for both patients and carers. Moreover, various forms of urinary incontinence are common amongst adults (including SNE), especially amongst the elderly and those having suffered a medical condition, such as a stroke, which adversely impacts bladder control.

Treatments for nocturnal enuresis include many of the same treatments applied to more general urinary incontinence conditions (e.g. behaviour management, motivational therapy, absorbent undergarments and/or mattress protectors). In addition, "bedwetting alarms" have been developed especially to tackle nocturnal enuresis. Such alarms, which may be worn by a patient during sleep, notionally provide a means of training a child to "sense" a full bladder by awaking the child in response to the detection of urinary moisture. Though such bedwetting alarms have been used with some degree of success, this success relies on a high degree of compliance and adherence to prescribed procedures, which can be extremely disruptive to patient, carers, and family. As such, non-compliance is a significant problem which can mean that the bedwetting alarms can cause more problems than they solve. Moreover, when using such an alarm system, the patient will still often discharge large quantities of urine since being awoken mid-discharge may be too late. Moreover, even where the alarm does successfully awaken a patient before full discharge of the bladder's contents, failure thereafter to reach the bathroom in time may further exacerbate distress caused by the condition.

WO2003039343 describes a method of urinary continence training using bladder content measurements to identify opportunities for continence training, whereby an alert threshold is gradually increased during the training.

WO2001000117 describes a disposable wearable sensor to detect electrical activity in the wearer's smooth colonic muscles, abdominal muscles or the muscles surrounding the bladder or rectum which may indicate impending discharge of bodily waste.

WO2005034717 describes an ultrasound device which indicates a distance between walls of a bladder.

WO2008150592 describes an implantable medical device (IMD) is configured to operate as an automatic voiding diary for logging urinary and/or fecal voiding events.

U.S. Pat. No. 6,213,949 describes a system for estimating the volume of fluid in the bladder by sequentially scanning the bladder with ultrasonic beams that section the bladder into a number of transverse planes.

US20060276707 describes a method of monitoring urine levels in the bladder via multi-frequency electromagnetic wave analysis.

U.S. Pat. No. 5,341,127 describes a bedwetting alarm which senses the presence of urine and activates a low frequency vibration alarm.

WO1999062402 describes systems for monitoring a patient's bladder urine distention level.

It is therefore an object of the present invention to address at least one of the problems of the prior art.

Another object of the invention is to provide a non-invasive technique for detecting an imminent likelihood of voiding (i.e. bladder emptying).

Another object of the invention is to alert a urinary incontinence patient of an imminent likelihood of voiding.

SUMMARY OF THE INVENTION

According to a first aspect of the present invention there is provided a computer-implemented method of estimating a bladder status, via a computer system comprising:
 a data-processor in wired and/or wireless communication with a bladder monitor configured to acquire real-time bladder data from a bladder, and data storage comprising status-mapping data;
wherein the method comprises:
  (i) the data-processor receiving status-mapping data from the data storage;
  (ii) the data-processor receiving real-time bladder data from the bladder monitor (wherein suitably the real-time bladder data discernibly changes with changing bladder-urine content);
  (iii) the data-processor generating a real-time bladder status (suitably indicative of a likelihood of imminent voiding), based on the real-time bladder data;
wherein:
  the status-mapping data encodes a (bladder-specific) predictive model by which the bladder's contents can be estimated from the real-time bladder data, thereby facilitating mapping of real-time bladder data to a bladder status; and
  generating the real-time bladder status comprises the data processor correlating the real-time bladder data, by reference to the status-mapping data, with a bladder status.

According to a further aspect of the present invention there is provided a bladder status estimating system (suitably an apparatus for use in the computer-implemented method of estimating a bladder status as defined herein), the system comprising:
 a data-processor in wired and/or wireless communication with a bladder monitor operable to acquire real-time bladder data from a bladder, and data storage comprising status-mapping data;
wherein:
 the data-processor is operable:
  to receive status-mapping data from the data storage and to receive real-time bladder data from the bladder monitor;
  to generate a real-time bladder status, based on the real-time bladder data;
wherein:
 the status-mapping data encodes a (bladder-specific) predictive model by which the bladder contents can be estimated from the real-time bladder data, thereby facilitating mapping of real-time bladder data to a bladder status; and
 the data processor generates the real-time bladder status by correlation of the real-time bladder data, by reference to the status-mapping data, with a bladder status.

Suitably the real-time bladder data comprises reflected attenuation signals from a bladder and/or related media around the bladder. The real-time bladder data may comprise or be processed to comprise signal segments (i.e. through segmenting signals appropriately). Suitably the real-time bladder data may then be correlated with a bladder status utilising certain characteristic features extracted from different segments of the signal(s).

Most suitably the bladder status estimating system and associated apparatuses and methods comprise a status-mapping data producer and/or a status-mapping data refiner.

Most suitably the bladder status estimating system and associated apparatuses and methods comprise a status-mapping data training system, which suitably refines the status-mapping data, suitably by reference to event data relevant to the bladder and/or machine learning algorithms, to customise the status-mapping data for a particular bladder.

According to a further aspect of the present invention, there is provided a computer-implemented method of providing a pre-void alert (or suitably a method of treating urinary incontinence, in a patient in need of such treatment), via a computer system comprising:
 a data-processor in wired and/or wireless communication with a bladder monitor configured to acquire real-time bladder data from the patient, and data storage comprising status-mapping data;
wherein the method comprises:
  (i) the data-processor receiving status-mapping data from the data storage;
  (ii) the data-processor receiving real-time bladder data from the bladder monitor (wherein suitably the real-time bladder data discernibly changes with changing bladder-urine content);
  (iii) the data-processor generating a real-time bladder status (suitably indicative of a likelihood of imminent voiding), based on the real-time bladder data;
  (iv) the data-processor determining whether the bladder status satisfies one or more predetermined pre-void trigger criteria (e.g. >¾ full) and:
   a. if so, triggering a pre-void alert event; or
   b. if not, repeating at least steps (ii) to (iv);
wherein:
 the status-mapping data is particular to the patient and encodes a patient-specific predictive model by which the patient's bladder-urine content can be estimated from the real-time bladder data, thereby facilitating mapping of real-time bladder data to a bladder status;
 generating the real-time bladder status comprises the data processor correlating the real-time bladder data, by reference to the status-mapping data, with a bladder status; and
 the pre-void alert event comprises the data processor producing a unique output signal, optionally for use by an auxiliary device that is in wired or wireless communication with the data-processor.

Suitably the real-time bladder status may be generated based on features extracted from different segments of the signal(s) of the real-time bladder data as set forth above in relation to the apparatus.

According to a further aspect of the present invention there is provided a pre-void alert system (suitably an apparatus for use in the computer-implemented method of treating urinary incontinence as defined herein), the system comprising:
 a data-processor in wired and/or wireless communication with a bladder monitor operable to acquire real-time bladder data from a patient, and data storage comprising status-mapping data;

wherein:
the data-processor is operable:
to receive status-mapping data from the data storage and to receive real-time bladder data from the bladder monitor;
to generate a real-time bladder status, based on the real-time bladder data;
to determine whether the bladder status satisfies one or more predetermined pre-void trigger criteria (e.g. >¾ full) and:
i. if so, trigger a pre-void alert event; or
ii. if not, continue to receive real-time bladder data, generate real-time bladder status, and determine whether the bladder status satisfies one or more predetermined pre-void trigger criteria;

wherein:
the status-mapping data is particular to each patient and encodes a patient-specific predictive model by which the patient's bladder-urine content can be estimated from the real-time bladder data, thereby facilitating mapping of real-time bladder data to a bladder status;
the data processor generates the real-time bladder status by correlation of the real-time bladder data, by reference to the status-mapping data, with a bladder status; and
the pre-void alert event involves the data processor producing a unique output signal, optionally received and used by an auxiliary device that is in wired or wireless communication with the data-processor.

According to a further aspect of the invention there is provided a computer program comprising software code for performing the computer-implemented method of estimating a bladder status or computer-implemented method of providing a pre-void alert (or treating urinary incontinence), as defined herein, when the computer program is run on a computer/smartphone (which computer may comprise or in communication with the data-processor). The computer may, for example, be a computer located within or otherwise associated with a hand-held device, suitably a hand-held (tele)communications device such as a smartphone or tablet.

According to a further aspect of the present invention, there is provided a computer-readable medium comprising software code executable to cause a computer to perform the computer-implemented method of estimating a bladder status or computer-implemented method of providing a pre-void alert (or treating urinary incontinence), as defined herein, when the software code is executed on a computer (which computer may comprise or in communication with the data-processor).

According to a further aspect of the present invention there is provided a data structure for facilitating determination of an individual patient's bladder status (suitably for use in a computer-implemented method of treating urinary incontinence as defined herein), the data structure comprising patient identification information and status-mapping data, wherein the status-mapping data is particular to the patient and encodes a patient-specific predictive model by which the patient's bladder-urine content can be estimated and the patient's bladder status determined.

According to a further aspect of the present invention there is provided a wearable bladder monitor, the bladder monitor comprising:
at least one sensor operable to receive real-time bladder data; and
a (wired or wireless) interface or connection for conveying the real-time bladder data to a data-processor.

According to a further aspect of the present invention there is provided a skin-interfacing device (suitably for facilitating transmission of signals between animal or human skin and an external device, such as a bladder monitor, suitably without the external device or the interfacing part thereof being in direct contact with the skin), wherein the skin-interfacing device comprises:
a compressible absorbent core impregnated with a skin-interfacing composition, wherein the absorbent core secretes the skin-interfacing composition in response to a compression force.

A method of providing a skin interface between animal or human skin and an external device, the method comprising:
compressing the skin-interfacing device, as defined herein, between the skin and the external device.

Suitably the skin-interfacing device provides (substantially) no acoustic impedance (Z) difference between a transducer (e.g. located within the external device) and the skin and/or body.

According to a further aspect of the invention there is provided a method of obtaining data (including images) from an animal or human body, the method comprising compressing the skin-interfacing device, as defined herein, between the skin of the animal or human body and a data collection device; and operating the data collection device to obtain data from the animal or human body.

According to a further aspect of the invention there is provided a method of diagnosing and/or prognosing a medical condition or disorder, the method comprising obtaining data (optionally including images) via the method of obtaining data from an animal or human body as defined herein, and determining a diagnosis and/or prognosis on the basis of the obtained data.

According to a further aspect of the invention there is provided a method of obtaining information regarding an animal or human body, the method comprising: transmitting an incident ultrasound signal to or into the animal or human body; detecting one or more echoed signals arising from the incident ultrasound signal; identifying any discriminant features (e.g. ultrasound harmonics) of the echoed signals; and, on the basis of the discriminant features (e.g. harmonic(s)) of the echoed signals, extrapolating information regarding the animal or human body.

The incident ultrasound signal may comprise one or more sonar wave pulses. Detecting echoed signals may comprise detection of echoes arising from every voxel of the tissues which the incident ultrasound signal interacts with.

According to a further aspect of the invention there is provided a method of diagnosing and/or prognosing a medical condition or disorder, the method comprising obtaining information regarding an animal or human body, as defined herein, and determining a diagnosis and/or prognosis on the basis of the obtained information.

According to a further aspect of the present invention, there is provided a use of harmonic ultrasound signals for obtaining information regarding an animal or human body (e.g. the volume/level of urine in the bladder).

According to a further aspect of the present invention, there is provided a computer-implemented method of producing and/or refining (or training) status-mapping data (for treating urinary incontinence, in a patient in need of such treatment), via a computer system comprising:
a data-processor in wired and/or wireless communication with:
a bladder monitor configured to acquire real-time bladder data from the patient;

a bladder-related event data collection facility configured to manually and/or automatically collect event data from the patient; and data storage for storing time-stamped real-time bladder data, time-stamped bladder-related event data, and status-mapping data;

the method comprising:
(i) the data-processor receiving real-time bladder data from the bladder monitor (wherein suitably the real-time bladder data discernibly changes with changing bladder-urine content);
(ii) storing the real-time bladder data in the data storage with an associated time-stamp indicative of when the data was obtained;
(iii) the data-processor receiving bladder-related event data (optionally from the bladder monitor itself where it is equipped to do so);
(iv) storing the bladder-related event data in the data storage with an associated time-stamp indicative of when the data was obtained;
(v) identifying any relationships between time-stamped real-time bladder data and time-stamped bladder-related event data; and, where a relationship is identified, on the basis of said relationship correlating the real-time bladder data with a bladder status (suitably indicative of a likelihood of imminent voiding);
(vi) producing and/or refining status-mapping data based on any correlations between bladder data and bladder status;
(vii) optionally repeating (i) to (ix) to further refine the status-mapping data (suitably to increase the accuracy of correlations between bladder data and bladder status);

wherein:
the status-mapping data is particular to the patient and encodes a patient-specific predictive model by which the patient's bladder-urine content can be estimated from the real-time bladder data, thereby facilitating mapping of real-time bladder data to a bladder status.

According to a further aspect of the present invention there is provided a bladder monitor (suitably for monitoring changes in a subject's bladder over time, suitably as defined elsewhere herein) comprising two or more thermal (e.g. infrared) detectors, wherein suitably one of the thermal detectors is configured (suitably by virtue of location in/on the bladder monitor) to have greater sensitivity towards temperature changes in (or attributable to) the bladder than one of the other thermal detectors.

According to a further aspect of the present invention there is provided a method of detecting a change in bladder state of a subject, the method comprising repeatedly obtaining two or more specific thermal measurements from a subject, wherein one of the specific thermal measurements is more sensitive to temperature changes in (or attributable to) the bladder than one of the other thermal detectors; and correlating differences in the one or more specific thermal measurements with a bladder state and/or change thereof. Suitably the more "bladder-sensitive" thermal measurement is obtained via a thermal detector located closer to the bladder than the less "bladder-sensitive" thermal measurement. This method suitably employs a bladder monitor comprising two or more thermal detectors as herein defined. The thermal detectors of the bladder monitor are thus suitably located to achieve the measurement sensitivities required of this method.

The bladder monitor and/or methods involving thermal detectors/measurements may be integrated with any of the other bladder monitor or method features defined elsewhere herein.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

DETAILED DESCRIPTION OF THE INVENTION

General Points and Advantages of the Invention

The bladder status estimating systems of the invention provide a unique way of acquiring and processing data to deliver an accurate automated method of predicting real-time bladder behaviour—e.g. urine volume within the bladder. Such a system advantageously enables the delivery of pre-void alerts/alarms (e.g. alerts prior to bedwetting rather than afterwards), which may serve a number of functions, including but not limited to: treating urinary incontinence (e.g. nocturnal enuresis, incontinence in the elderly, incontinence in stroke victims), bladder control training or toilet training (e.g. young children, pets such as dogs), or even just as a warning system to enable action to be taken prior to voiding.

Systems of the invention are relatively non-invasive, non-restrictive (subjects wearing a bladder monitor of the invention are not necessarily restricted in terms of movement), comfortable, free of pharmaceutical side effects, highly customisable, easy to comply with, and most importantly serve to avoid the indignity, discomfort, and inconvenience of uncontrolled voiding. It also provides pet owners (e.g. dog owners) with an extremely useful tool to reduce mess caused by pets (especially young pets) and to help during the bladder training process (e.g. when alerted, a dog owner can take a dog to an appropriate place just prior to voiding).

The training systems provided by the invention, which can interface with or be integral to a bladder status estimating system of the invention, also provide a tool for dramatically improving the accuracy of bladder status predictions, especially given the variability in bladder behaviour from person to person, species to species, etc.

Figure 35:
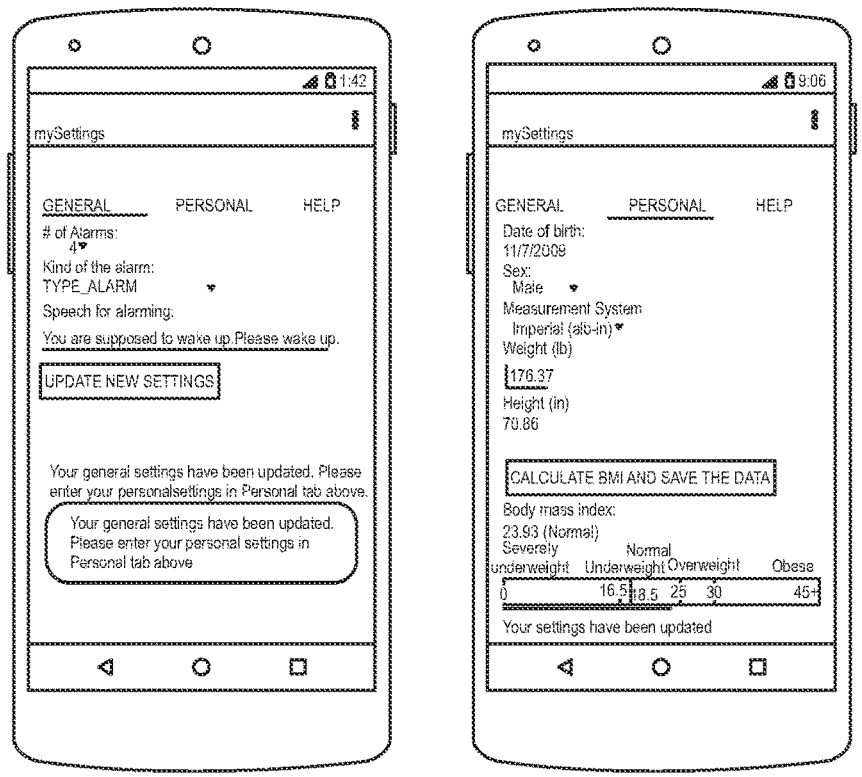
FIG. 35 shows the screen shots of the smartphone application showing customizing of the system based on personal features.
Figure 36:
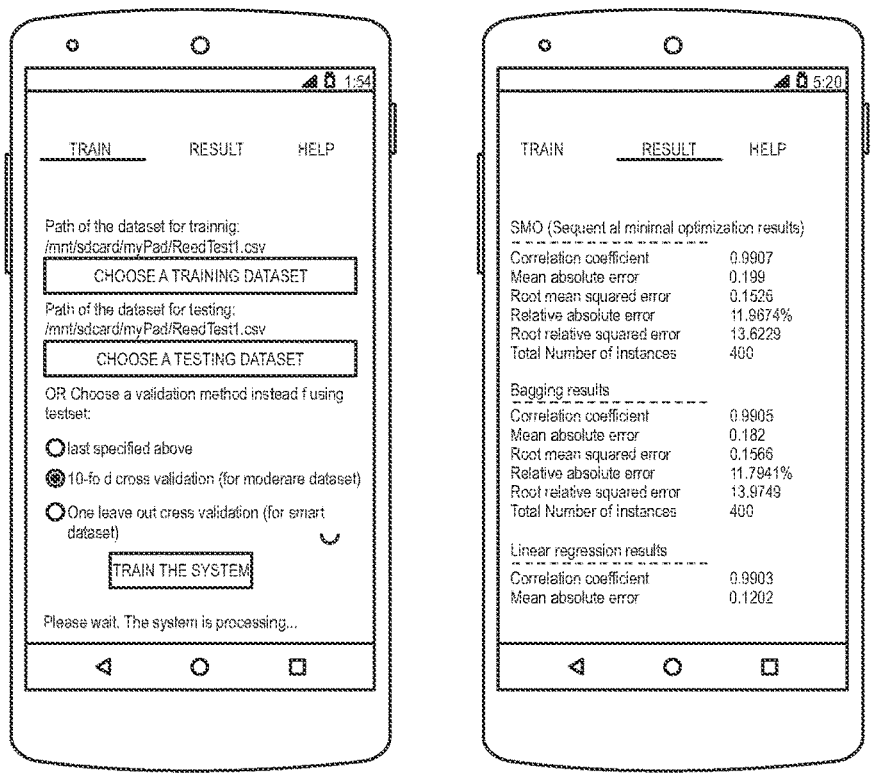
FIG. 36 has the screen shots of the smartphone application showing training of the system based on the instances acquired either from the general datasets or personal datasets.
Figure 37:
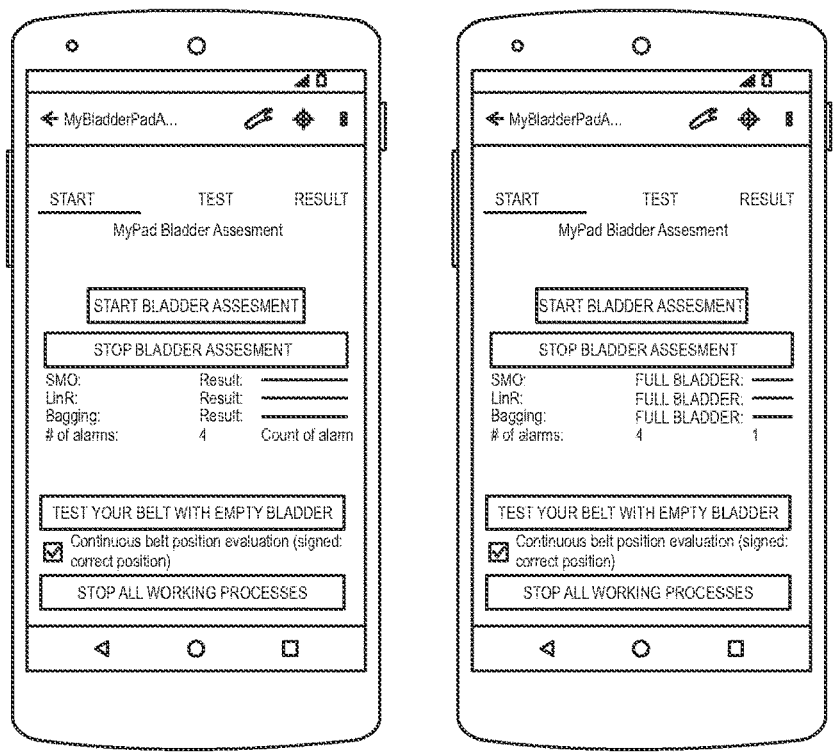
FIG. 37 has the screen shots of the smartphone application showing a test of the system for deciding on the state of the bladder in terms of the instance obtained from either general datasets or personal datasets.

The computer-implementation of the invention also provides a high degree of flexibility and customisability to suit any particular situation. For instance, alerts may be sent to a urinary incontinence patient themselves, to enable them to avoid premature voiding, or to a third party who can intervene at the right time (e.g. as per dog owners using the system on their dogs). Moreover, the or part of the system may be controlled by a convenient device, such as a smartphone or tablet (via an appropriate "app"), to reduce the physical footprint of the system and improve system development by way of firmware and software updates. Furthermore, data processing (e.g. of bladder data, event data, and/or status-mapping data and dataset training) may be partially or fully performed by a convenient device, such as a smartphone or tablet (again via an appropriate "app"), which may optionally perform some data-processing through one or more other interfacing or network-interfacing computers or servers. An embodiment of a suitable smartphone application which performs some or all of these functions is illustrated in FIGS. 35, 36, and 37.

Furthermore, embodiments employing ultrasound methods to obtain bladder data are particularly advantageous due to the highly distinctive signature patterns attributable to urine-containing bladders. This in turn enables the use of safe low power ultrasound pulses without loss of accuracy, especially when using echoed signals from multiple points of the bladder and especially when examining signal attenuation and echo harmonics.

Moreover, the skin-interfacing devices of the invention, especially when used with ultrasound detection systems, dramatically improve the performance of the bladder status estimating systems of the invention as well as other data-collection systems (e.g. in ultrasound imaging) whilst minimising the discomfort and inconvenience of having to apply an unpleasant gel or fluid to the skin.

Bladder Monitor

The bladder monitor is suitably operable to collect bladder data from a human or animal bladder, suitably a patient suspected of a form of urinary incontinence, such as nocturnal enuresis. As such, the bladder monitor suitably comprises one or more sensors or transducers capable of collecting data (e.g. time-domain and frequency-domain signals pertaining to waveforms, be them electromagnetic, sound, ultrasound, or some other waveform) from which information regarding the bladder can be obtained. Suitably the information facilitates an estimation of bladder-urine content and/or a likelihood of an imminent voiding event. The one or more sensors may include two or more different types of sensor, or two or more similar or identical sensors. Multiple sensors can assist self-calibration which may be required when a subject moves to thereby suddenly change key bladder attributes which need to be accommodated in bladder-status prediction algorithms.

Suitably the transducer(s) are single-element transducer(s) configured to transmit and receive simultaneously.

Most suitably, the one or more sensors comprise or consist of one or more ultrasound transducers. Suitably the ultrasound transducer is configured to transmit ultrasound waves of a frequency between 0.5 and 40 MHz, more suitably between 1 and 10 MHz, more suitably between 2 and 5 MHz, most suitably between 2 and 3.5 MHz. In a particular embodiment, the ultrasound frequency is 2.2 MHz. Suitably such ultrasound transducers are configured to detect echoed attenuation signals from a bladder, and is suitably configured to detect attenuation signals reflected at a range of between 0.5 and 20 cm from the transducer, suitably at a range of between 1 and 15 cm from the transducer, suitably at a range between 4 and 13 cm from the transducer(s). Suitably the ultrasound transducers are configured to detect echoed attenuation signals from a bladder, and is suitably configured to detect attenuation signals reflected at a range of between 0.5 and 30 cm from the transducer, suitably at a range of between 1 and 25 cm from the transducer, suitably at a range between 4 and 20 cm from the transducer(s).

Suitably the or each transducer operates at 2-5 MHz. Suitably the or each transducer is configured or operable (or the bladder monitor is configured to operate the or each transducer) to transmit pulses of ultrasound.

Suitably the pulse width is between 50 ns and 5 µs, suitably between 100-1000 ns, suitably between 400-800 ns. Suitably the pulse width is 600 nanoseconds (ns).

The propagation speed is suitably between 500 and 3000 m/s, suitably between 1000 and 2000 m/s, suitably between 1300 and 1700 m/s, suitably 1540 m/s. Propagation speed is a function of:

$$\text{Wavelength (mm)} = \text{Propagation Speed (mm/microsecond)}/\text{Frequency (MHz)}$$

Suitably the wavelength of the incident ultrasound is between 0.5 and 10 mm, suitably between 1 and 5 mm, suitably between 3 and 4 mm. Suitably the wavelength of the incident ultrasound is 3.388 mm. Suitably the wavelength of the incident ultrasound is between 0.1 and 5 mm, suitably between 0.3 and 2 mm, suitably between 0.4 and 1 mm. Suitably the wavelength of the incident ultrasound is 0.7 mm ($\lambda = 1540$ m/s/$2.2 \times 10^6$ Hz. 0.7 mm).

Suitably the incident ultrasound is a single frequency/wavelength or single frequency/wavelength range, suitably with a bandwidth less than or equal to 1 MHz, suitably less than or equal 100 KHz, suitably less than or equal to 10 KHz, suitably less than or equal to 1 KHz, suitably less than or equal to 100 Hz, suitably less than or equal to 10 Hz.

Suitably, the pulse repetition frequency (PRF) is between 10 Hz and 2 KHz, suitably between 50 Hz and 500 Hz, more suitably between 100 and 300 Hz, most suitably about 200 Hz. The PRF is suitably tunable, suitably between 200 and 2000 Hz.

Suitably the power of each ultrasound pulse (or total power used by all transducers) is between 0 and 3 W/cm$^2$, suitably between 0.01 and 0.05 W/cm$^2$. Suitably the intensity of the beam (or total power used be all transducers) is 0.03 W/cm$^2$ using Low Intensity Pulsed Ultrasound (LIPUS).

Suitably the ultrasound transducer operates at a voltage of between 10 and 1000 V, suitably between 20 and 500 V, suitably between 60 and 300 V, suitably at 70-130V, suitably between 60 and 100V, most suitably at about 100V.

Suitably the bladder monitor runs pursuant to computer software (whether the software is run on a remote computer or locally within the bladder monitor) which intelligently adjusts the time gap between successive bladder readings (i.e. ultrasound doses), suitably depending on a real-time estimate of the current bladder level/volume. Suitably the time gap between successive bladder readings is configured to contract as the bladder fills with urine. Suitably, the time gap for a (substantially) empty bladder is set between 10 and 30 minutes, suitably about 20 minutes. Suitably, the time gap for a half-full bladder is set between 2 and 8 minutes, suitably about 5 minutes. Suitably the time gap as a whole is between 2 and 30 minutes, suitably between 5 and 20 minutes, depending on the bladder status/fill state.

Suitably the bladder monitor and/or ultrasound transducers are configured such that the attenuation signal echoed from the anterior wall of the bladder is at least 0.2 dB, suitably at least 0.5 dB, suitably at least 1 dB, suitably at least 1.5 dB.

Suitably the bladder monitor is operable to apply a gain to attenuation signals of between 0 and 100 dB, suitably between 20 and 80 dB. Suitably the gain applied to attenuation signals is between 50 and 60.5 dB, most suitably 50 dB. The gain is suitably optimised to maximise distinctiveness between particular attenuation signals.

The bladder monitor is suitably an external monitoring device—i.e. may be used outside of a patient's body.

Suitably the bladder monitor comprises a housing. Suitably sensors are located on a rear face of the housing, which rear face is suitably intended to be placed against a subject's lower abdomen. Suitably the rear face of the housing has a curved profile, suitably a concave structure. Suitably an opposing front face of the housing has a corresponding convex profile.

Suitably the bladder monitor comprises one or more strap attachment elements, such as longitudinal strap holes, to or through which a strap may be attached to allow the bladder monitor to be attached to a subject in a comfortable manner. Alternatively, there may be provided a purpose-built bladder monitor strap comprising a pocket into which the bladder monitor fits, the pocket and strap comprising one or more apertures to expose any relevant sensors or transducers at the rear face of the bladder monitor. Whichever kind of strap is utilised with the bladder monitor, suitably the strap comprises one or more complementary attachment elements to allow the strap to be closed in a closed loop around the subject to which the bladder monitor is strapped. It will be appreciated that alternative methods of mounting the bladder monitor to a subject are also viable, including purpose-built pockets within certain items of clothing.

In an embodiment, the front face of the bladder monitor comprises one or more event buttons or triggers which may be operated to record the timing of one or more specific events, such as a voiding event.

The bladder monitor suitably comprises an on-board clock, suitably to enable time-stamping of collected bladder data and/or event data.

The bladder monitor suitably comprises data storage upon which bladder data and/or event data may be stored, temporarily or permanently.

The bladder monitor suitably comprises a communication element (e.g. a transceiver) to enable transmission of bladder data and/or event data to a remote data processor. However, in a particular embodiment the bladder monitor comprises the data processor.

The bladder monitor suitably comprises a data processor (even if separate from a data processor which performs the majority of bladder-data processing), suitably with a CPU and RAM to allow, suitably to allow the bladder monitor to operate pursuant to instructions provided by a computer program. The bladder monitor is suitably configured to transmit pulsed ultrasound and collect and/or or record echoed attenuation signals as raw bladder data.

Skin-Interfacing Device

The skin-interfacing device suitably comprises an absorbent core impregnated with a composition facilitating transmission of electromagnetic, sound, or ultrasound waves, preferably ultrasound waves, preferably ultrasound waves having a wavelength between 1 and 40 MHz. Impregnation may be achieved by immersing the absorbent core within a reservoir of the composition, or by injecting and/or coating the absorbent core with the composition. Suitably the absorbent core is exposed to a vacuum to facilitate degassing after impregnation.

Suitably the composition is a degassed composition, suitably free of air bubbles. Suitably the composition is a water-based and/or alcohol-based gel having a viscosity of 1,000-100,000 cps, suitably 10,000 to 50,000 cps, suitably 20,000-45,000 cps. Suitably the composition is a hydrogel.

Suitably the composition comprises one or more preservatives.

Suitably the composition comprises one or more skin-care agents, such as moisturiser(s).

Suitably the skin-interfacing device is packaged within an air-tight package, suitably an evacuated package. Suitably the absorbent core is an absorbent pad. Suitably the absorbent core comprises a porous material, suitably a fibrous material, suitably a porous and/or fibrous hydrophilic material. Suitably the absorbent core may be made of any absorbent material acceptable for contact with human or animal skin.

Suitably prior to use, the absorbent core is encapsulated within and/or sandwiched between removable backing sheet(s), such as sticky-backed sheets. Suitably the sheets help to preserve and/or retain the composition within the absorbent core on store and prior to use.

The absorbent core is suitably dimensioned to cover a sufficient area of a subject's abdomen to which the absorbent core is intended to be applied. Suitably the absorbent core is an absorbent pad having an average (uncompressed) thickness of between 0.01 and 5 cm, more suitably 0.1 and 1 cm. Suitably the absorbent pad has a front face and a rear face, one of which is intended for contact with skin and the other of which is intended for contact with one or more sensors, for example, the one or more sensors of bladder monitor according to the invention. As such, suitably the front and/or rear face of the absorbent pad suitably have a surface area between 2 square centimetres and 200 square centimetres.

Suitably the skin-interfacing device is configured such that compressing the absorbent core causes the composition impregnated therein to leach out of both the rear and front face to provide a medium (of the composition) linking the skin to a monitoring or sensing device.

Computer System

The methods, systems, and apparatuses of the invention generally involve a computer system. Such a computer system suitably comprises a bladder monitor, a data processor, and data storage.

The bladder monitor is suitably operable to collect bladder data, or raw bladder data which may be subsequently translated into bladder data.

The data processor is suitably configured to process the bladder data, and may suitably process raw bladder data into processed bladder data. The data processor is suitably also configured to generate a bladder status based on the bladder data, whether raw or processed. The data process is also suitably configured to determine whether the bladder status meets a predetermined pre-void trigger criteria and, if so, respond by triggering a pre-void alert event that may trigger an alarm or such like.

The data processor is also suitably configured to receive and/or process bladder-related event data, such as the timing and/or extent of food/drink consumption and/or the timing (and possibly volume) of a bladder voiding event. The data processor may suitably utilise such event data to produce or refine any status-mapping data used to estimate bladder status from bladder data. Suitably such refinements of status-mapping data are performed by correlating time-stamped event data with relevant time-stamped bladder data (e.g. bladder data falling between two time-stamped events and/or either side of said two events) and potentially cross-referencing existing estimated correlations between bladder data and bladder status (e.g. default status-mapping data which may be used in the absence of any refinements, and which may be derived from a database, and potentially include status-mapping data corresponding to a generic group or cohort into which a particular patient or user fits—e.g. by virtue of their age, gender, BMI, etc.). The data processor may be configured with machine learning software to allow status-mapping data to be continually or periodically refined.

The data storage, which may be volatile or non-volatile, though most suitably non-volatile, is suitably configured to store status-mapping data. The data storage may also be configured to store bladder data, whether raw and/or processed bladder data. The data storage may be configured to store bladder statuses. The data storage may be configured to store bladder-related event data. Suitably any bladder data, bladder statuses, and/or bladder-related event data are stored with a corresponding time-stamp which reflects the data and time the relevant data was obtained or produced. The data storage may be configured to store status-mapping training data (e.g. testable/trainable sets of bladder data and bladder statuses, suitably with each time-stamped recorded stored as a time-stamped pair of bladder data and corresponding bladder status or estimated status). Such status-mapping training data may be utilised to refine the status-mapping data used in bladder status estimations. The data storage may be configured to store default-status mapping data, which may represent status-mapping data that is generic or non-customised. Such generic status-mapping data may, however, still be approximately tailored for a particular person based on the person's attributes. Such attributes may include age, gender, body-mass index (BMI), medical history (e.g., time intervals of bed wetting, amount of urine detected during voiding), etc. As such, the default status-mapping data may be selected from a set of defaults each applicable for a different set of attributes. Such defaults may be stored on a database. Production of such defaults is discussed in more detail in the Examples/Data section.

As a skilled person in the field of computer science will readily appreciate, the functions of data processing and data storage may be arranged, distributed, and/or delegated in a variety of ways. In the context of the invention, a data processor may include a plurality of data processors, though suitably such data processors are in wired or wireless communication with one another, or otherwise connected via a network interface, albeit access permissions and gateways may restrict their interconnectivity. For instance, raw bladder data may be stored on one computer or server, whilst processed bladder data may be stored elsewhere. The status-mapping data may be stored in a different place to any status-mapping training data, given that testing/training algorithms may consume significant processing resources. The data processor may include just a single data processor, which may optionally be included as part of the bladder monitor itself. Suitably, once the system is trained (e.g. using machine learning techniques with processed datasets) neither raw nor processed datasets are needed during the diagnosis/prognosis phase. Instead, the system may then employ the trained function that is the product of the training process for diagnosis/prognosis.

Likewise, data storage can be distributed or consolidated in any number of places. Crucially, some or all of the various components of the computer system can access the required data at the required time to enable functioning of the system. As such, suitably a data-processor is in wired and/or wireless (e.g. Bluetooth) communication with both a bladder monitor and data storage comprising the status-mapping data.

A computer system may suitably comprise a computer (e.g. PC, laptop, smartphone, tablet, or other such device) that communicates with the bladder monitor and/or components thereof, suitably in a wireless fashion (e.g. via Bluetooth). For example, the computer may be operable to transmit wireless triggers to activate one or more transducers, suitably one at a time (where a plurality, suitably 3, transducers are employed within the bladder monitor). Suitable hardware and software to implement such technology may include those available from Lecoeur Electronique (www.lecoeur-electronique.com). Lecour Electronique's US-SPI hardware may, for example, be incorporated within the bladder monitor or be otherwise in communication therewith, and may communicate with a remote computer (e.g. smartphone) which provides operating instructions/triggers.

Acquiring and Extracting Information from Bladder Data

The bladder monitor is suitably able to acquire real-time bladder data, suitably pursuant to instructions provided by a computer program running either within the bladder monitor or upon a remote device which communicates instructions to the bladder monitor (e.g. a remote data processor).

Acquisition of bladder data suitably involves detecting and/or recording signals from a bladder (whether directly or indirectly through reflections or echoes), suitably echoed ultrasound attenuation signals and/or echoed ultrasound harmonic signals. Multiple signals may be detected and recorded via a plurality of sensors or transducers. Such recorded signals may constitute bladder data or raw bladder data, which may constitute the essential information in itself (i.e. information from which a bladder status may be derived) or may constitute data from which bladder information can extracted. The acquisition of such signals is discussed in more detail elsewhere herein.

Acquisition of bladder data suitably comprises detecting two or more echoed attenuation signals (of interest), suitably via a single transducer. Suitably each attenuation signal (of interest) may be correlated with a particular interface (i.e.

change in media type within the bladder, e.g. urine-tissue barrier) causing the relevant echo. Suitably the bladder data comprises an echoed attenuation signal that correlates with an anterior bladder wall and (suitably where the bladder is non-empty) an echoed attenuation signal that correlated with a posterior bladder wall. Each echoed attenuation signal (of interest) may be identified as a specific "gate" (e.g. time window over which a particular characteristic attenuation signal is received). The absolute times at which each particular gate occurs, and indeed relative time differences between two or more particular gates, may vary in a short term (e.g. as a patient breathes) and over a longer term (e.g. as a bladder fills with urine). Suitably any "short term" variations may be normalised, averaged, or otherwise accounted for in methods of the invention (e.g. using real-time bladder data obtained following a series of ultrasound pulses over sufficient time for at least one patient breathing cycle). Suitably longer-term variations may, however, be used to determine a bladder status, suitably in conjunction with one or more other techniques. However, methods of the invention may suitably involve extracting data from particular "gates" (specific echoed attenuation signals) regardless of their relative timings. As such, bladder data may be obtained that is not dependent on breathing.

Extracting information from the bladder data depends on the technique used. In the case of echoed ultrasound attenuation signals, then information may include: distances between key reflection points (e.g. anterior and posterior bladder walls), nature of the bladder wall (e.g. degree of stretching), nature of bladder contents (whether contains air, gases, and/or urine), signal propagation distances through urine (e.g. harmonic signals or other artefacts resulting from non-linear signal propagation through a medium), position and/or shape of bladder (e.g. use of multiple sensors can provide such information). Obtaining such information from echoed ultrasound signals is explained elsewhere herein. It is self-evident that information may be extracted from other forms of signal in a similar manner, using the idiosyncrasies particular to the type of signal.

The extracted information may constitute bladder data (or a part thereof), and may be operated upon by relevant classifiers, optionally along with raw bladder data, during the process of generating a bladder status.

Suitably, information extraction is performed by a data processor, suitably where the data processor is remote from but in (preferably wireless) communication with the bladder monitor.

All bladder data and/or bladder information is suitably time-stamped by reference to one or more internal clocks of the pre-void alert system. In preferred embodiments, both the bladder monitor and any external data processors comprise a clock, suitably both of which are synchronised. Pulse emission time intervals (PETI) are suitably determined by computer software based on the current obtained status of the urine in the bladder which minimizes the amount of signals emitted to the body: the smaller the level of the urine within the bladder, the longer PETI, and vice versa, the bigger the level of the urine within the bladder, the shorter PETI.

Acquiring and Extracting Information from Event Data

The pre-void alert system is suitably capable of acquiring real-time event data—e.g. the pre-void alert system suitably comprises an event data collection facility. Event data, described in more detail elsewhere herein, suitably includes bladder-related events of the bladder monitor user, such as a food/drink consumption event or a bladder-voiding event, which may suitably be indicative of urine volume at a given point in time. The event data suitably includes a plurality of data fields, for example: event type (e.g. food consumption, drink consumption, bladder-voiding, or even when the subject first feels an urge to urinate), event time (i.e. a time-stamp), and optionally other useful data, for example, quantities (e.g. quantity drunk or eaten; quantity of urine produced during voiding).

The event data may be collected in a variety of ways (either through manual input or automated collection), since there is less need for any physical association between the event data "collector" and the bladder itself (unlike the bladder monitor which needs to be located near the bladder under scrutiny). However, for convenience, the bladder monitor itself may comprise part or all of the event data collection facility, suitably in the form of a user-interface in/on the bladder monitor, such as one or more buttons (suitably a different button for each event) or a touchscreen with relevant user-interface/display. In another embodiment, a device remote from the bladder monitor (not necessarily in communication with the bladder monitor, so long as the device is operable to communicate with some part of the pre-void alert system, e.g. the data processor) may comprise part or all of the event data collection facility—e.g. a purpose-built event data collector device, or a personal computing device, such as a smartphone, tablet. In another embodiment, part or all of the event data collection facility is an automated event detection device. Such an automated event detection device is suitably configured to detect one or more events and transmit the event data to the appropriate part of the pre-void alert system for processing. An automated event detection device may, for example, include a moisture sensor (as per any of the currently-available nocturnal enuresis alarm systems) to detect a voiding event. Such automated event detection device(s) may be independent from the bladder monitor or integrated therewith. The system can suitably train itself using such voiding events to specify a new alarm threshold value customised or tuned to an individual patient's bladder liquid volume trigger point. This more accurate warning system, which stretches the warning threshold value to the point of voiding, can help the patients to alter their behaviours over time, reducing the frequency of nocturnal enuresis along with alerting at a better time before involuntary voiding Extracting information from the event data is relatively straightforward, since the data is typically collected as an array of specific data fields as described above.

The extracted information may constitute event data (or a part thereof).

Correlating Bladder Data or Bladder Information with a Bladder Status

The embodiments described herein illustrate how bladder data may be correlated to a bladder status. It will be self-evident to the skilled addressee which features or combination of features may or may not be included in such correlation methodologies.

In general bladder data is correlated with a bladder status (i.e. a bladder status is predicted from bladder data) through operating upon the bladder data (or part(s) thereof) with the status-mapping data and/or classifier(s) of the status-mapping data. The classifier(s) itself/themselves are suitably established as defined herein, suitably via a programme of training and testing. Operating upon the bladder data with the status-mapping data suitably involves operating upon the bladder data, or selected part(s) thereof, with one or more classifier(s). Where on classifier is used, this classifier suitably predicts the bladder status directly from the bladder data fed thereto. Where two or more classifiers are involved, each classifier produces a distinct bladder status opinion, and the opinions are aggregated to generate the final bladder status. Aggregation of the opinions suitably involves average or majority voting, though certain opinions may be judiciously weighted (e.g. on the basis of the accuracy, or other validated parameter—e.g. the more accurate the classifier, the higher the weighting for a particular classifier) thus leading to a bladder status represented by the weighted average or weighted majority of the plurality of opinions.

Triggering Alerts

After generating each bladder status, the pre-void alert system is suitably configured to compare the generated bladder status to a pre-determined trigger criteria. The trigger criteria is suitably a pre-determined bladder status classification (e.g. ¾ full), most suitably a bladder status classification which correlates with a likely urge to void. The trigger criteria may be set differently for different subjects, though suitably the trigger criteria is establish to permit the triggering of an alert before the subject is likely to void but at a level/classification at which the subject is likely to be able to void voluntarily.

The data processor suitably implements the comparison between the generated bladder status and the pre-determined trigger criteria. Suitably, where the comparison reveals (at least for the first time in a given voiding cycle) that the trigger criteria is met by the bladder status, an alert signal is issued (suitably a distinctive signal which is transmitted in a wired or wireless fashion, most suitably wirelessly). Suitably, the pre-void alert system comprises one or more alert devices (or alarm generators). Such alert devices are suitably configured to detect/receive the aforementioned alert signal and respond by producing an alarm signal. The alarm signal is suitably a signal that can be sensed by an animal or human, and may suitably be sensed during sleep so as to cause the animal or human subject to become conscious. The alarm signal may be an audible (i.e. alarm sound, suitably issued through a speaker or such like, such as a sound which gets gradually louder to ease the subject out of sleep), visible (light, e.g. bright flashing light or a light that gradually increases in intensity), tangible (e.g. vibration, such as a vibrating wrist band or head band), or olfactible (issues a smell) alarm signal, or may be speech generated from a defined text (i.e. text-to-speech processing).

Suitably the alarm signals can be manually terminated by the user, for example, by pressing a button. Such termination may be temporary, such as "snooze" features on regular alarm clocks. Such snoozing features may in fact be helpful during the pre-void alert system training process to stretch the algorithms to the point of voiding.

The process of triggering alerts may be controlled in a variety of ways for optimal comfort of the subject in question.

Suitably, once a first alert has been triggered, the alert process may override repeated attempts by the data processor to re-trigger an alert in response to repeated positive comparisons between real-time bladder statuses (which may or may not continue to be generated after a first alert trigger) and trigger criteria. In some embodiments, bladder status/trigger criteria comparisons may be temporarily suspended (e.g. until voiding has occurred, which may be duly reported to the pre-void alert system either manually or automatically as described in relation to the collection of event data) after a first alert trigger, since such comparisons will inevitably yield a result that the criteria is met. This reduces computer processing. Likewise, in some embodiments, generation of bladder statuses may be temporarily suspended to preserve processing power, though during pre-void alert system training it may be desirable to continue to collect this data for use in training datasets. Likewise, in some embodiments, collection of bladder data from the bladder monitor may be temporarily suspended (suitably based on PETI automatically determined by the system), since this can again reduce power consumption, which may be especially important for the bladder monitor where it is battery powered, and may suitably thereby improve safety through a reduction in pulses directed into the body. In all cases, suitably such data collection and processing may be recommenced at appropriate time (e.g. after voiding).

Individual Software

The pre-void alert systems of the invention may suitably operate pursuant to various individual computer programs, each encoded by corresponding computer software. Some or all of such individual computer programs and computer software may, in some cases, be combined. However, it may be advantageous to segregate certain processes from others. For instance, real-time operation of the pre-void alert system involving the collection of bladder data (and optionally also event data or at least voiding feedback data to reset alert triggers and reactivate any temporarily suspended processes), generation of bladder statuses, generation of alert triggers in response to bladder statuses meeting pre-determined trigger criteria, is suitably implemented by specific operational computer software that is distinct from training computer software encoding computer-implementation of a method of training/machine learning. In fact, it may be desirable for the training/machine learning process to take place on a data processor outside of the pre-void alert system, since such training may involve consumption of significant processing power. Under such circumstances, suitably the pre-void alert system is equipped with a means of transmitting relevant training data to a data processor carrying out the method of training, or alternatively the training data processor is equipped with a means of retrieving training data from data storage associated with the pre-void alert system (e.g. by a wired or wireless link).

The operational computer software may itself comprise one or more pieces of software which may run asynchronously or synchronously. In an embodiment, the operational computer software comprises software encoding computer-implementation of control features, such as:

operating (optionally remotely) the bladder monitor to collect (and optionally filter) bladder data according to a particular program (e.g. pre-determined pulse rates of ultrasound of pre-determined frequency and intensity);

operating (optionally remotely) the bladder monitor or other device to collect and record event data;

time-stamping;

controlling the movement of bladder data within the system (e.g. wireless transmission of bladder data from a bladder monitor to a separate data processor);

controlling alert triggers and the transmission of alert signals;

(temporary) suspension of certain operations, for example, in response to a first alert trigger; and/or Reactivation of suspended functions.

The operational computer software may additionally comprise software encoding data processing, such as the generation of bladder statuses from bladder data and/or comparison of bladder statuses with trigger criteria.

Applications

Pre-void alert systems and methods of the invention are applicable in a variety of fields, including but not limited to medical fields, veterinary fields, pets, and even chemical engineering fields (e.g. the system may be used to monitor and control the filling of vessels).

In a particular embodiment, the pre-void alert system is for treating urinary incontinence or a specific form thereof, such as nocturnal enuresis.

In the case of nocturnal enuresis patients, the pre-void alert systems of the invention may be used as a means of training the patient to awake prior to a void—this might ultimately cure the condition. Moreover, such patient training is a non-invasive method of training which avoids the indignity, trauma, and stigma of regular bedwetting. In some cases, the pre-void alert system may just provide a method of managing nocturnal enuresis in a manner which helps patient and carers alike by reducing mess.

Elderly patients and stroke victims are also vulnerable to urinary incontinence and can benefit from using the systems and methods of the invention. For instance, a common problem in care homes is the effective management of residents'/patients' toilet breaks, especially where such patients are infirm or disabled and require supervision. The systems of the invention may provide a system that allows for active monitoring of patients and active deployment of human resources in a timely manner to facilitate the efficient running of a care home.

The systems and methods of the invention also have veterinary applications, since urinary incontinence is a common problem in animals and pets, especially young pets that are not yet toilet trained, or older pets who have lost a degree of control of their bladder function.

Specific Embodiments

Exemplary embodiments of the present invention will be discussed in detail in relation to a bladder status estimating system, and associated nocturnal enuresis alert system, for non-invasively monitoring and alerting a person at risk of urinary incontinence or uncontrolled voiding. However, the teachings, principles and techniques of the present invention are also applicable in other exemplary embodiments. For example, embodiments of the present invention are also applicable to other estimating and alert systems which, for instance, monitor the bladder status of a dog and alert the dog carer to an imminent voiding event prior to the event itself so that the dog carer can take appropriate action.

Figure 1:
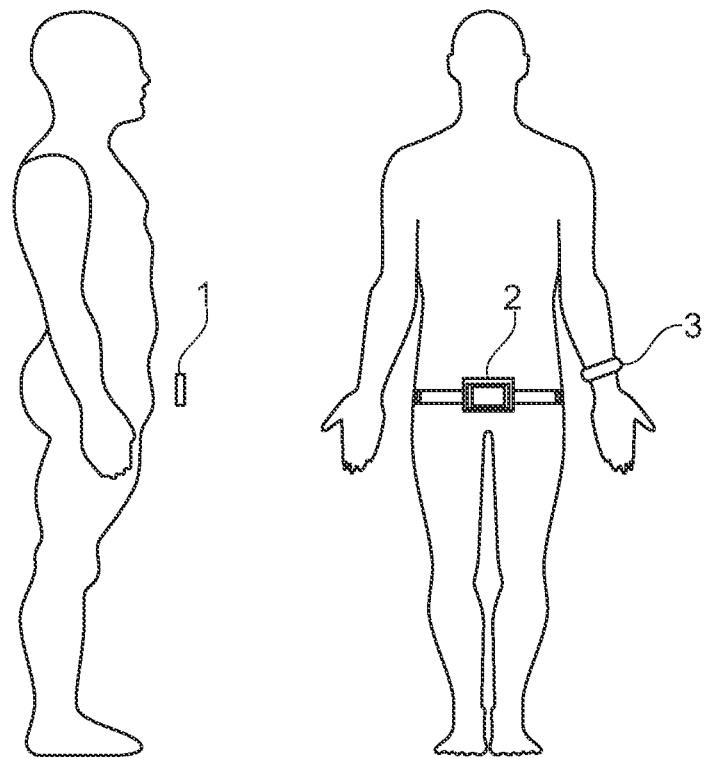
FIG. 1 shows an embodiment of an in-use bladder status estimating system, which in this case includes various remote devices.
Figure 1:
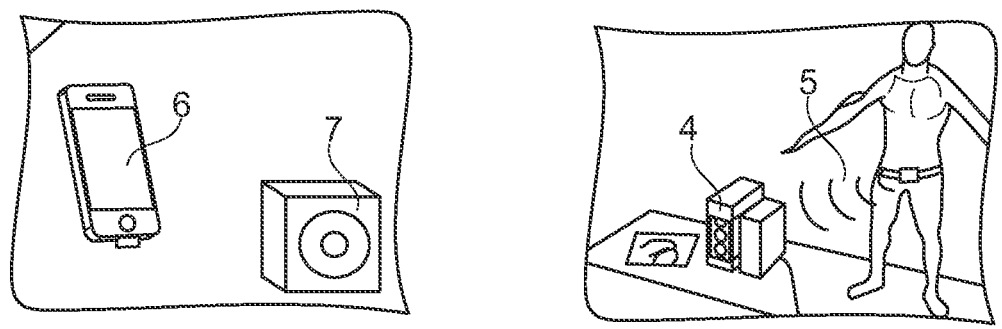

FIG. 1 shows an embodiment of a pre-void alert system. The system has a battery-powered bladder monitor 1 to be worn by a nocturnal enuresis patient, in this example via a mounting strap 2. In this example, the patient additionally wears a battery-powered vibrating wrist band 3 which vibrates in response to an appropriate trigger. The system additionally includes a remote data-processor 4, in this case a PC computer 4, which wirelessly communicates (e.g. via "Bluetooth") with the bladder monitor 1 via the relevant wireless transceivers incorporated into each of the bladder monitor 1 and computer 4. In certain sub-embodiments the system additionally includes a wirelessly-communicating smart-phone 6 running pursuant to a computer program (or "app") enabling the patient to record certain events, for instance, food/drink intake and voiding times. The system also includes an additional remote speaker 7 (suitably wirelessly connected to the computer 4) for issuing audio alerts (e.g. to the patient if placed by the patient's bedside).

Figure 2:
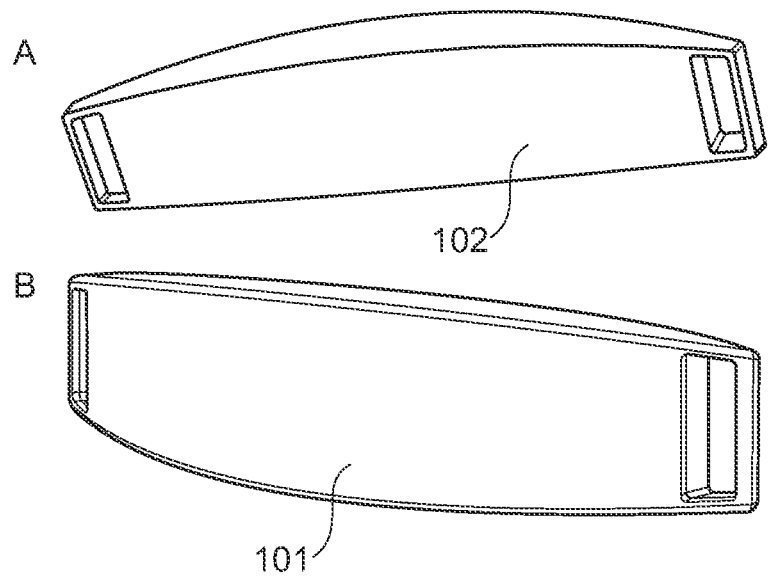
FIG. 2 shows rear (A) and front (B) views of an embodiment of a bladder monitor housing with a particular curved profile.

FIG. 2 further illustrates an embodiment of the bladder monitor's 1 housing, which suitably contains internal components allowing the bladder monitor 1 to perform its function. The housing may be made of any suitable material, though most suitably it is made of a material that is generally non-irritating to skin. FIG. 2A shows a rear view of the housing 1 (i.e. the side intended to face the wearer's body) with a concave rear face 102, whereas FIG. 2B shows a front view of the housing 1 (i.e. the side intended to face away from the wearer's body) with a convex front face 102. Both FIGS. 2A and 2B show the housing with two peripheral strap holes to allow the bladder monitor 1 to be worn by the patient via a mounting strap 2. The concave profile of the rear face 102 provides comfort to the wearer of the bladder monitor 1 and enables the monitor to be worn more discretely. The concave rear face 102 suitably has a curvature that generally complements the curvature of the wearer's abdomen (or lower abdomen).

Figure 3:
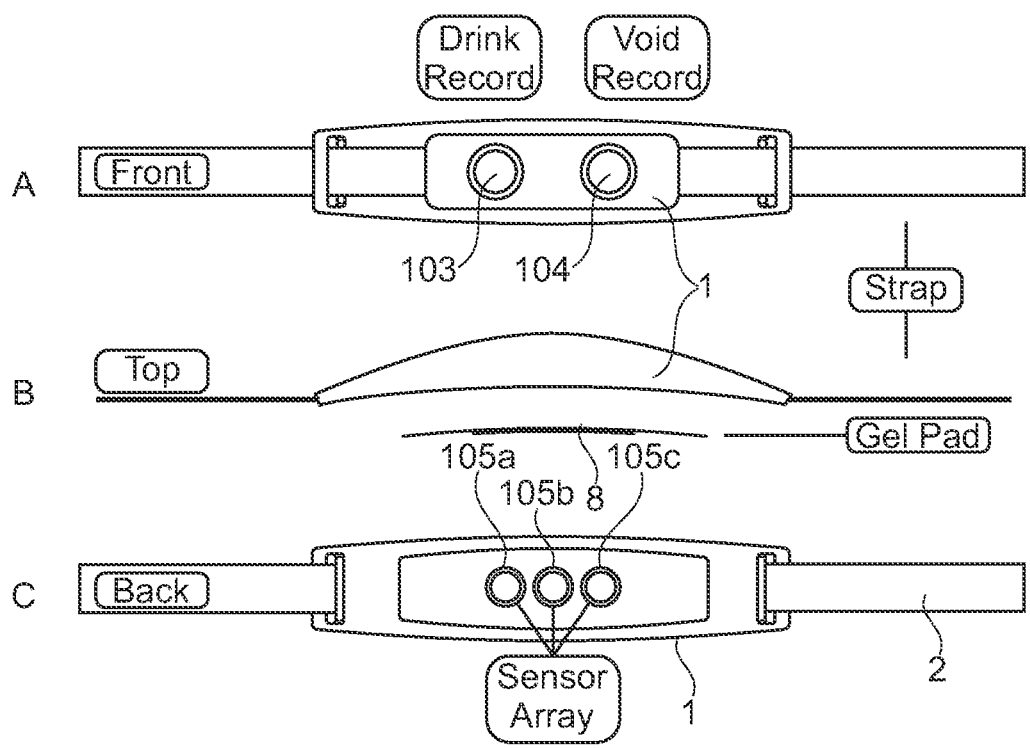
FIG. 3 shows front (A), overhead plan (B), and rear views (C) of an embodiment of a real-time bladder monitor, along with associated controls and sensors.

FIG. 3 shows an embodiment of the bladder monitor 1 associated with a mounting strap 2. Though alternative methods of wearing the bladder monitor 1 may be used, a mounting strap 2 can be used to comfortably strap the bladder monitor 1 to the patient in a correct position. Any suitable strap may be used, though the strap 2 is suitably formed of a material which balances the requirements for firm mounting and the wearer's comfort. As such, an appropriate degree of elasticity may be desirable so long as the firmness of the mounting is not compromised.

FIG. 3A shows a front face 101 of the bladder monitor 1 sporting two manually operable buttons which allow the wearer to record various bladder-related events which may facilitate machine learning within the pre-void alert system to better optimise overall performance and accuracy. In this case, the buttons include a drink-intake button 103 (which is pressed by the patient to record the intake of a drink) and a void button 104 (which is pressed by the patient to record a bladder voiding event). When each button is pressed, a recorded event is time-stamped and transmitted to the data processor 4 which logs the relevant event(s) for use in the later refinement of status-mapping data. It will be understood that such bladder-related event recordals may be achieved in a variety of other ways, whether manual (e.g. using a smartphone 6) or automatic (e.g. using additional moisture sensors associated with the overall system).

FIG. 3B shows a top plan view of the bladder monitor 1, illustrating how the concave rear face 102 rests against the wearer's body (e.g. lower abdomen) or, as in this example, sandwiches a skin-interfacing device 8 (e.g. gel pad) between the rear face 102 and the wearer's skin. In this example, the gel pad 8 is an absorbent pad (e.g. cotton wool) impregnated with ultrasound gel such that, when the absorbent pad is compressed between the rear face 102 of the bladder monitor 1 and the patient's skin, the ultrasound gel absorbed therein leaches from both sides of the pad to thereby facilitate enhanced contact between the rear face 102 of the monitor 1 (and relevant sensors associated therewith) and patient's skin. Absorbent pads (which suitably alleviate discomfort associated with the use of liquid ultrasound gel) are suitably provided as a separate element for installation by the patient or carer during mounting of the bladder monitor 1 to the patient. Prior to use the absorbent pads are suitably provided as an absorbent core impregnated with ultrasound gel with a removable backing sheet on either side of the absorbent core to retain the gel therein until use, at which point the backing sheets may be removed. Such absorbent pads may be stored in a sealed package to prevent premature drying and to preserve the gel.

FIG. 3C illustrates a rear view of the bladder monitor 1 and shows the side of the bladder monitor 1 that faces inwards when warn (i.e. the rear face 102). The rear face 102 exposes three low-power ultrasound transducers operable to transmit ultrasonic pulses and receive ultrasonic echoes. In this example, the ultrasound transducers are the means by which real-time bladder data is acquired to enable determination of a bladder status (e.g. the urine content and/or likelihood of voiding within a given timeframe).

Figure 4:
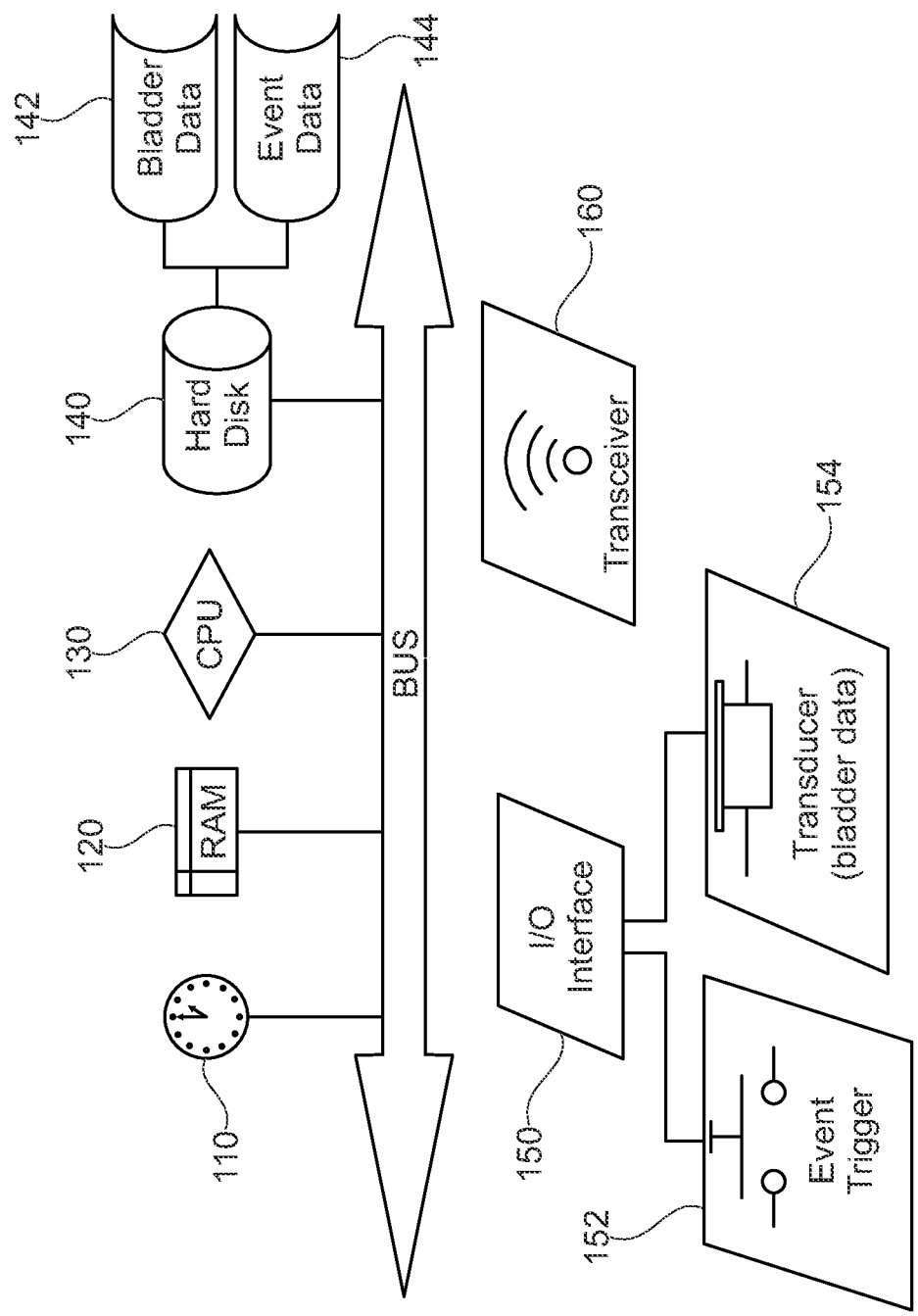
FIG. 4 shows a schematic representation of an embodiment of a bladder monitor.

FIG. 4 is a schematic diagram showing in more detail the internal components of the bladder monitor 1. Interfaced with a central BUS is a clock 110 (to enable time-stamping), a volatile memory 120 (which in this examples is a form of random access memory—RAM), a central processing unit (CPU) 130 (operable to execute instructions that are stored within the RAM), non-volatile data storage 140 (in this case a local hard disk for logging incoming bladder data 142 and, where applicable, bladder-related event data 144 stored therein), a wireless transceiver 160 (for transmitting bladder data 142 and, where relevant, event data 144 to a remote data processor 4), and an I/O interface 150 for controlling and receiving data from an ultrasound transducer 154 (for transmitting and receiving ultrasound signals to and from the patient's bladder), in this embodiment an array of three ultrasound transducers 154a, b, c, and an event trigger 152 (for collecting and/or receiving data regarding bladder-related events).

Figure 5:
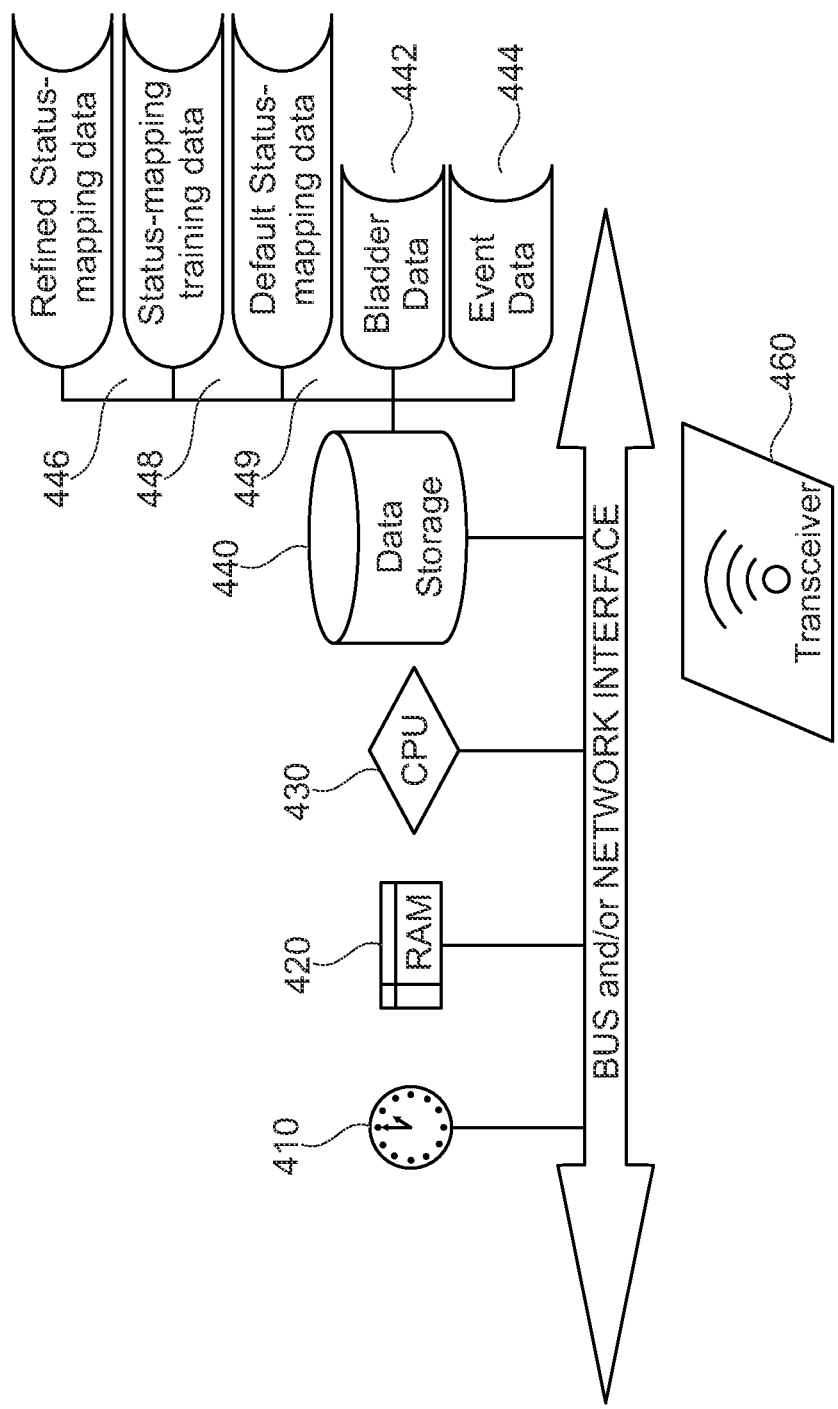
FIG. 5 shows a schematic representation of an embodiment of the bladder status estimating system's data-processor and data storage components which, in this case, are remote from but in wireless communication with a bladder monitor.

FIG. 5 is a schematic diagram showing in more detail the components of the data processor 4 unified by a BUS or a network interface (since any of the data storage components may be accessible remotely, for instance using internet protocols). Interfaced with the BUS or network interface is a clock 410 (for time-stamping), volatile memory 420 (in this case RAM), a CPU 430, non-volatile data storage 440 for storing bladder data 442, bladder-related event data 444, status-mapping data 446, status-mapping training data 448 (for use in training/testing predictive algorithms), and default status-mapping data 449, and a wireless transceiver 460 for receiving bladder data 142 and/or event data 144 from the bladder monitor 1 (or elsewhere) and, where appropriate, for transmitting alert signals to be received by external alarm devices (e.g. vibrating wrist band 3 and speaker 7).

It will be understood that various alternative arrangements can be deployed to achieve the aims of the invention. For instance, a "data processor" may include a plurality of (wirelessly or wired) interconnected data processors within the same overall system. Moreover, all functions of the data processor 4 may be implemented on a smart-phone 6 and/or with the bladder monitor 1 itself. Likewise, many of the functions of the bladder monitor 1 may be performed by a smart-phone 6 or similar such remote device, such as time-stamping, data-logging, bladder data filtering/normalisation, or co-ordination of the transmission of bladder data to another data processor 4. Data storage is another function which may be distributed or delegated amongst a plurality of (wirelessly or wired) interconnected devices which have or are connected to data storage.

It will be understood that embodiments of the bladder monitor 1 other than those depicted in FIGS. 3-4 may deploy alternative or additional bladder monitoring/scanning technologies (optionally in combination), such as audible sound; electromagnetic radiation, for example, light, infrared, and/or lasers; electrical properties (whether active or passive), for example, electromyography (EMG).

Figure 18:
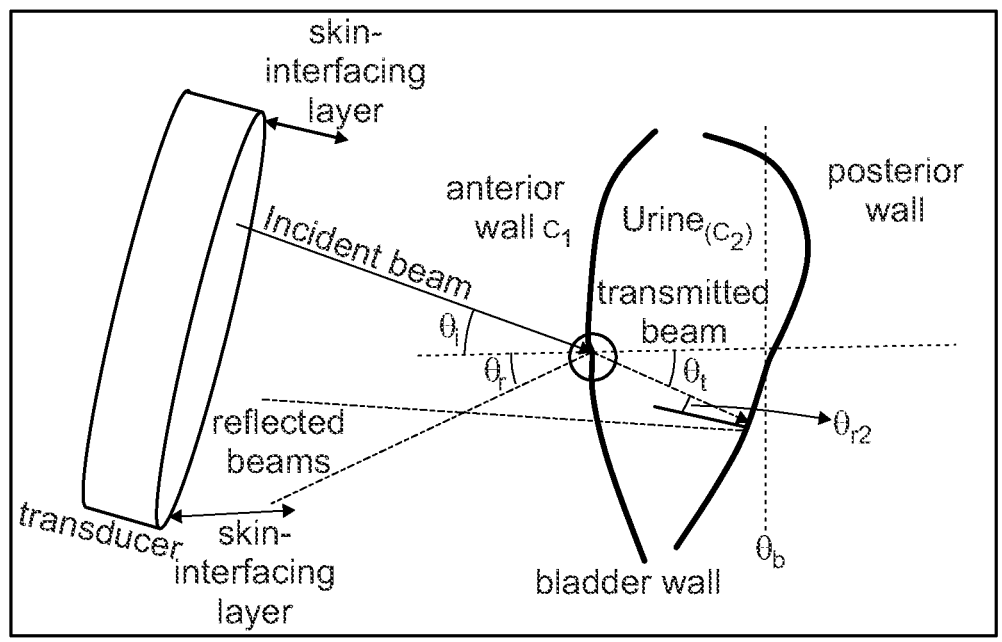
FIG. 18 illustrates the acquisition of attenuation echoed signals throughout the bladder with respect to incident beam, transmitted beam, and reflected beam.

However, ultrasound is particularly preferred following the inventors' discovery that attenuation signals from echoed ultrasound pulses can, when subjected to appropriate analysis, be used to provide highly accurate estimations of urine-bladder content and/or a likelihood of bladder-voids within a given timeframe. In particular, readily discernible time-domain attenuation signals from an anterior wall and a posterior wall of a bladder can provide extremely characteristic signatures for different bladder-urine contents. The inventors have also discovered that harmonics appearing in the attenuation signals arising from echoed ultrasound pulses can provide invaluable information to further facilitate such highly accurate estimations. The inventors furthermore serendipitously discovered that some or all of these ultrasound attributes are highly compatible with machine learning (ML) and dataset testing/training techniques which enable pre-void systems to rapidly learn, with minimal data input, to produce highly accurate bladder status estimations on the basis of ultrasound-derived bladder data. Additionally, the use of multiple sensors, capable of obtaining bladder data from multiple locations of the bladder (one of which is depicted in FIG. 18 in terms of the angles of the beams confronting the walls of the bladder), enables more accurate predictions to be made (which may be especially important since bladder shape may change, for instance, when the bladder monitor wearer changes position by simply rolling over in bed). Multiple sensors can also facilitate better self-calibration and reduce the level of preciseness required in initial bladder monitor placement.

Suitably the sensory technology(ies) utilised, such as ultrasound, are non-imaging sensors, since generally speaking the data obtainable from the sensors need not be translating into an image in order to provide the required information for making an accurate prediction of bladder status. The system need not use ultrasound to determine the actual shape and/or dimensions of the bladder itself in order to function, but may rather be used to determine intrinsic properties indicative of urine content or likelihood of voiding.

The embodiment of FIG. 3C utilises three horizontally-aligned and equally-spaced single-element transducers. The ultrasound transducer(s) transmits low power (0-3, suitably 0.03 W/cm$^2$) pulses of 2.25 MHz ultrasound waves at an appropriate pulse repetition frequency.

The pulse width used is 600 ns, though the device itself is tuneable to pulse widths between 50-600 ns. The propagation speed used is 1540 m/s, or 1.54 mm/μs, where:

Wavelength (mm)=Propagation Speed (mm/microsecond)/Frequency (MHz)

Thus the wavelength (mm) of the incident ultrasound was 0.7 mm.

The pulse repetition frequency (PRF) is 200 Hz.

The ultrasound transducers operate at 100V.

The same ultrasound transducer(s) receives echoed attenuation signals (from both anterior and posterior bladder walls) and thus has a dynamic range suitable for acquiring all relevant attenuation signals. Amplifiers may be used to boost attenuation signals if required. Moreover, noise reduction filters may be used to improve the signal-to-noise ratio for the relevant attenuation signals.

The amplitude of attenuation signals will differ depending inter alia on a person's age, sex, BMI, and such like, and suitably reflects a person's bladder size. By way of example, for a thin 6 year old boy, attenuation amplitudes echoed from the anterior wall of a bladder are generally at least 1.6 dB (even for an empty bladder), and at least 0 dB from the posterior wall depending on how full the bladder is. For a thin 10 year old boy, attenuation amplitudes echoed from the anterior wall of a bladder are generally at least 2.9 dB (even for an empty bladder), and at least 0 dB from the posterior wall depending on how full the bladder is.

Gain is applied to the attenuation signal, and in the present case the gain used was between 50 to 60.5 dB, with a gain of 50 dB being considered optimal to optimise the distinctiveness of the attenuation signals.

Time-domain attenuation signals (e.g. signal amplitude vs time), which give clear indications of the timings of certain events such as reflection (see FIG. 18), contain information regarding:

distances from the transducer(s) to each of the anterior and posterior bladder walls as well as the distance there between, which are calculated by:

$$d = \Delta t / 2c$$

where d is distance, $\Delta t$ is the time delay between two events (e.g. transmission and reflection), and c is the speed of sound (e.g. 1540 m/s)). An "event" such as a reflection from anterior and/or posterior walls is generally discernible from a time-domain attenuation signal trace (e.g. use of the gates at appropriate distances where the pulses indicate the important interfaces/features of the bladder regarding the amount of the urine within bladder), suitably by observing an "amplitude spike" (where a decaying attenuation signal is interrupted by a new signal with a higher amplitude than the previously-decayed signal), a momentary reduction in signal decay (also typically indicative of a new echo signal), a phase shift, or other such artefacts.

nature of the bladder wall and nature of bladder contents (e.g. urine, air, or only tissue), which may be established by:

establishing the contribution of acoustic impedance differentials (i.e. difference in acoustic impedances of two materials, e.g. urine and bladder wall, at a reflective boundary) at a reflecting interface (e.g. posterior bladder wall), suitably as shown in Table 3, to the overall intensity of the echoed attenuation signal;

intensity of echoed attenuation signals is related (and essentially proportional) to the difference (or mismatch) in acoustic impedances between two mediums from whose interface the attenuation signal is reflected. Urine can be detected by observing higher intensity signals because the acoustic impedance differential between urine and the bladder wall is significant enough to yield characteristic attenuation intensities.

establishing the contribution of acoustic scattering (e.g. at the anterior bladder wall) to the intensity of the echoed attenuation signal;

the scattering of propagation signals at the anterior bladder wall is highest when urine is absent (i.e. and air is present, see FIG. 20), and is minimal when urine is present (see FIG. 21), meaning that attenuation signal intensity is reduced to a much lesser degree (as a result of propagation signal scattering) when urine is present.

establishing the contribution of friction-like losses (arising through absorption) during propagation of the attenuation signal through relevant media (e.g. urine, air, tissue);

acoustic attenuation/loss arising from energy being absorbed by a propagation medium is minimised when urine, in comparison to air or just tissue, because urine has a particularly low acoustic attenuation coefficient (a).

The bladder data used to discern bladder status may include, yield, or be derived from any, some or all of the aforementioned pieces of information—in this example all are used.

Additionally, harmonic frequencies from attenuation signals may be used as a source of or to provide bladder data or information. Detectable harmonic frequencies are generally integer multiples of an incident frequency. Since the harmonics are generally of higher frequency, and since higher frequencies are more attenuated (due to greater acoustic losses) than lower frequencies, these harmonic signals are weaker than the parent frequency. The inventors have serendipitously discovered that such harmonics (particularly the first, second and third harmonics) are especially discernible where ultrasound waves propagate through urine. This is thought to be a consequence of greater "non-linearity" in the propagation of ultrasound waves through urine. Such harmonics can therefore be used to not only characterise the presence of urine, but also to identify propagation lengths through urine (more harmonics are observed for greater propagation distances). As such, bladder content/volume estimations may be discerned, estimated, or extrapolated from such harmonic data. Harmonic data may be represented in the frequency domain to extract relevant information (e.g. relative amplitudes of various harmonics may give an indication of wave propagation lengths).

Figure 33:
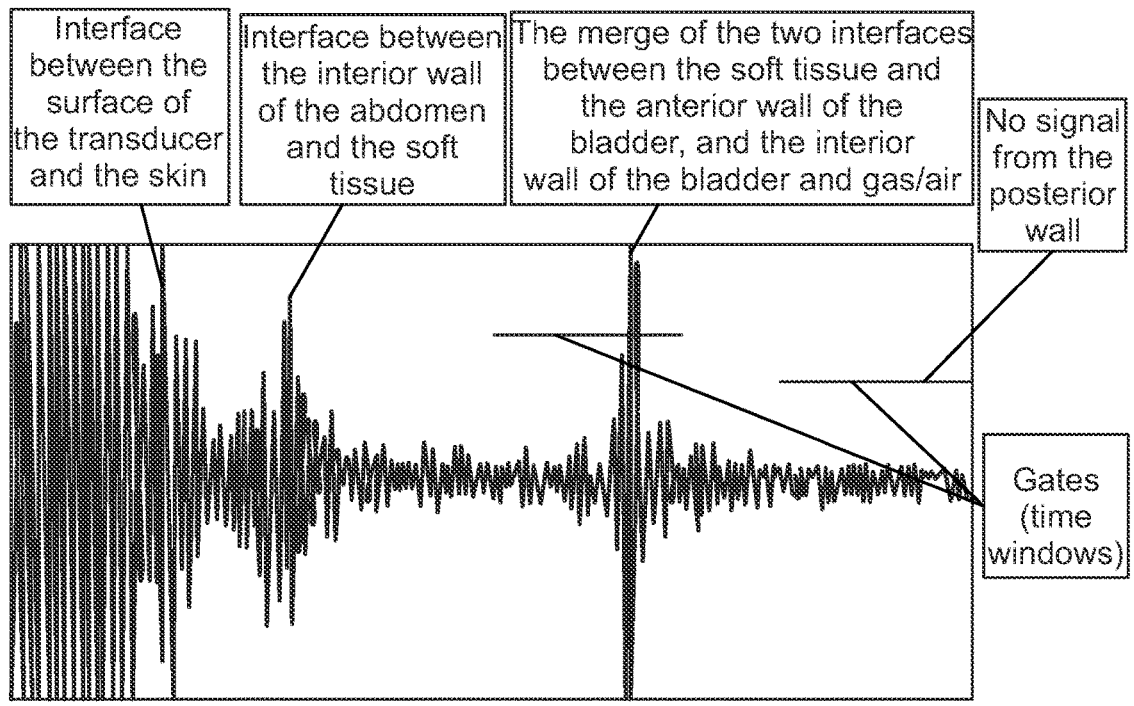
FIG. 33 shows an attenuation ultrasound signal trace obtained for a 6 year-old volunteer with an empty bladder.

FIG. 33 shows a reflected attenuation ultrasound signal trace obtained for a 6 year-old volunteer with an empty bladder. The signal from the anterior wall of the bladder is the mixture of the interface between the tissue and the exterior side of the anterior wall and the interface between the interior side of the anterior wall and the air/gas, the later one is much stronger in amplitude. The interface from the posterior wall is not obtained based on the air inside the bladder, resulting in no beams on the posterior wall. The interfaces detected on the gates can move forward and backward slightly as the person breaths. The total distance displayed after the interface between the transducer and abdomen is 150 mm for this example.

Figure 34:
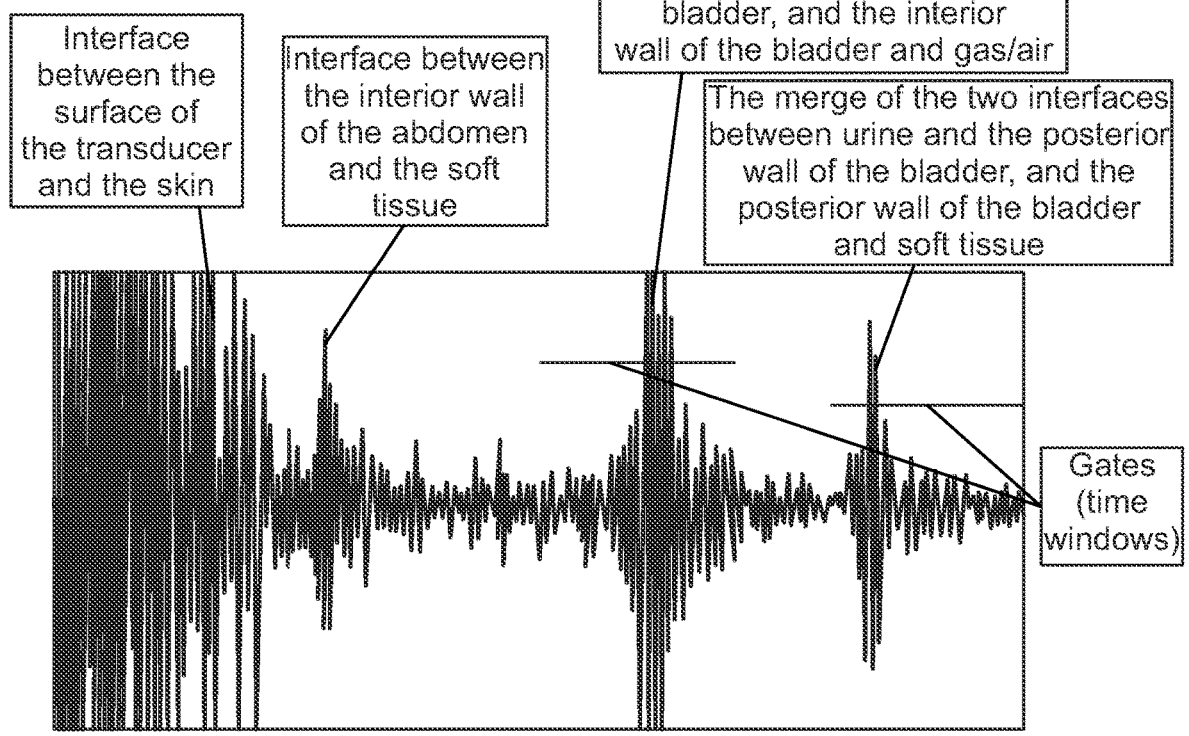
FIG. 34 shows an attenuation ultrasound signal trace obtained for a 6 year-old volunteer with a full bladder.

FIG. 34 shows a reflected attenuation ultrasound signal trace obtained for a 6 year-old volunteer with a full bladder. The interface from the anterior wall of the bladder is the merge of the interfaces between the tissue and the exterior side of the anterior wall of the bladder, and the interface between the interior side of the anterior wall of the bladder and the urine. The interface from the posterior wall of the bladder is the merge of the interface between the urine and interior side of the posterior wall and the interface of the exterior side of the posterior wall and tissue. The signals detected on the gates can move forward and backward slightly as the person breathe. The bladder starts to expand as the system detects signals from the posterior walls and consequently the distance between the signals at the first and second gates increases as the volume of the urine increases.

In this example, the attributes employed with regard to the interfaces at the gates (time windows) as shown in FIGS. 33 and 34 in bladder status assessments are as follows:

T(A): Time of flight: millisecond of an echo matching with the first gate (time window).

T(B): Time of flight: millisecond of an echo matching with the second gate (time window).

s(A): Distance from the transducer in mm of an echo matching with the first gate.

$$s(A) = \frac{1}{2} * T(B) * (US \text{ velocity}) \text{ where the } US \text{ velocity is between 1436 (for fat) and 1550 (for muscle) for human body based on the Body Mass Index (BMI).}$$

s(B): Distance from the transducer in mm of an echo matching with the second gate.

$s(A)=\frac{1}{2}*T(B)*(US \text{ velocity})$ where the US velocity is between 1436 (for fat) and 1550 (for muscle) for human body based on the Body Mass Index (BMI) until first signal, and 1551 (for urine) between the first and second signal.

$\Delta T = T(B) - T(A)$ $\Delta s = s(B) - s(A)$

H(A): Amplitude: % of A-Scan height of an echo matching with the first gate.
H(B): Amplitude: % of A-Scan height of an echo matching with the second gate.
V(A): Amplitude: db of an echo matching with the first gate with respect to a threshold.

$V(A) = 20*\log_{10}(H(A)/\text{threshold}A)$

V(B): Amplitude: db of an echo matching with the second gate with respect to a threshold.

$V(B) = 20*\log_{10}(H(B)/\text{threshold}B)$ $\Delta V = V(B) - V(A)$

Every HVT (see the Table 5) in a medium reduces the relative intensity by 3 dB.[6]

The values of harmonic waves (that may be detected using ultrasound) in the urine (especially the first harmonic and second harmonic, and suitably also the third harmonic) are considered to assess the volume of liquid, suitably along with other features described elsewhere herein.

The values of these attributes and the relationships there between along with the harmonic content in the echo result allows for an assessment of the volume of the urine in the bladder.

Urinary bladder temperature is a clinically reliable and acceptable method to measure core temperature of the body during medical operations as explained by many studies.[7] Urinary bladder temperature measurement is regarded as the most accurate means of core body temperature (CBT) measurement; Pubmed studies indicate the urinary bladder method as more reliable and accurate in comparison to the other modes of temperature measurement.[8] The thermal energy of the bladder typically changes as it fills with urine. Suitably the change in thermal energy acquired from the abdomen across bladder may be correlated with corresponding changes in thermal energy of the bladder, and thus abdominal thermal energy changes may be correlated with changes in bladder-urine volume/fill. As such, in embodiments of the invention, obtaining real-time bladder data may alternatively or additionally comprise detecting thermal energy changes. Thus corresponding apparatus may comprise one or more (preferably two) thermal sensors (i.e. infrared sensors) that can detect elevated body temperature based on the recent activities taking place in the body such as urine with a temperature flowing into the bladder. Suitably the or each thermal detector is incorporated into the bladder monitor (e.g. wearable belt), though in some embodiments the, each, or any thermal detector(s) may be part of a further external monitoring device. In a particular embodiment, the apparatus may comprise at least two thermal detectors, wherein at least two thermal detectors are located (suitably as part of the bladder monitor) or otherwise locatable to enable thermal measurements to be obtained non-invasively from at least two different parts of the body, for example: one thermal detector may be located/locatable to detect thermal energy from the abdomen (e.g. across the bladder) and another may be located at one side of the torso (suitably across abdominal cavity). The thermal energy in the urine consistently increases as the urine fills up the bladder which increases the thermal energy of the closely surrounding media and this energy is then reflected on the skin surface. The difference between the thermal measurements obtained from different thermal detectors may then be correlated to urine volume in the bladder. Suitably, the faster the flow of urine into the bladder, the greater the difference in the thermal energy measurements since bladder does not warm up the urine inside, but, the urine comes inside with a temperature of core warmth of the body. In other words, the thermal energy acquired from the bladder when it is empty is low when compared to the thermal energy obtained from the bladder when it is getting larger as the urine flows inside. The change of thermal energy of the bladder may be useful to determine the level of the urine within the bladder especially using a correlation thermal energy from the sides of the torso (e.g. from abdominal cavity) where the thermal energy does not change significantly. In this sense, the absolute change over time between the thermal energies acquired from the bladder and from abdominal cavity increases as the flow of the urine into the bladder increases which increases the thermal energy of the bladder whereas the thermal energy acquired from abdominal cavity retains static.

Suitably real-time bladder data may comprise (suitably in addition to other forms of bladder data defined elsewhere herein) at least two distinct real-time thermal energy measurements. Suitably a first thermal energy measurement relates to a part of the body whose thermal energy changes (in a manner detectable by a corresponding thermal detector) with bladder-urine volume, whereas a second thermal energy measurement relates to a part of the body whose thermal energy does not (substantially) change or changes to a lesser degree than the first thermal energy measurement with bladder-urine volume. The second thermal energy measurement may thus provide a control measurement with which the first measurement may be compared in order to determine a thermal energy gradient that may be correlated to bladder volume. No form of waves is transmitted to the body with this method.

The bladder data itself may include raw bladder data (e.g. time domain attenuation signals), especially in the first instance prior to filtering and/or aggregation to produce more meaningful data, and/or information discerned, estimated or extrapolated from the raw bladder data (such as information above). Different weightings may be ascribed to different pieces of information (and even different instances of raw bladder data) based on their ability to contribute to an accurate bladder status prediction—various quality control and/or cross-validation algorithms may be deployed to make such a weighting determination. For instance, bladder data artifacts (such as freak events that may be caused, for instance, by the bladder monitor wearer's movements, such as rolling over in bed) may be judiciously removed/discounted where they are deemed unrepresentative or representative of a discontinuity event. The skilled person can readily implement such artifact/error filtrations using routine workshop practice, for instance, through deploying standard statistical comparisons between an artifact and surrounding bladder data (e.g. bladder data collected soon before or soon after the artifact) or by comparison with established linear or non-linear regressions).

The aforementioned bladder data can therefore be used, in accordance with the invention, to estimate a bladder status on the basis of a comparison of non-linear wave distortion capabilities between a urine-loaded bladder (in conjunction with surrounding tissues) and an empty bladder (in conjunction with the same surrounding tissues).

The bladder data may itself be used in various ways—e.g. a) estimate emptiness; and/or b) estimate fullness. The data may be used for both purposes to obtain a more accurate result. For instance, data from the anterior bladder wall may be used to provide an indication of bladder emptiness, since when a bladder is empty there is little propagation of signals to the posterior wall and thus minimal attenuation signals receivable from the posterior wall. However, data from the anterior bladder wall yields little information regarding bladder fullness and instead data from the posterior bladder wall may be used to provide an indication of bladder fullness, as explained above—since the posterior wall attenuation signals will contain a significant amount of information acquired (e.g. accumulated harmonic signals) during propagation through any urine.

The bladder data may be used to estimate a bladder volume, which may then in turn be compared to an "expected bladder capacity" (EBC), which can be calculated on the basis of:

$$[(a+1)30=EBC(ml)]^{[4]}$$

where EBC is in ml, and a is the person's age in years.

However, in this embodiment, bladder status estimations take further advantage of status-mapping data, which can be customised and trained as described below.

The use of multiple ultrasound transducers, in this case 3 ultrasound transducers (e.g., the beams for one of which is illustrated in FIG. 18 in terms of the angles facing the walls of the bladder), allows for more effective self-recalibration if, for any reason, the bladder changes shape or location in a discontinuous or sudden manner (e.g. if a nocturnal enuresis patient rolls over during sleep, sits or stands). The use of multiple transducers adds another dimension to the predictive model to allow the "in-use" algorithms (selected form the status-mapping data) to be either changed or adapted (in accordance with a pre-trained model) in response to a discontinuous change in bladder shape and/or location detected by a sudden change in the comparative/relative attenuation signals of the set of transducers (each of which, by virtue of being in a slightly different position relative to the bladder, will be effected differently by any sudden chance in bladder shape/location). In this example, each of the multiple ultrasound transducers are identical, and transmit ultrasound signals of the same power/intensity, frequency, and pulse rate. However, it will be understood that offsetting any of the parameters of the ultrasound transducers may provide additional useful information.

More details regarding algorithms and mathematical operations are described in the Example/Data section below, where the principles of the invention are further elucidated.

Figure 6:
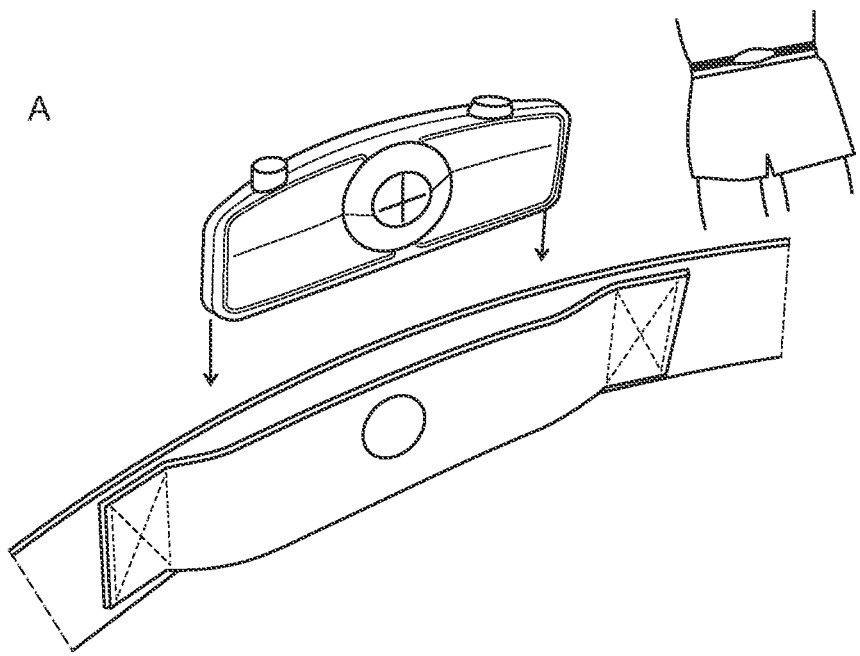
FIGS. 6 to 8 show various embodiments of a bladder monitor juxtaposed with various embodiments of a corresponding mounting strap.

FIG. 6 illustrates an embodiment of a mounting strap 2 incorporating a purpose-built pouch into which the bladder monitor 1 fits. The strap is designed much like a belt, and may be attached to the patient so as to locate the bladder monitor 1 in the correct place.

Figure 7:
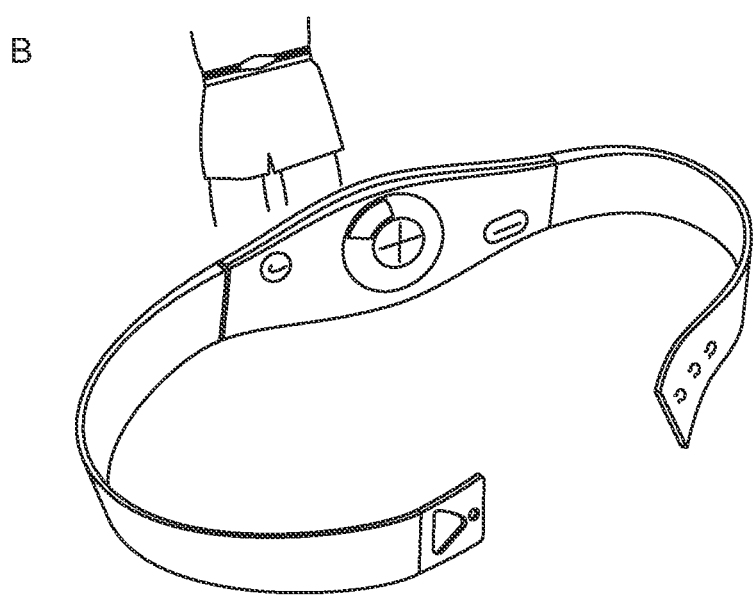

FIG. 7 illustrates an alternative embodiment of a mounting strap 2 which incorporates an integral bladder monitor 1. The strap 2 is shown with a buckle and buckle holes to enable the strap 2 to be fitted to the patient in much the same fashion as a standard belt. In this manner the bladder monitor 1 may be discretely fitted to a patient.

Figure 8:
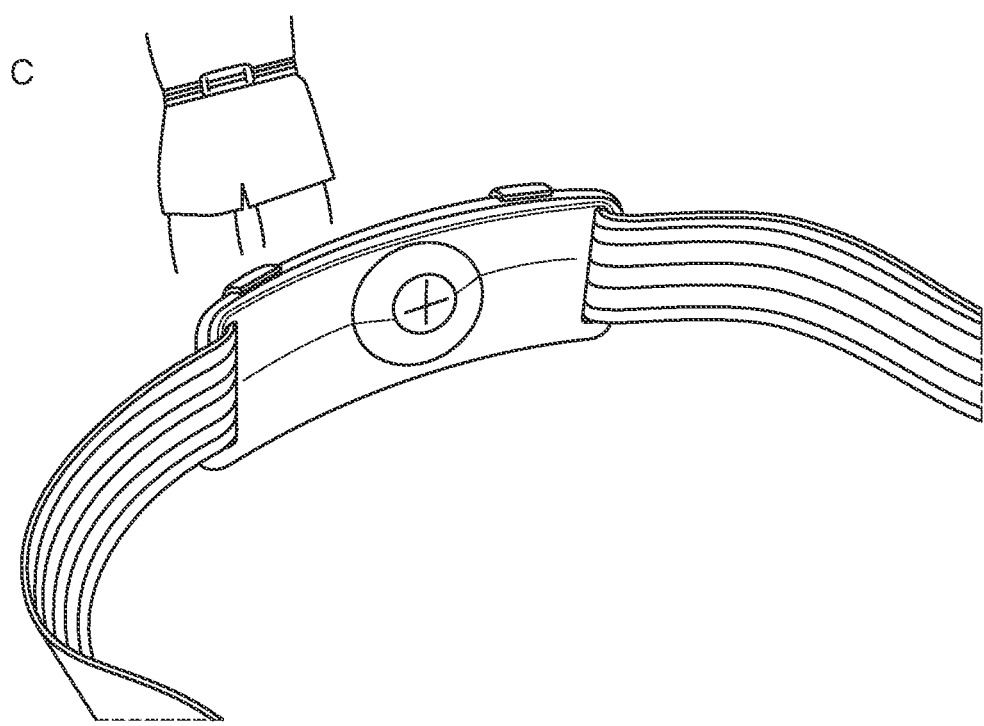

FIG. 8 illustrates a further embodiment of a bladder monitor 1 and its associated mounting strap 2. In this embodiment, the bladder monitor is equipped with strap holes through which the strap 2 is fed. The strap may then be secured to the patient with the bladder monitor 1 held firmly in place.

Figure 9:
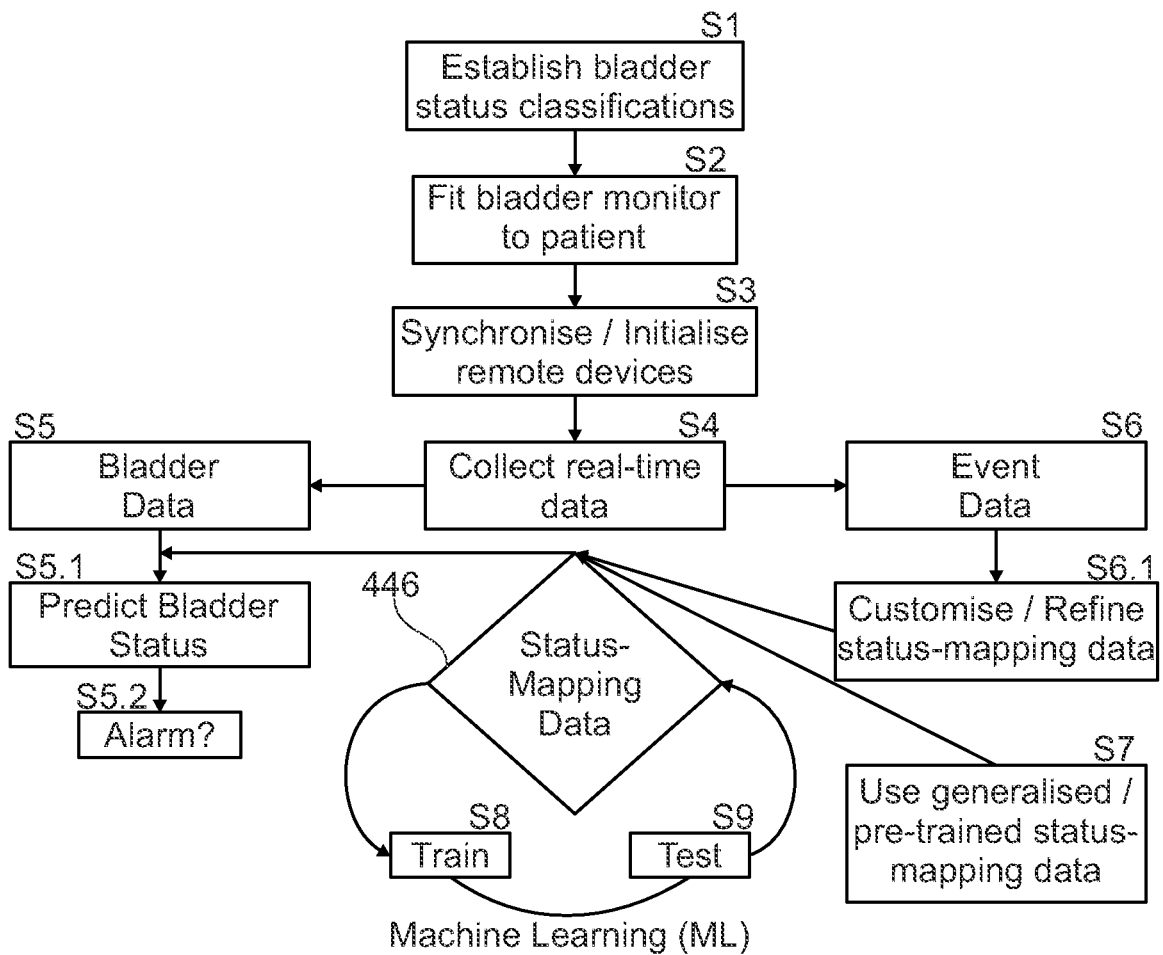
FIG. 9 is a flowchart illustrating an embodiment of a process of using a bladder status estimating system.

FIG. 9 shows, in more detail, an embodiment of a process which uses the pre-void alert system herein described.

In this example, the process first involves establishing bladder status classifications S1, which in this case are "empty" (1), "½ full" (2), "¾ full" (3), "full" (4)—4 classes in all. However, it will be appreciated than any number of alternative classifications may be used, including a sliding scale such as % bladder content (where 100% is full).

The bladder monitor 1 is then mounted to the patient S2 via the mounting strap 2 so that the rear face 102 of the bladder monitor 1, which exposes three ultrasound transducers 105a, 105b, 105c, interfaces with the patient's skin via the afore-mentioned gel pad 8 (with relevant backing sheets removed) which becomes compressed when the strap 2 is tightened to harness the bladder monitor 1 in the correct position above the bladder.

Once mounted, the bladder monitor 1 is synchronised S3 with all relevant remote devices, such as the wrist band 3, data processor 4, smartphone 6, speaker 7, and any remote (or network-interfaced) processing or data storage devices, and the remote devices are initialised, for instance, by validating and opening all relevant communication channels. This ensures that the system functions correctly before any real-time data is collected and analysed.

Following system initialisation S3, the bladder monitor 1 is activated to collect real-time bladder data S4/S5 and/or real-time event data S4/S6 (though event data may be collected via another means, such as a smartphone, which need not necessarily be in communication with the bladder monitor, though corresponding time-stamped bladder data and event data will eventually need to be combined for analysis). Such data collection may be triggered through remote instructions provided to the monitor (e.g. via wireless communication) from a smartphone 6 or another data processor 4, or may be triggered by the bladder monitor itself (e.g. a start button).

As illustrated in FIG. 9, after collecting the bladder data S4/S5, a bladder status prediction S5.1 is made, by reference to status-mapping data 446 (e.g. using one or more relevant algorithms), and an alarm if triggered S5.2 if the predicted bladder status is ¾ full or more.

As illustrated in FIG. 9, after collecting the event data S4/S6, such data can be used to customise and/or refine status-mapping data (e.g. algorithms) because time-stamped event data can be used to more accurately correlate correspondingly time-stamped bladder to a particular bladder status. As such, such well correlated bladder data-bladder status pairs may be used as a new training set, or as part of a larger training step, in further dataset training to produce more accurate prediction algorithms.

The status-mapping data 446 illustrated in FIG. 9 is used for making bladder status predictions from a given set of bladder data. As such, status-mapping data 446 includes one or more "classifiers", preferably support vector machine (SVM) classifiers produced via well-known SVM machine learning techniques. Such classifiers are usually in the form of algorithms, such as mathematical equations comprising pertinent input and output parameters (taken from raw or filtered bladder data) and/or conditional logic, but may also include datasets of pre-mapped pairs of bladder data and bladder statuses. In the present example, the status-mapping data 446 includes: an (SVM) classifier (preferably produced by sequential minimal optimization (SMO), Grid Search classifier, Linear Regression classifier and ensemble bagging classifier. Such classifiers are considered in more detail below, though they are well known in the art of computer science, albeit not applied to the present context where classifications are generally non-binary. Suffice to say, bladder data (such as attenuation patterns, intensities, harmonic patterns/intensities, etc.) can be mapped to a bladder status (e.g. using the aforementioned classifications) by passing key bladder data parameters through a trained classifier such as those mentioned above. Training S8 and testing S9 is discussed in more detail below. However, as illustrated in FIG. 9, generic status-mapping data S7 may be created for a patient based on the patient's age, gender, body mass index, and/or other parameters which are likely to affecting mapping of bladder data to a relevant bladder status. In the present example, the system first deploys generic status-mapping data based on pre-established status-mapping data corresponding to the patient's attributes (such generic status-mapping data can be imported from a central database into the system as status-mapping data 446 by selecting the correct generic status-mapping data for a given set of patient attributes) to allow for approximate initial bladder status predictions to be made whilst the classifiers of the status-mapping data are replaced or refined S6.1 through the use of event data collection and classifier retraining based on real bladder data for the patient concerned.

Figure 10:
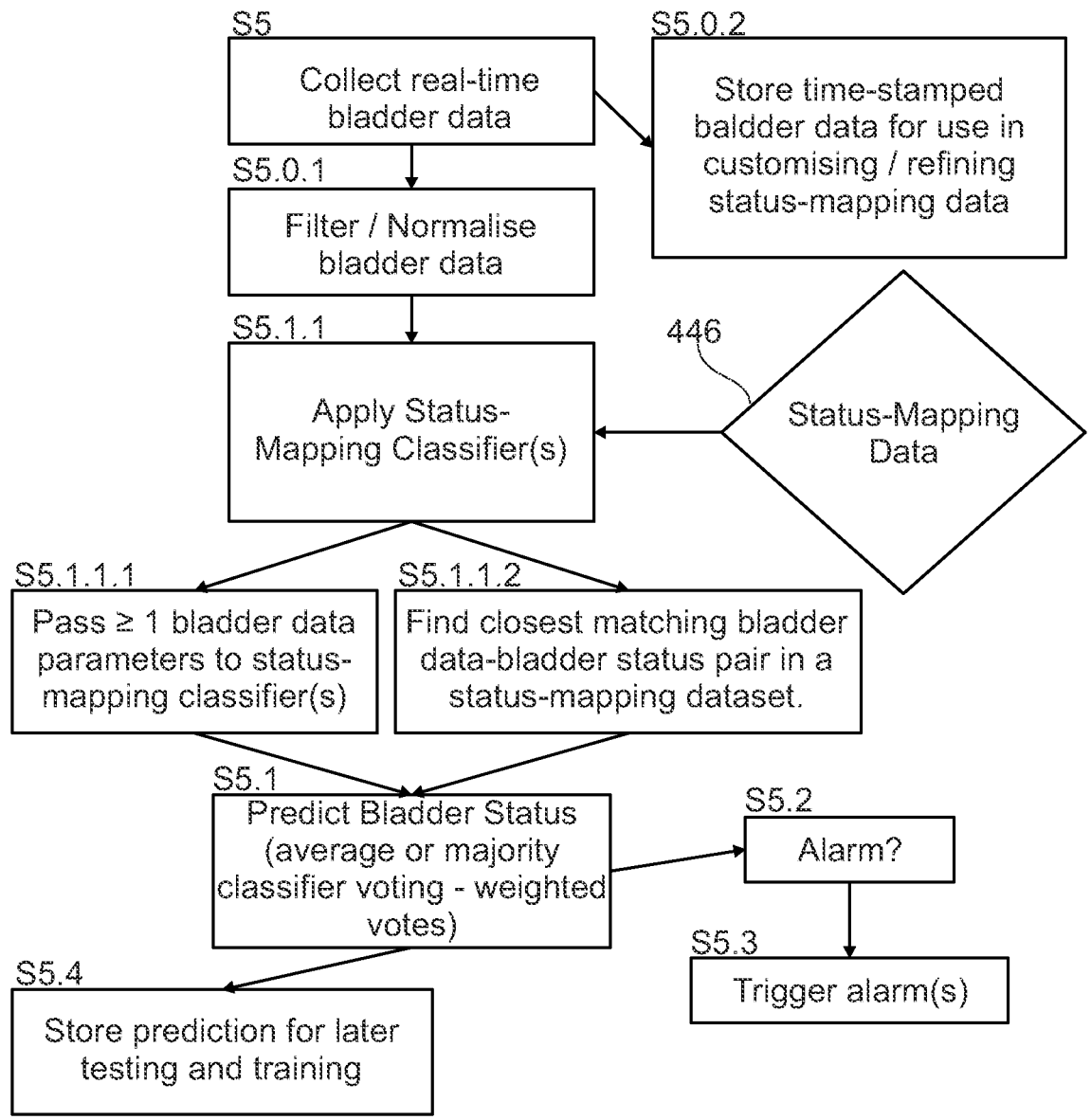
FIG. 10 is a flowchart illustrating an embodiment of the bladder data processing involved in the bladder status estimating system.

FIG. 10 shows, in more detail, an embodiment of the bladder status prediction process. After collecting real-time bladder data S5 from the patient, which in this example involves acquisition and subsequent transmission of ultrasound-based bladder data (from all three transducers 105, one of which is activated at a time) by the bladder monitor 1 to the data processor 4 via Bluetooth transceivers present in both devices. In this embodiment, the raw bladder data from each of the three ultrasound transducers are separately stored S5.0.2 in data storage associated with the data processor before each dataset is filtered and normalised S5.0.1. For example, noise reduction filters are used to improve the signal-to-noise ratio. Normalisation may involve normalising amplitudes of returning echoes (or at least an initial peak), regardless of depth, so that decay rates can be better compared and more informative. Though raw bladder data in the form of time-domain waveforms can be used in conjunction with appropriately-trained classifier algorithms, some classifier algorithms may require input parameters that are derived from the raw data, such as distance between anterior and posterior walls, distance ultrasound propagated through urine, (suitably for each transducer since this can provide more information on shape, location, and orientation of the bladder). Normalisation may involve normalising amplitudes of returning echoes (or at least an initial peak), regardless of depth, so that decay rates can be better compared and more informative. As such, the bladder data may be considered to comprise such derivative data as well as or instead of the raw data, depending on the classifier algorithms used. However, suitably the raw data is kept for further processing until it is no longer needed.

After the bladder data has been "sanitised" for use with status-mapping classifiers, the status-mapping classifiers are applied S5.1.1. The status-mapping classifiers are or are a part of the status-mapping data 446 accessible to the data processor 4. Applying the status-mapping classifiers S5.1.1, in the present case, involves applying a plurality of different classifiers. In the present example, applying the status-mapping classifiers involves apply an SVM classifier S5.1.1.1, a data grid search S5.1.1.2, a linear regression algorithm S5.1.1.1, and a bagging (or bootstrap aggregating) classifier S5.1.1.1. The output of such algorithms/classifiers is a bladder status/classification corresponding to the bladder data in question. As such, the process subsequently involves predicting the bladder status S5.1 on the basis of such algorithms.

Such predictions may serve as "test predictions" for later validation with collected event data and, as such, may be stored for later training and testing S5.4.

Next, the system determines whether or not to trigger an alarm based on the bladder status prediction S5.2. If the prediction satisfies a predetermined threshold criterion, in this case a ¾ full bladder, the data processor 4 suitably generates and issues an alert signal S5.3 (e.g. via a wireless transceiver) which, when received by a remote alert device such as the vibrating wrist band 3, smartphone 6, and/or bedside speaker 7, causes said alert devices to create an alarm signal, be it audible or inaudible (e.g. vibrations of the wrist band 3). The alert signal may also be received by a third party's (e.g. carer or relative) smartphone or similar such device to inform them to check the patient. Such a feature is also invaluable in alternative embodiments involving a pre-void alert system for pets, such as dogs.

In this manner, patients may be kept completely dry by enabling them to act in response to the pre-void alarm.

Though generic status-mapping data, acquired from a database to suit the specific patient's attributes (e.g. age, gender, BMI, etc.), can achieve excellent results, especially when such generic status-mapping data is already well trained based on large sample sizes of real data (not just that artificially generated) that has been accurately classified, such pre-void alert systems are particularly enhanced through an integrated training and testing system.

Figure 11:
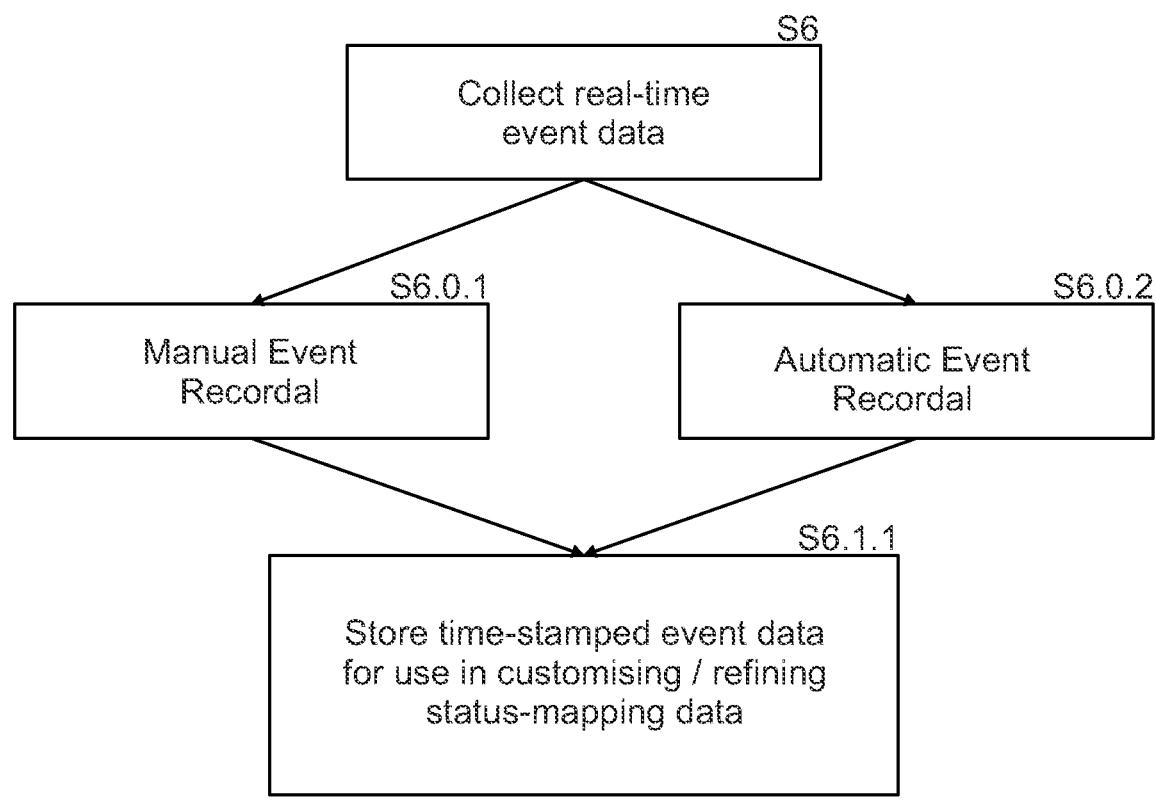
FIG. 11 is a flowchart illustrating an embodiment of the event data processing involving in the bladder status estimating system.

FIG. 11 illustrates an important part of such a training and testing system—the ability to collect and store time-stamped real-time event data. After collecting real-time event data S6, either by manual event recordal S6.0.1 as in the present embodiment (where buttons 103, 104 of the bladder monitor are pressed to record a time of drink/food consumption and a voiding time) and/or automatic event recordal 6.0.2 (e.g. using any of a number of well-known devices in the art, such as moisture sensors and the like), the event is categorised and stored with a corresponding time stamp so that the event may be correlated with nearby bladder data to assist in any algorithm training.

Figure 12:
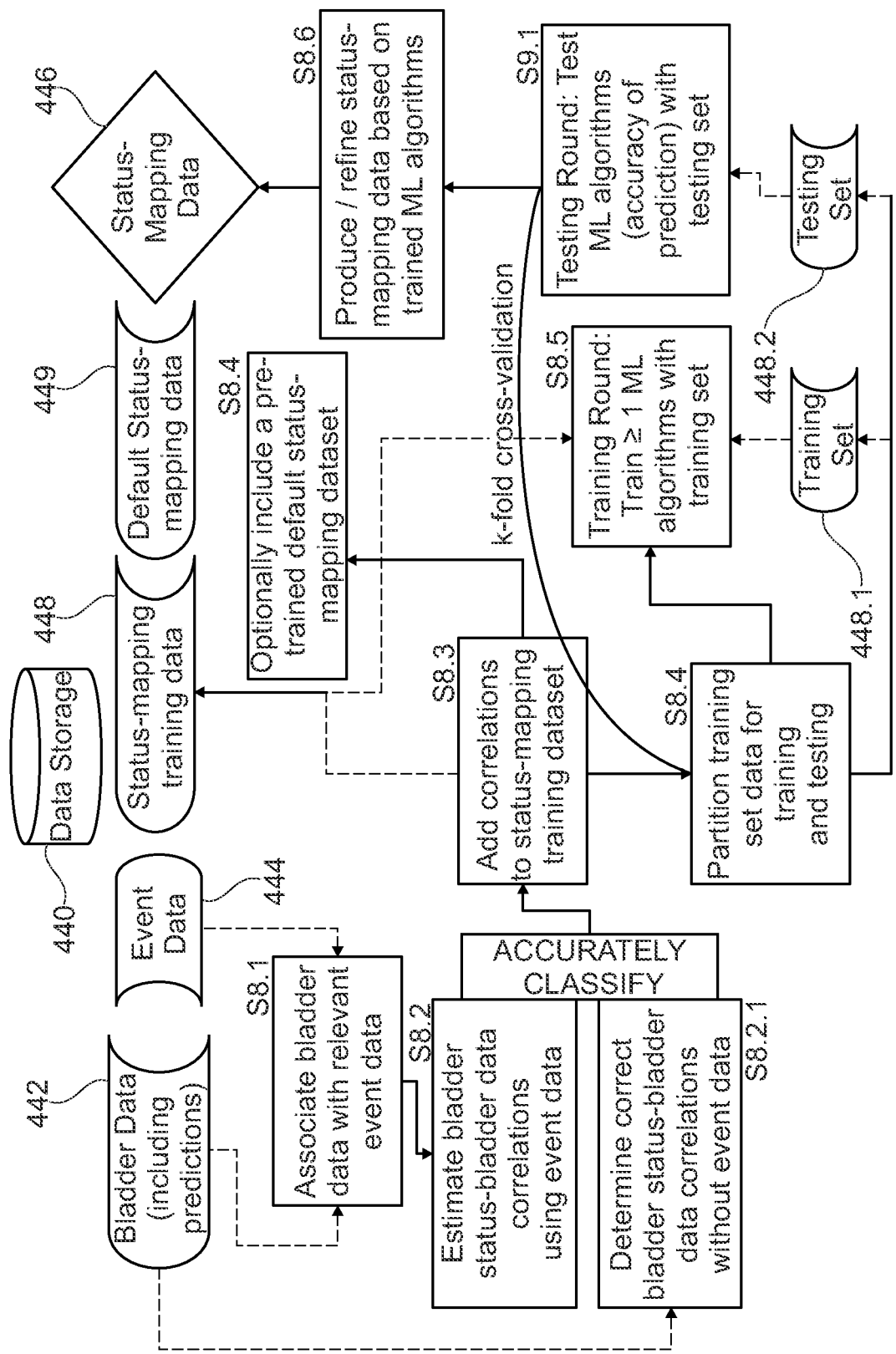
FIG. 12 is a schematic illustration of the data storage elements of the bladder status estimating system alongside a flowchart illustrating an embodiment of a status-mapping data training process for improving the accuracy of bladder status estimations.

FIG. 12 illustrates an embodiment of a training and testing process for use with the invention. The process involves reading and/or writing various data, such as bladder data 442, event data 444, status-mapping training data, default status-mapping data 449 (e.g. generic status mapping data and/or established customised status mapping data), and status-mapping data 446, to data storage 440, which may be an internal component of the data processor 4 and/or an accessible external component (e.g. data cloud or server).

In this illustration, the bladder data 442 and event data 444 has already been collected by one of the aforementioned methods and is now stored in data storage 440 ready for use. Likewise, any default status-mapping data or existing status-mapping data may be already established within the data store 440, albeit the training/testing system may replace or refine such data.

In some embodiments, the pre-collected bladder data 442 may be accurately classified without reference to any event data, for instance, through manual classification where the bladder status is known, or automated classification using another technique (e.g. bladder imaging). However, to avoid any requirement for manual input, the pre-void alert system may be provided with appropriate event data collection means to allow for automated classifier training. In this manner, a patient may begin by using the pre-void alert system on the basis of somewhat approximate status-mapping data (e.g. established from generic status-mapping data) but after a period of time collecting event data (e.g. 14 days) may reap the benefits of a more finely tuned customised system which recognises patient-specific bladder data patterns rather than more generic patterns.

As such, the process suitably involves associating collected time-stamped bladder data with collected time-stamped event data S8.1 before using the combination of data to estimate bladder status-bladder data correlations for each piece of bladder data S8.2. For example, where a voiding event is recorded by the patient at time x, a drinking event is recorded at time y, and another voiding event is recorded at time z, all intervening bladder data may be assigned a bladder status classification on this basis. For instance, the bladder data taken immediately after a voiding event may be reasonable classified as empty. Since the urge to urinate is generally recognised to occur at approximately ¾-full bladder by volume, it is reasonable to categorise bladder data occurring immediately before voiding in the ¾ full category. The intervening data may be classified in a number of ways: for example using a linear extrapolation, or using established bladder fill rate curves (especially where bladder volume is non-linear with time). Classifying interveners may involve using the maximum bladder volume which may be approximate for a given patient, as defined herein, based on age. Since accuracy is most important in the ¾ category, save for the bladder data immediately preceding this category classification of the other intervening bladder data is less import.

Once the event-data-driven bladder status estimations have been made S8.2, the correlated pairs of bladder data-bladder status are added to a status-mapping training dataset S8.3 for isolated training (i.e. with or without any other previously-established data) of classifiers. It will be understood that such training of classifiers may be performed using this status-mapping training data in isolation S8.3 (without any other previously-established data) or with a mixture of the new training data and some previously established data S8.4 (such as that which may already be part of the master status-mapping data, for instance for the grid searching algorithms).

Training of classifiers S8.5 is then performed upon the status-mapping training data 448. In this example, training is performed using 4 machine learning techniques to produce 4 types of bladder status classifiers.

Typically, the training of classifiers involve multiple training rounds on a given set of training data, interspersed with multiple rounds of testing S9.1 with a given set of test data. Typically, before commencing training for each particular classifier algorithm, the status-mapping training data 448 is split into a training set and a testing set (various ratios may be used). This division may remain throughout the testing, or may be revised (or iterated through, so that each data point has been the subject of training and testing) at each or some training rounds. The training set is then subject to training S8.5 to produce an intermediate classifier (which may be imperfect depending on the number of training rounds required and thus far carried out), before the testing data is tested S9.1 using the intermediate classifier. Such testing allows inter alia the classifier's accuracy to be determined, and optionally repeated training rounds may be performed (optionally shuffling or systematically modifying the training and testing sets) where insufficient accuracy is achieved. Such training/testing round may take the form of cross-validation techniques described herein.

Firstly, the status-mapping training data is used to train a support vector machine (SVM) classifier. This is performed using sequential minimal optimization (SMO), which is particularly applicable for the scale and nature of data involved. SMO addresses many performance problems associated with standard SVM training algorithms. By way of example, a binary classification problem with a hypothetical dataset $(x_1, y_1), \ldots, (x_n, y_n)$, with $x_i$ as an input vector corresponding to the binary label/classification $y_i \in \{-1, +1\}$ may be trained with a soft-margin SVM by solving a quadratic programming problem expressed in the dual form as[9]:

$$\max_{\alpha} \sum_{i=1}^{n} \alpha_i - \frac{1}{2}\sum_{i=1}^{n}\sum_{j=1}^{n} y_i y_j K(x_i, x_j)\alpha_i \alpha_j,$$

subject to:

$$0 \le \alpha_i \le C,$$

for $$i = 1, 2, \ldots, n,$$

$$\sum_{i=1}^{n} y_i \alpha_i = 0$$

where C is an SVM hyperparameter and $K(x_i, x_j)$ is the "kernel function" (both supplied by the user), and $\alpha_i$ are Lagrange multipliers.

SMO fragments this problem into a series of small sub-problems, which can be solved analytically (i.e. without significant processing power). For any two given multipliers $\alpha_1$ and $\alpha_2$, the aforementioned constraints are reduced to simply.[9]

$$0 \le \alpha_1, \alpha_2 \le C,$$

$$y_1\alpha_1 + y_2\alpha_2 = k,$$

and this reduced problem can be solved analytically by finding a minimum of a one-dimensional quadratic function. k is the negative of the sum over the rest of terms in the equality constraint, which is fixed in each iteration.

The SMO algorithm may be performed by[9]:
finding a Lagrange multiplier $\alpha_1$ that violates the Karush-Kuhn-Tucker (KKT) conditions for the optimization problem;
picking a second multiplier $\alpha_2$ and optimising the pair $(\alpha_1, \alpha_2)$;
repeating these two steps until convergence is achieved.

Once all the Lagrange multipliers satisfy the KKT conditions (within a user-defined tolerance), the problem has been solved. Heuristics may be used to accelerate the rate of convergence.

The same status-mapping training data is then used to train a linear regression (LR) classifier, such as those well known in the art.

The same status-mapping training data is then used to train a data grid search classifier. This involves finding a best bladder data-bladder status pair. An initial grid, containing an array of correlated bladder data-bladder status pairs, is suitably trained/tested using a 2-fold cross-validation (CV) (50:50 training set:testing set) to determine the best parameter pairs for CV accuracy (as opposed to other CV parameters). Taking the best point in the grid and then perform a 10-fold CV with adjacent parameter pairs, if a better pair is found then the new better pair can act as a new "centre" for further 10-fold CV training/testing rounds. This process may be repeated until no better pair is found, or the best pair is on a border of the grid.

Finally, the same status-mapping training data is then used to train a bagging as defined elsewhere herein. It will be understood that any machine learning classifiers may be deployed, in various combinations without departing from the spirit of the invention.

Once "trained up", the status-mapping data is suitably augmented or replaced by the one or more trained classifiers. Such new status-mapping data may be used in further or later rounds of training/testing if required.

Such training protocols may be implemented any number of times, though the inventors believe a highly effective pre-void alert system with minimal errors can be trained in fewer than 28 days, more suitably fewer than 20 days, more suitably fewer than or equal to 14 days. Suitably, minimal errors can be trained in fewer than 2 hours, suitably fewer than one hour, suitably fewer than 30 minutes.

Multiple classifiers may be used in a number of ways to predict a bladder status from an instance of bladder data. In this example, predicting the bladder status involves each of the four (suitably trained) classifiers operating upon the bladder data (from or derived from the same raw bladder data) to produce four distinct bladder status "opinions" (i.e. the bladder status according to the opinion of the particular classifier in question, which may or may not differ from the opinion of other classifiers), which distinct opinions are then expressed as equally-weighted votes so that a final aggregated classification (final bladder status) can be made on the basis of (weight-) average or majority voting. It will be understood that any number of a variety of different classifier algorithms may be used, and furthermore any subsequent voting may involve weighted votes where a each weighting (or coefficient) is a function of classifier performance (e.g. accuracy, sensitivity, etc. as determined by testing and cross-validations). In some circumstances, these weightings may vary in real-time depending on the circumstances. For instance, one particular classifier may be more accurate than another classifier in a certain situation (e.g. when a patient lies on their side) but less accurate in a different situation (e.g. when a patient lies on their back). Such weightings may take such factors into account where such factors are apparent in the raw or derived bladder data (e.g. multiple transducers allows for more information regarding orientation of the bladder and patient).

EXAMPLES/DATA/DISCUSSION

Described therebelow are various specific procedures, experiments computer models, and data to illustrate and further facilitate implementation of the invention. In particular, the discussion below illustrates the principles underlying bladder data analysis, classification, and the artificial intelligence/machine learning techniques used to train and test classifiers used to generate a real-time bladder status.

Materials and Equipment

C17 single-element transducer with a 2.25 MHz and an ISONIC utPOD ultrasonic pulse transceiver that can be connected to a computer via a USB port.

Two parallel processing applications (software) were developed in both C # and Java programming language to both train/test bladder datasets and to diagnose the status of the bladder correctly based on the instances of bladder data acquired from people suffering from the nocturnal enuresis.

The processing application can generate instances randomly mimicking the attenuation signals acquired from the anterior and posterior walls of the bladder and harmonics from the urine in the bladder using a single-element transducer for the four states of the bladder (i.e., empty, ½, ¾, and full). The system can be fed with newly-generated instances mimicking the real environment for establishing the state of the bladder throughout the trained classifiers. The application employs several machine learning (ML) algorithms on the data set using holdout, n-fold and leave-one-out cross-validation (CV) schemes depending on the number of the instances. The ML techniques that fit the data set best are sequential minimal optimization (SMO) for training a Support Vector Classifier, Grid Search, Linear Regression and ensemble bagging meta learning algorithms. A voting scheme based on the classification results of these algorithms is performed to decide on the current state of the bladder when new instances are introduced into the system.

Pre-void alert system implementation was tested on artificially generated data sets to explore the performance of the machine learning (ML) algorithms/classifiers employed. 10 general data sets (10*400=4000) were generated and the mean accuracy rate of the ML algorithms are measured using 10-fold cross-validation. The accuracy of the system is about 98% with a sensitivity value of 0.98 and a specificity value of 0.99 in terms of training the data set and constructing the classifiers using 400 instances for general data set generated artificially by the system, 100 for each state of the bladder. The algorithms are run in parallel processing by dividing code particles among multiple processors with the object of running these code particles in less time (i.e. reducing the computation time for training/diagnosis, particularly to run all classifier techniques at the same time on different processors) for constructing the classifiers for each of the four ML algorithms. Thus, the required time to establish the classifier for each data set (# of instances=400) ranges from 45 sec to 110 sec.

Development of Ultrasound Solution

An ultrasound probe generally comprises a head with piezo-electric crystals which, when stimulated by an electric current, shape swiftly to thereby initiate a sound wave. US waves have frequencies that exceed the upper limit for audible human hearing, i.e., greater than 20 kHz.[10]

The thicker the piezoelectric element (i.e., transducer material), the lower the frequency, and conversely, the thinner the element, the higher the frequency. Attenuation of the ultrasound increases with higher frequencies (e.g. in Table 5, notice the Half Value Thickness (HVT) values for 2 MHz and 5 MHz transducers) as the penetration of the ultrasound throughout the body reduces with small wavelengths (i.e., distance between two points on wave peaks, formula: $\lambda = c/f$ where c stands for velocity and f stands for frequency, note that the inverse relationship between $\lambda$ and f) (Table 1). Therefore, we employed single element transducers as a transmitter and receiver simultaneously with a low frequency of 2.2 MHz to allow a wider range of wavelength to go through longer distance as shown in Table 1 (notice the distance, 20 for 2 MHz). The wavelength for the soft tissue in our case: $\lambda = 1540/2.2*10^6 = 0.7$ mm where 1540 is the mean velocity of soft tissues. It is 0.652 and 0.705 for fat and urine respectively. The velocity of sound is measured using the following formula:

$$c = \sqrt{\frac{B}{p}}$$

where B is bulk module (stiffness) and p is density (kg/m³). We use a range of velocity values changing from 1436 and 1551 to measure the exact distances in accordance with the BMI and the body medium where the longitudinal signal travels in terms of the different velocity values in medium (e.g. in Table 4, notice the "sound velocity" column). Our area of interest is 20 cm which covers the whole bladder for the people with different BMI values. The gain that we perform on the detected signals changes (ranging from 50 to 60.5 dB) in terms of the BMI, which makes the signals distinctive from each other. The values of BMI range from 0 to 45 (from underweight to obese) and we reversely map this BMI interval into the gain interval to obtain a similar comparable attenuation signals at the wall of the bladder for each person where the fat in the abdomen impedes the transmission of ultrasonic energy. For instance, we employ a value of 50 for a BMI value of 45. This mapping needs to be evaluated after acquiring datasets from many people who have different BMI values in terms of the attenuation signals acquired from the walls of the bladder.

TABLE 1

Depth of penetration in the body in terms of the frequency of the employed transducer.

| | Frequency (MHz) | | | | | |
|---|---|---|---|---|---|---|
| | 1 | 2 | 3 | 5 | 10 | 20 |
| Depth of Penetration (cm) | 40 | 20 | 13 | 8 | 4 | 2 |

Mechanical (sonar) wave is defined as the systematic disturbance of the state of equilibrium in substance, such that the location of this disturbance in space has time-varying characteristics. They have several physical properties such as velocity (c) expressed as meter per second, angular frequency ($\omega$) expressed as Radian per second, spatial wave frequency (f) expressed as Hertz, wave amplitude (I) and wavelength ($\lambda$) expressed in meter. Reflection in sonar waves occurs when a mechanical wave encounter a boundary between two media with unequal acoustic impedance (Z). The greater the difference in Z values (i.e., acoustic mismatch) between two media, the more distinctive is the interface. In other words, the difference in Z values at the interface determines how big the value of the amplitude is. The acoustic impedance is denoted by Rayl (kg/(s·m²)) and is defined as[6]

$$Z = p \cdot c \quad (1)$$

where p is the density (kg/m³) of the medium, c is the velocity of the medium. Proper matching ($Z_1 - Z_2 \approx 0$) is preferable for the transmission of ultrasound wave from one medium to other with a very little loss without much reflection. First and foremost, we aimed to provide a proper matching for the transducer we employ for the bladder monitoring device. In other words, the Z value of the window of the transducer was almost the same Z value of the soft tissue, namely abdomen for the better transmission of the ultrasound beams emitted from the transducer. One of the best ways is to use the quarter-wave matching to determine the impedance value of matching layer with regard to piezoelectric element to minimize the reflection right in front of the transducer surface using the formula displayed below:

$$Z_{match} = \sqrt{Z_t * Z_{st}}$$

where $Z_t$ is the impedance value of the transducer and $Z_{st}$ is the impedance value of the soft tissue. For instance, a piezoelectric slab has a Z value of 30×10⁶ and a soft tissue (e.g., abdomen) has a Z value of 1.63×10⁶. In this case, the matching layer on the transducer should have a Z value of 7·10⁶ to minimize the mismatch as calculated below.

$$Z_{match} = \sqrt{Z_t * Z_{st}} = \sqrt{30 \times 10^6 * 1.63 \times 10^6} = 7 \cdot 10^6 \text{ rayls}$$

Some of the Z values related to the bladder and the surrounding mediums are displayed in Table 2. Note that the Z values of fat, water and muscle are so close to each other. At this point, we should mention about the reflection coefficient which is measured using the following formula, the reflection coefficient of the anterior wall is calculated, 0.05, as an example when there is urine within the bladder which means that %5 of the energy beam is reflected and remaining %95 travels into the urine:

$$R = \frac{P_r}{P_i} = \frac{Z_2 - Z_1}{Z_2 + Z_1} = \frac{1.64 \times 106 - 1.48 \times 106}{1.64 \times 106 + 1.48 \times 106} = 0.05$$

where r stands for reflected and i is the incident wave at the boundary. At the interface of two dissimilar medium, reflection of ultrasound beam occurs, consecutively the reflection is small between similar medium such as muscle/fat and soft tissue/urine whereas it is big between the medium such as urine/air as displayed in Table 3. For instance, %1 of the ultrasound energy reflects and %99 travels into the next medium at the muscle/fat junction, which is a desirable feature for our study in terms of transmission of the energy into the bladder when we take into consideration the mediums between the bladder and the wall of the abdomen. Moreover, %99.9 of energy reflects back to the transducer and the remaining %0.01 continues to travel into the next medium at the interface bladder/air, which is also very desirable in terms of obtaining very big interface on the anterior wall of the bladder when it is empty. On the other hand, at the junction point of bladder/urine, %5 reflects and %95 travels into the urine and next medium after the bladder, which causes smaller interface on the anterior and posterior walls of the bladder when there is urine within the bladder with regard to reflection. For instance, it can be noticed that the bigger amplitudes at the anterior wall of the bladder in FIG. 38 for empty bladder are acquired compared to the amplitudes in FIGS. 39, 40 and 41 where the bladder gets larger as the urine level increases. These features reveals important characteristics of the current status of the bladder with respect to the length of the amplitude at the gates.

Another attribute which interact between medium and the wave particle velocity $\upsilon_0$ is the acoustic pressure ($p_0$), expressed in N/m²

$$p_0 = p \cdot c \cdot \upsilon_0 = Z \cdot \upsilon_0 \quad (2)$$

The particle velocity ($\upsilon_0$) is related to amplitude and obtained by dI/dt. Some soft human organs acoustic impedance values are enlisted in Table 2.[6]

TABLE 2

Acoustic impedance of some soft tissues of human body at 37° C.

| | Substance | | | | | | | | | | |
|---|---|---|---|---|---|---|---|---|---|---|---|
| | Bladder | Water | Urine | Air | Bone | Muscle | Fat | Soft tissue | Kidney | Blood | Liver | Lung |
| Acoustic Impedance kg/s · m² * 10⁶ | 1.64 | 1.48 | ≈water | 0.0004 | 7.8 | 1.71 | 1.34 | 1.63 | 1.63 | 1.65 | 1.65 | 0.18 |

TABLE 3

Reflection of ultrasound energy at several interfaces: The reflections from the interfaces, soft tissue/air and soft tissue/bone generate a large echo. We can observe that the reflection coefficient is less than % 1.5 at the interface between soft tissue/soft tissue whereas it is less than % 8 at the interface between fat/soft tissue. [6]

| | Interface | | | | | | | | |
|---|---|---|---|---|---|---|---|---|---|
| | Muscle/ fat | Muscle/ air | Bone/ muscle | Bone/ fat | Soft tissue/ air | Soft tissue/ water | Bladder/ urine | Interior wall of the bladder/air | Interior wall of the bladder/urine |
| Reflection (%) | 1 | ≈99.9 | 41 | 49 | 99.9 | 0.2 | 5 | ≈99.9 | 5 |

As a result of the limits in sound speed, a time delay (at) is inevitable between the moment the sonar wave is produced and the instant the echo has been bounced back. The reflections which occur from media with different acoustic impedances are recorded as function of time. By measuring the (at) and knowing the speed of sound (1540 m/s), the distance (d) to the reflecting boundary, which is half the 2-way travel distance of the sound wave, can be calculated by d=at/2·c.

Frequency selection mostly depends on the level of resolution needed and the total depth that requires to be scanned. Accompanied to all sound propagations is a frequency dependent attenuation. A certain attenuation usually applies to amplitude of echoed signal in all media. In order to equalize the amplitudes of the returning echoes from different depths, it is necessary to correct the attenuation of the pulse as it travels through the tissues. This can be done if the attenuation coefficient of the material is known. Attenuation of the ultrasound energy may be approximated by an exponential $I(dB)=I_0(dB) \exp(-\alpha_x(x))$, where $\alpha_x$ is the attenuation coefficient at a particular depth (x), which varies with depth and frequency.[11] Biologic media have high rates of energy loss and $\alpha_x$ is in range of $1<\alpha_x<1.5$. In soft tissues of body, I is averagely estimated as 0.3 dB/MHz/cm. Due to this frequency dependency, higher frequency waves are damped more strikingly and therefore their penetration depth is restricted.

Observing non-linearity is evidently part of the ultrasonic analysis process. The non-linearity is mainly noticeable by observing the progressive deformation in acoustic wave as it travels thorough a medium.[12, 13] Non-linearity causes harmonic components accumulated over the propagation. The harmonic frequencies are integer multiple of the original frequency. It is proven that the non-linearity is mostly noticeable when ultrasound propagates through liquids.[5] FIGS. 13-15 demonstrate the influence of non-linearity on a typical Gaussian modulated ultrasound transmitted pulses (t) with time-domain equation similar as $$s(t)=P_0 \sin(2ft)e^{(-t/T_w)^2} \qquad (3)$$

in which, $T_W$ is the envelope width and $P_0$ is the initial source pressure, where f is the angular frequency and λ is the wavenumber (the number of radians per unit distance).

The nonlinearity of the medium through which a finite-amplitude ultrasonic wave propagates described in the Goldberg factor which is denoted as:[14]

$$G = \frac{2\pi f p (1 + 0.5\beta)}{(pc^3\alpha)} \qquad (4)$$

in which β is the coefficient of nonlinearity which the generation of higher harmonics depends on it.

Acoustic medium parameters such as the acoustic nonlinearity parameter β are known to be temperature dependant.[15] G indicates the ability of the media to form higher harmonics to an originally pulse wave of finite amplitude during its propagation away from the wave source. It is also dependent on frequency f, and the excitation pressure p. When G is less than unit, the attenuation dominates the non-linearity, and for any G value above 1 the non-linearity takes the lead-according to effectiveness.[16] Fixing the stimulation frequency and the pressure at 3 MHz and 1 MPa, the G factor gets the value of 104 for urine, and 0.27 for soft tissues of body. This demonstrates more intense nonlinearity behaviour for urine (liquid) than other soft tissues (solid). Within soft tissues, non-linear processes also take place, but are attenuated and modified as a result of different acoustic characteristics, like high acoustic absorption.

Figure 13:
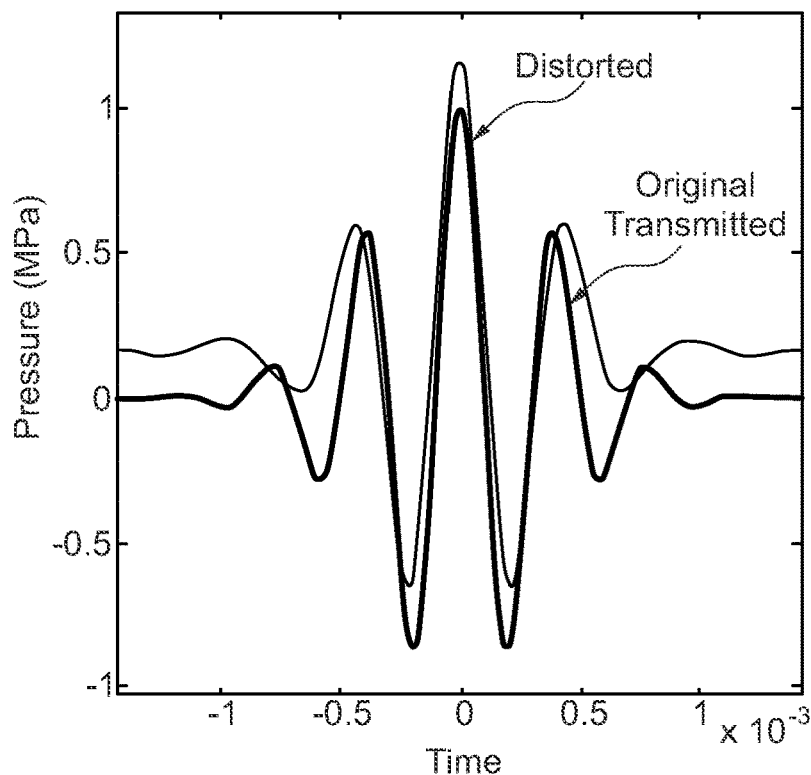
FIG. 13 shows an oscilloscopic trace of Gaussian modulated ultrasound wave pulses (t) in the time-domain (as per Equation (3)), showing both distorted (red) and non-distorted (blue) waves.
Figure 14:
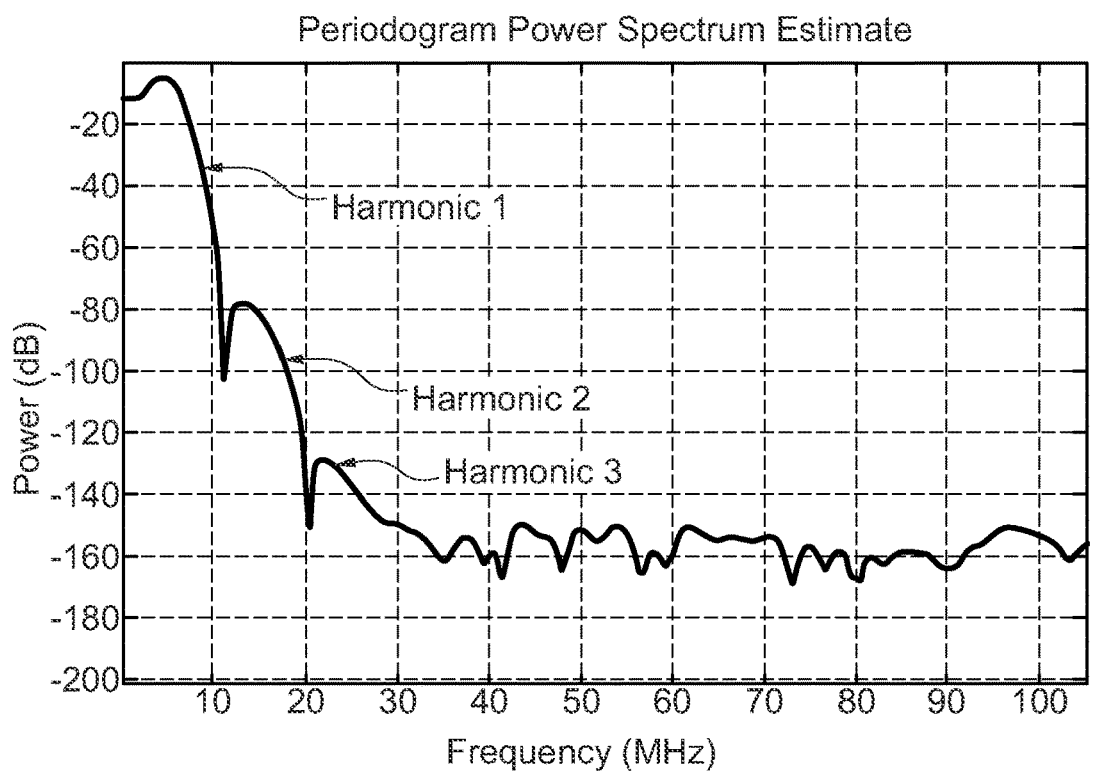
FIG. 14 shows a frequency-domain periodogram of a linear-pulsed plain acoustic wave.
Figure 15:
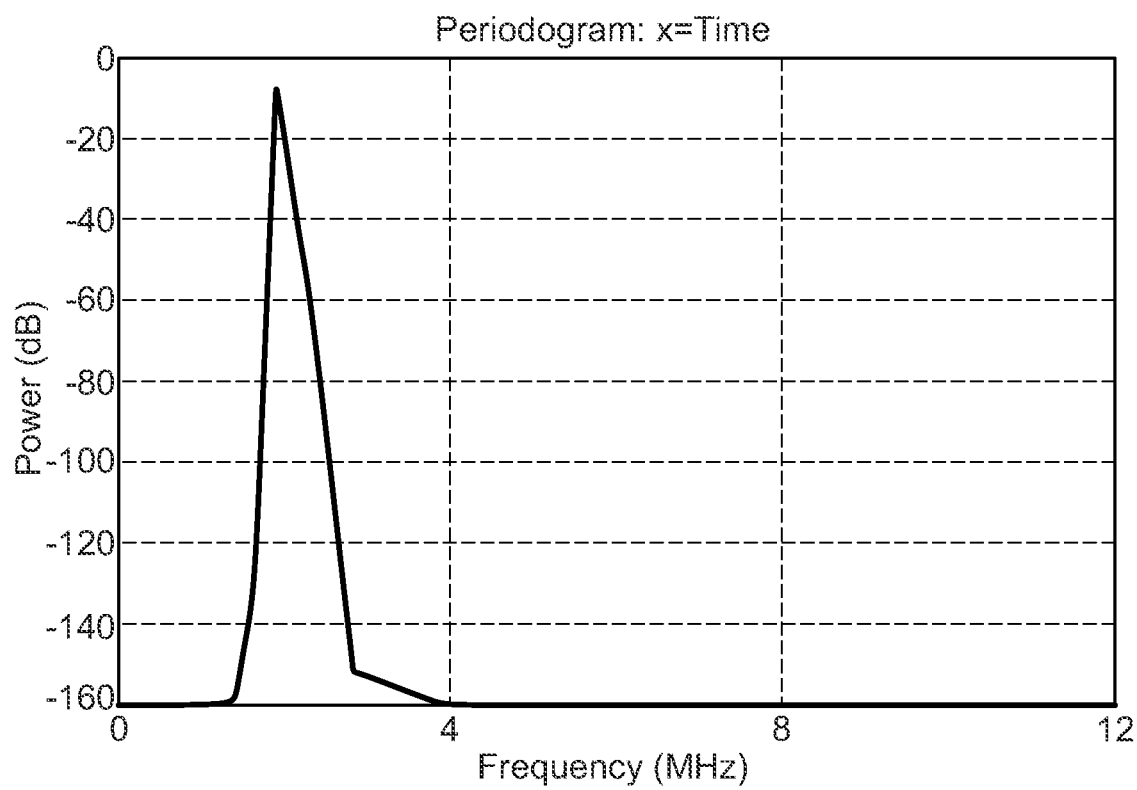
FIG. 15 shows a frequency-domain periodogram of a non-linear-pulsed acoustic wave (i.e. a wave that has propagated through a medium to yield harmonics, etc.)

FIGS. 13-15 collectively show a comparison between a linear and a non-linear pulsed, plane acoustic wave. The waves propagate in water and are evaluated at a propagation distance 0.12 m. In particular, FIG. 13 shows an oscilloscopic trace of Gaussian modulated ultrasound wave pulses (t) in the time-domain (as per Equation (3)), showing both distorted (red) and non-distorted (blue) waves. FIG. 14 shows a frequency-domain periodogram of a linear-pulsed plain acoustic wave, whereas FIG. 15 shows a frequency-domain periodogram of a non-linear-pulsed acoustic wave (i.e. a wave that has propagated through a medium to yield harmonics, etc.)

When a sound wave travels through a tissue with a uniform density and encounters an interface with a different density, some of that sound wave bounces back as an echo.[17] Sound energy is attenuated or weakened as it passes through tissue because parts of it are reflected, scattered, absorbed, refracted or diffracted.

To summarize, as the ultrasound waves penetrate body tissues of different acoustic impedances along the path of transmission, some are reflected back to the transducer (echo signals) and some continue to penetrate deeper. Sound waves can be described in terms of their frequency (measured in cycles per second or hertz), wavelength (measured in millimetre), and amplitude (measured in decibel). The wavelength and frequency of US are inversely related, i.e., ultrasound of high frequency has a short wavelength and vice versa. High-frequency waves are more attenuated than lower frequency waves for a given distance; thus, they are suitable for imaging mainly superficial structures. Conversely, low-frequency waves (long wavelength) offer images of lower resolution but can penetrate to deeper structures due to a lower degree of attenuation. Low-frequency transducers are typically 2-5 MHz. The intensity of a reflected echo is proportional to the difference (or mismatch) in acoustic impedances between two mediums. If two tissues have identical acoustic impedance, no echo is generated. Interfaces between soft tissues of similar acoustic impedances usually generate low-intensity echoes. Conversely interfaces between soft tissue and bone or the lung generate very strong echoes due to a large acoustic impedance gradient. If the incident US beam reaches the linear interface at 90, almost all of the generated echo will travel back to the transducer. However, if the angle of incidence with the specular boundary is less than 90°, the echo will not return to the transducer, but rather be reflected at an angle equal to the angle of incidence (just like visible light reflecting in a mirror). As US pulses travel through tissue, their intensity is reduced or attenuated. This attenuation is the result of reflection and scattering and also of friction-like losses. These losses result from the induced oscillatory tissue motion produced by the pulse, which causes conversion of energy from the original mechanical form into heat. This energy loss to localized heating is referred to as absorption and is the most important contributor to US attenuation. Longer path length and higher frequency waves result in greater attenuation. Attenuation also varies among body tissues, with the highest degree in bone, less in muscle and solid organs, and lowest in blood for any given frequency. The attenuation for some organ compared to water and urine is depicted in Table 4.[5]

TABLE 4

Acoustic properties of different tissues in terms of acoustic loss[5]

| Tissue | Sound velocity (m/s) | Density (g/cm$^3$) | B/A | Acoust. loss ($\alpha$) (dB/(mm · MHz$^b$)) | b |
|---|---|---|---|---|---|
| Fat | 1436 | 0.928 | 9.6 | 0.30 | 0.9 |
| Muscle | 1550 | 1.060 | 5.8 | 0.05 | 1.1 |
| Blood | 1584 | 1.060 | 6.0 | 0.01 | 1.2 |
| Urine | 1551 | 1.025 | 6.1 | 0.00047 | 1.67 |
| Water | 1524 | 0.993 | 5.4 | 0.00014 | 2.0 |

TABLE 5 the very small acoustic loss in Urine. HVT is the distance which reduces the intensity of an ultrasound signal to one half of its original propagated signal in terms of the frequency and the properties of the medium it propagates. [6]

| | HVT (Half value thickness) (cm) | | | | | |
|---|---|---|---|---|---|---|
| | Water | Urine | Muscle | Fat | air | Bone |
| 2 MHz | 340 | ≈water | 0.75 | 2.1 | 0.06 | 0.1 |
| 5 MHz | 54 | ≈water | 0.3 | 0.86 | 0.01 | 0.04 |

As can be seen from Table 4, fluid-containing structures such as the bladder attenuate sound much less than solid structures so that the strength of the sound pulse is greater after passing through fluid than through an equivalent amount of solid tissue.[18]

The Goldberg number was calculated at an acoustic pressure of 1 MPa and a transmit frequency of 3 MHz[5] as explained in more detail below: both values lie within the diagnostic range. The calculations demonstrate that, for these transmission parameters, only fat has a Goldberg number below 1 (0.27). All other media show values greater than 1, of which urine has the highest (104) as presented in FIG. 16.

Figure 16:
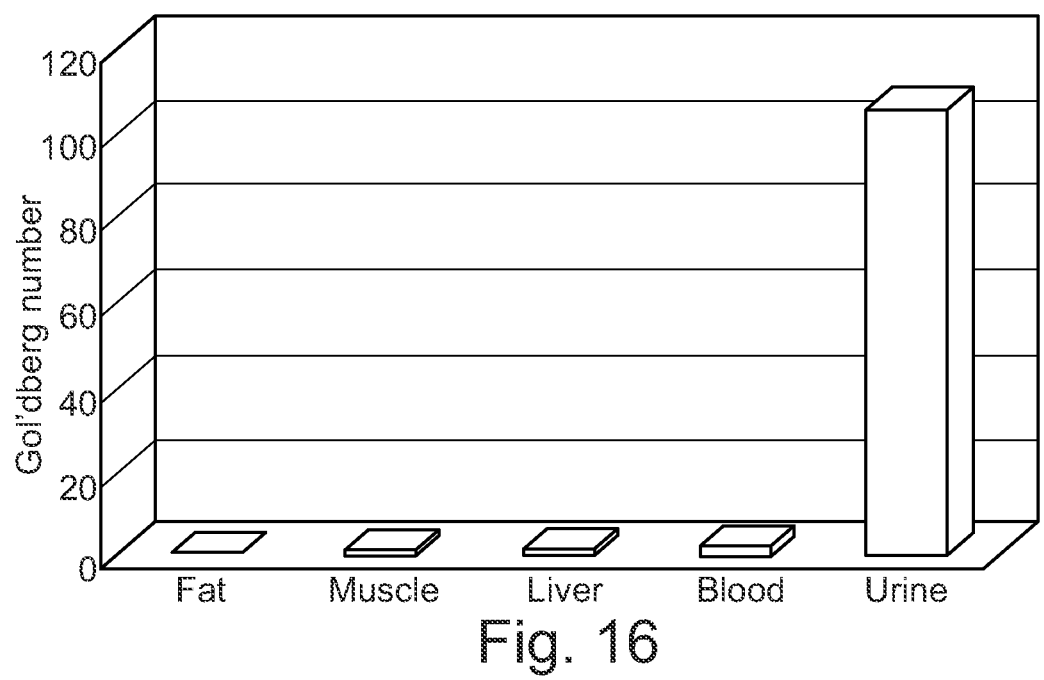
FIG. 16 is a bar chart illustrating the Goldberg number calculated for different media at a transmit frequency of 3 MHz and acoustic pressure of 1 MPa.[5]

FIG. 16 is a bar chart illustrating the Goldberg number calculated for different media at a transmit frequency of 3 MHz and acoustic pressure of 1 MPa.[5]

This is caused primarily by the attenuation, which is very low for urine and very high for fat, although the nonlinearity coefficient of fat is higher than that of urine. These simple calculations demonstrate the difference between different media in causing waveform distortion. Urine has a higher ability to provoke strong nonlinear distortion compared with other body tissues[5] and thereby provide more information. When G=1, nonlinear effects become comparable to attenuation effects. If the Goldberg number is higher than 1, nonlinear processes dominate the wave propagation behaviour.

Figure 17:
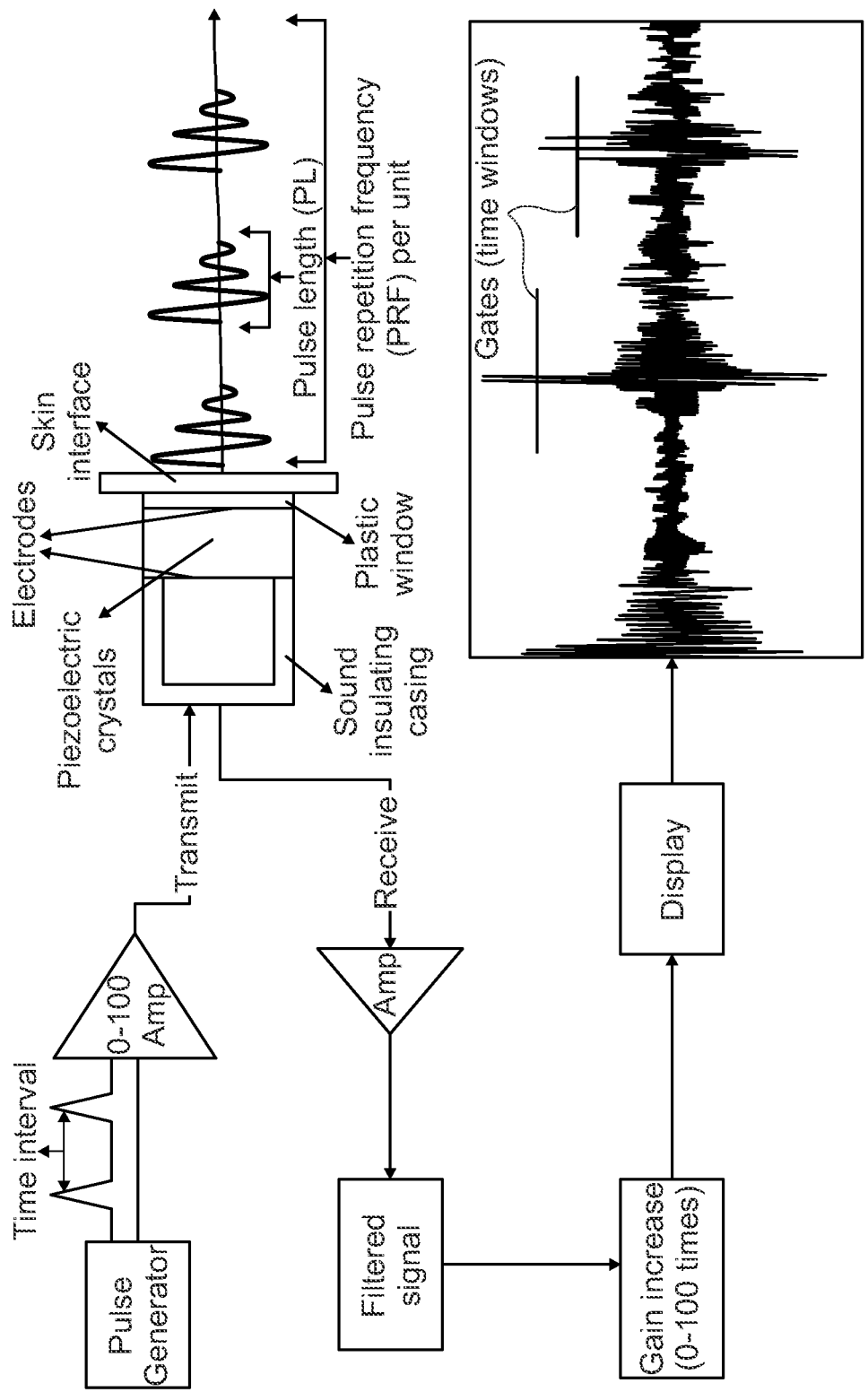
FIG. 17 shows a schematic view of an A-scan ultrasound system.

The excitation signal is usually an impulse of between 20 V and 300 V[19]. However, this system uses a voltage less than 100V as displayed in FIG. 17 that delineates how our model of an "A-scan" transducer works. The acquired attenuation signal is increased by a gain value ranging from 20 to 100 to make the signal difference more explicit. The dynamic range of the signal following amplification may be as high as 100 dB. FIG. 17 meanwhile simply shows how an attenuation signal can be obtained from an organ using A-scan system.

FIG. 17 shows a schematic view of an A-scan system.

FIG. 18 illustrates the acquisition of attenuation signals throughout the body organs with respect to incident beam, transmitted beam and reflected beam: a pulse is transmitted and reflections come back.

A pulse is transmitted and reflections come from the walls of the bladder. Note that the reflection beam from the posterior wall can be obtained easier than that from the anterior wall in our drawing example based on the position of the bladder walls; reflected angles are $\theta_r$ and $\theta_{r2}$ respectively.

$$\frac{\sin \theta_t}{\sin \theta_i} = \frac{c_2}{c_1}$$

The rule of refraction (direction of the transmitted beam) of transmitted beam with regard to the interface between bladder and the urine in the bladder is displayed in the formula (Snell's Law) above. The refraction is very important in terms of detecting a reflected beam at the posterior wall of the bladder with regard to the angle, $\Theta_{r2}$, as displayed in FIG. 18. The velocities of bladder walls and the urine are almost same ($\approx 1540$), hence, transmitted beam refracts slightly and the angle, $\Theta_{r2}$, is crucial for the transducer to receive the reflected beam from the posterior wall. In addition, there is another critical feature for the reflected beam at the walls of the bladder, which is the smooth characteristic of the exterior and interior surface. A beam from the bladder reflects specularly by the help of the smooth surface as shown in FIG. 18 without scattering (e.g., brighter appearance in B-mode) and almost with a same angle where it faces on the interface. Most importantly, the specular reflection from the homogeneous/smooth surface helps the reflected beam to be detected by the transducer with high amplitudes regardless of angles of an incident beam based on the outcome of the tests we have carried out on phantoms. A rough and uneven/diffused surface such as heart chambers or kidneys would cause the beam to scatter into many directions and consequently the attenuation would become much more (i.e., smaller amplitude) in terms of the detected reflected beam by a transducer.

Figure 19:
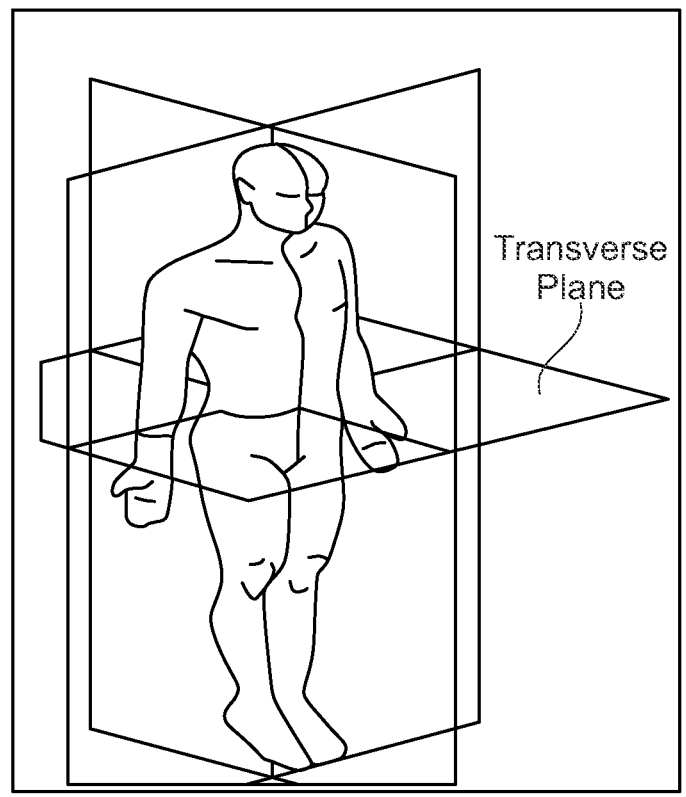
FIG. 19 depicts both sagittal and transverse planes of a body.

FIG. 19 depicts both sagittal and transverse planes of a body.

The bladder is usually scanned trans-abdominally, using an ultrasound probe on the abdomen at the suprapubic region, to provide transverse and sagittal views.[17] A-scan shows the bladder as a globe-like structure with the interface between the bladder wall and the urine showing a clear demarcation. The bladder wall has a symmetrical, smooth, gently curved surface as can be seen in the simulated images displayed in the first cover page. In a transverse scan (FIG. 19), its shape can vary from almost circular to square.[17]

The characteristics of urine in the bladder and the bladder itself regarding the attenuation signals are significantly different from those of the other organs in the body as it can be seen in Table 4. In addition, the features of the bladder with regard to expansion and contraction based on the urine in the bladder are different from those of the other organs in the body. The expected bladder capacity (EBC) was calculated using the formula [(age in years+1) 30=ml][3]. The wall of the bladder gets thicker or thinner based on the expansion and contraction. The attenuation signals acquired from the anterior wall give the state of the emptiness where it is empty rather than the posterior wall because there is gas/air inside which is the enemy of the ultrasound and scatters the propagation signals in all directions in a non-uniform manner resulting in no meaningful attenuation signals returning to transducer from the posterior wall of the bladder as delineated in FIG. 20. In this case, the attenuation signals are acquired from the anterior wall. On the other hand, the meaningful attenuation signals can be acquired from the posterior wall of the bladder where there is urine inside the bladder as delineated in FIG. 21. The propagation signals from the transducer move throughout the bladder to the posterior wall and propagation signals are acquired right after the signals obtained from the anterior wall. The strengths of these two signals are almost equal to each other, but, the later one is a little bit smaller as delineated in FIG. 18 as front face and back face based on the low attenuation as depicted in Table 4 for urine.

Figure 20:
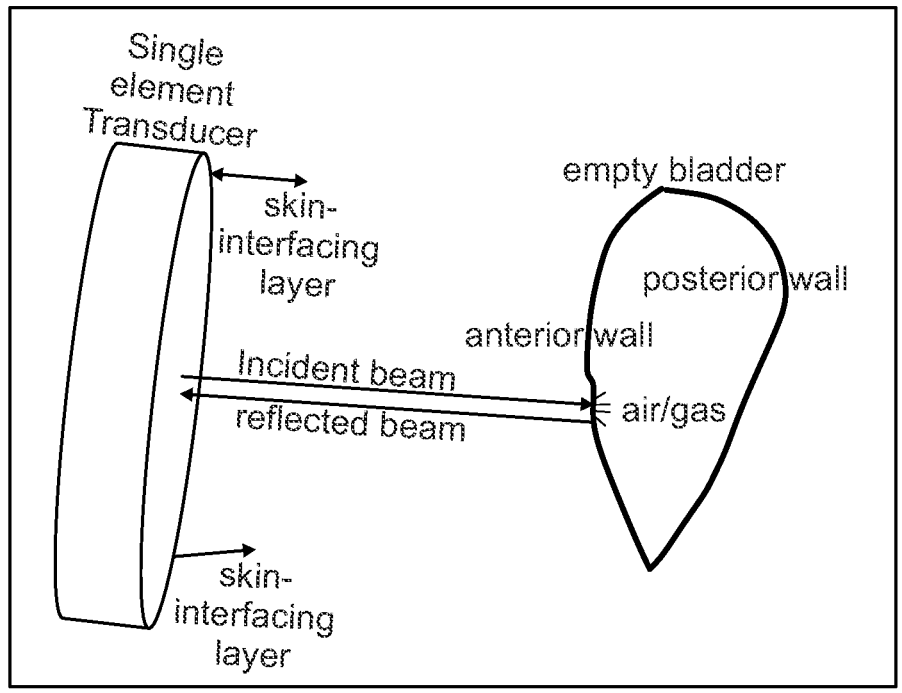
FIG. 20 is a diagram showing a single-element ultrasound transducer and respective propagation and attenuation signals for an empty bladder. The propagation signal after the anterior wall of the bladder is scattered in all directions in a non-uniform manner due to gas/air within the bladder.

FIG. 20 is a diagram showing a single-element ultrasound transducer and respective propagation and attenuation signals for an empty bladder. The propagation signal after the anterior wall of the bladder is scattered in all directions in a non-uniform manner due to gas/air within the bladder. Almost all the energy of the beam is reflected at the interface between the interior wall of the bladder and air based on the acoustic impedance values they have, namely, $1.64 \times 10^6$ and $0.0004 \times 10^6$ respectively with a reflection value of %99.9. An interface with big amplitude emerges due to the big difference between the impedance values of these two mediums as well. The remaining ultrasound beam with a very small energy passing through the gas scatters in all directions in a non-uniform manner; because ultrasound beams can't travel through a vacuum and no beam returns from the posterior wall into the transducer.

Figure 21:
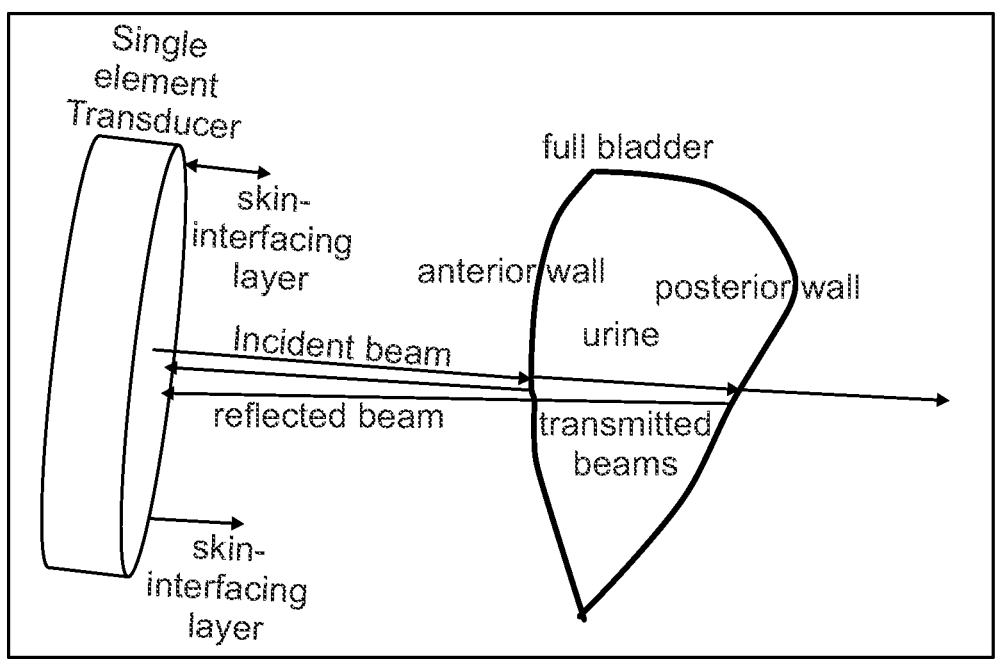
FIG. 21 is a diagram showing a single-element ultrasound transducer and respective propagation and attenuation signals for a full bladder, where the propagation signals after the anterior wall of the bladder do not lose their strength because the urine inside the bladder causes little attenuation or scattering.

FIG. 21 is a diagram showing a single-element ultrasound transducer and respective propagation and attenuation signals for a full bladder, where the propagation signals after the anterior wall of the bladder do not lose their strength because the urine inside the bladder causes little attenuation or scattering. Propagation and attenuation signals for the bladder within urine: the propagation signal after the anterior wall of the bladder doesn't not lose its strength propagating toward to the posterior wall; because, the difference between the impedance values of these two medium is not so big ($1.64 \times 10^6$ and $1.48 \times 10^6$) and urine inside the bladder causes a very little attenuation (i.e., acoustic loss is 0.00047) for the beam coming through the anterior wall.

Furthermore, a number of harmonics useful in the determination of characteristics of the liquid are generated and observed as the result of ultrasound propagation through liquid medium. Merk[5] has studied the relationship between the detected harmonic components and the urine volume present in the bladder: a pulsed ultrasonic signal is transmitted at a certain fundamental frequency; the received echoes that originate from a certain depth beyond the average position (at approximately 12 cm for adults) of the posterior bladder wall are analysed for the presence of higher harmonics of the fundamental transmit frequency. The received echo signal contains information about almost the entire bladder as the wide ultrasound beam encompasses the largest part of the bladder. Due to nonlinearity, higher harmonic components build up during propagation through urine, which can be detected in the returning echo. With empty bladders, the higher harmonics are less apparent because nonlinear effects occur most strongly when ultrasound (US) propagates through liquids with relatively low acoustic attenuation, such as water or urine. Feasibility was proven using in vitro measurements on bladder phantoms. These harmonics can be analyzed in frequency domain and consequently distinctive features (e.g., characteristics of first, second and third harmonics) indicating the volume of urine within the bladder can be acquired.

Figure 22:
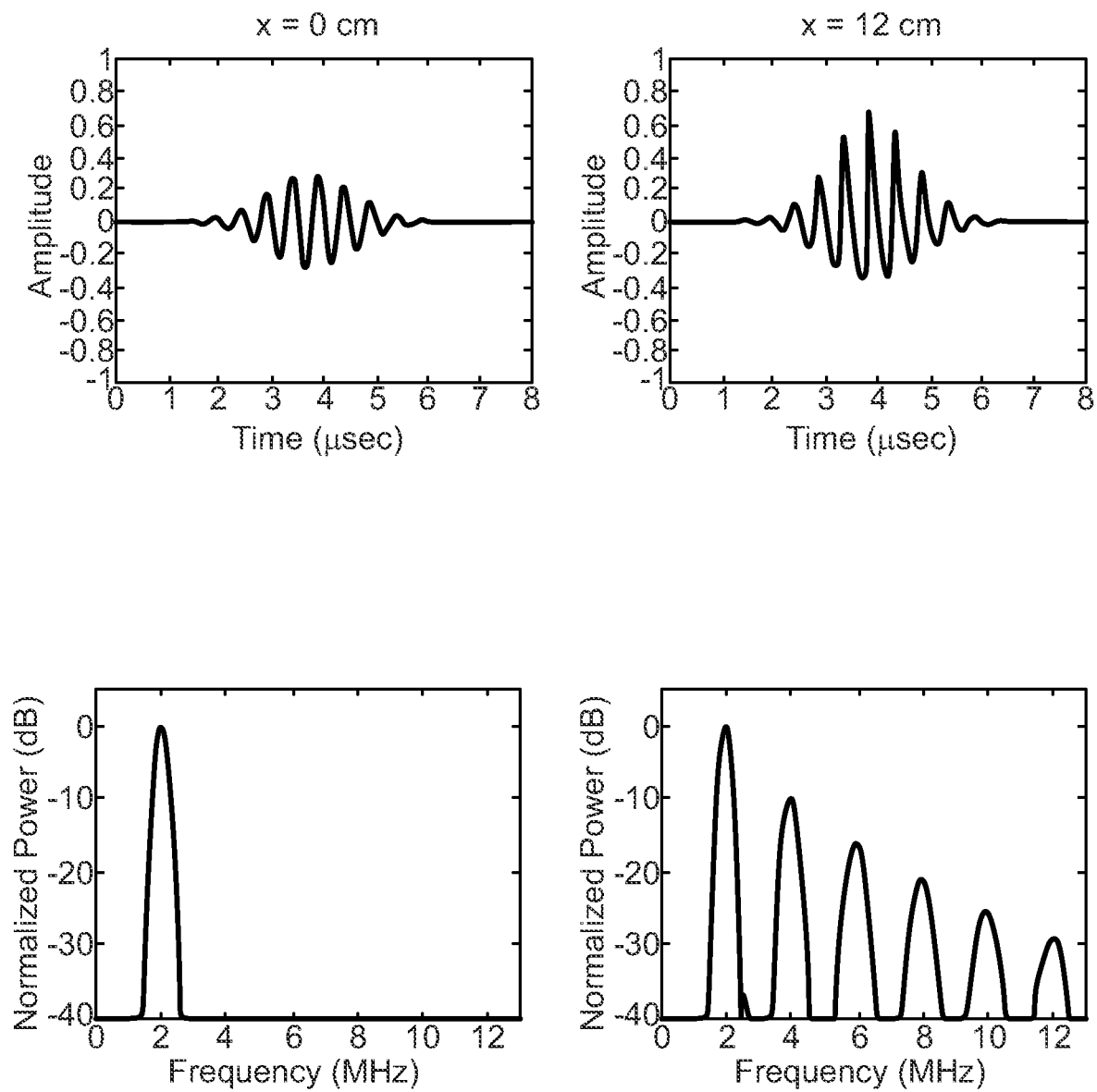
FIG. 22 shows pressure waveforms of an ultrasound pulse at the transducer surface (top left) and after propagation over a distance of 12 cm (top right) in water. Their corresponding normalized frequency spectra are plotted below.[5] The top left part of the figure shows the initial transmitted waveform at distance x=0 cm from the transducer. Its normalized frequency spectrum (bottom left) contains only the fundamental frequency (in this case 2 MHz). The top right part shows the same ultrasound pulse after it has propagated through water over a distance of x=12 cm. Clearly, the wave shape has changed from a sinewave to an asymmetric sawtooth-like waveform with sharp positive peaks.

Also, measurements on a volunteer showed that bladder volume assessment on the basis of nonlinear wave propagation is feasible in vivo[5]. FIG. 22 shows the effect of nonlinear wave propagation on a typical ultrasound pulse transmitted by a transducer. The top left part of the FIG. 22 shows the initial transmitted waveform at distance x=0 cm from the transducer. Its normalized frequency spectrum (bottom left) contains only the fundamental frequency (in this case 2 MHz). The top right part of FIG. 22 shows the same ultrasound pulse after it has propagated through water over a distance of x=12 cm. Clearly, the wave shape has changed from a sinewave to an asymmetric sawtooth-like waveform with sharp positive peaks. The normalized frequency spectrum now shows a significant amount of higher harmonics.

FIG. 22 shows pressure waveforms of an ultrasound pulse at the transducer surface (top left) and after propagation over a distance of 12 cm (top right) in water. Their corresponding normalized frequency spectra are plotted below[5]. The top left part of the figure shows the initial transmitted waveform at distance x=0 cm from the transducer. Its normalized frequency spectrum (bottom left) contains only the fundamental frequency (in this case 2 MHz). The top right part shows the same ultrasound pulse after it has propagated through water over a distance of x=12 cm. Clearly, the wave shape has changed from a sinewave to an asymmetric sawtooth-like waveform with sharp positive peaks.

In conclusion, a single-element transducer can be used to detect the state of the bladder (i.e., empty, ½, ¾, full) by exploiting and merging the features, characteristics and patterns of the bladder mentioned above.

Example—Using Ultrasound to Calculate Urine Volume in Bladder

The present invention can utilise a comparison of nonlinear wave distortion capabilities between urine-loaded bladder in conjunction with the surrounding tissues, and the same surrounding tissues with voided bladder. The nonlinearity behaviour changes when the wave propagates through various media. To take advantage of these harmonic differences, reflected signal from the posterior wall of an average filled bladder are analysed for harmonic contents. The harmonic content is then utilised to calibrate the system for volume of liquid encased in the bladder[20].

The methodologies now described apply to those described in the Specific Embodiment(s) above.

We would like to give some summarized information about the ML techniques we have employed in our study. SMO is an algorithm for solving the quadratic programming (QP) problem that arises during the training of support vector machines. It was invented by John Platt in 1998 at Microsoft Research.[21] Training a support vector machine requires the solution of a very large quadratic programming (QP) optimization problem. SMO breaks this large QP problem into a series of smallest possible QP problems. These small QP problems are solved analytically, which avoids using a time-consuming numerical QP optimization as an inner loop. The amount of memory required for SMO is linear in the training set size, which allows SMO to handle very large training sets. Because matrix computation is avoided, SMO scales somewhere between linear and quadratic in the training set size for various test problems, while the standard chunking SVM algorithm scales somewhere between linear and cubic in the training set size. SMO's computation time is dominated by SVM evaluation, hence SMO is fastest for linear SVM and sparse data sets. On real world sparse data sets, SMO can be more than 1000 times faster than the chunking algorithm. Our second ML technique is Linear Regression. Linear regression is one of the most commonly used statistical method that is generally used for prediction. The goal in regression analysis is to create a mathematical model that can be used to predict the values of a dependent variable based upon the values of an independent variable using the Akaike criterion[22, 23] to find the best model that fits the data set best. The third ML algorithm, Grid Search performs a grid search of parameter pairs for a classifier and chooses the best pair found for the actual predicting. The initial grid is worked on with 2-fold CV to determine the values of the parameter pairs for the selected type of evaluation (e.g., accuracy). The best point in the grid is then taken and a 10-fold CV is performed with the adjacent parameter pairs. If a better pair is found, then this will act as new center and another 10-fold CV will be performed such as hill-climbing algorithm. This process is repeated until no better pair is found or the best pair is on the border of the grid. The final ML algorithm, Bagging, Bootstrap Aggregating, constructs separate samples of the training data set and creates a classifier for each sample. The results of these multiple classifiers are then combined using averaged or majority voting. These algorithms take several parameters based on the count of the instances in data sets and the characteristics of the data sets. Some parameters chance automatically specific to the characteristics of the data set. Some are embedded in the software as being the optimized parameters.

The system can evaluate the data set using 3 cross-validation techniques, namely Holdout cross-validation (50/50), k-fold cross-validation and leave-one-out cross-validation (LOOCV) schemes. Holdout cross-validation (50/50) has the disadvantage that fails to use all the available data; if we use half the data for the test set, then we are only training on half the data and we may get a poor hypothesis. On the other hand, if we reserve only 10% of the data for the test set, then we may, by statistical chance, get a poor estimate of the actual accuracy[24]. We can squeeze more out of the data and still get an accurate estimate using a technique called k-fold cross-validation. The idea is that each example serves double duty-as training data and testing data. First we split the data into k equal subsets. We then perform k rounds of learning; on each round 1/k of the data is held out as a test set and the remaining examples are used as training data[25]. The average test set score of the k rounds should then be a better estimate than a single score. On the other hand, LOOCV requires longer computation time. It is not advised for big data sets. In leave-one out-cross-validation scheme, we leave one instance out as a test instance and train the system using the remaining instances. This process is repeated as many times as there are instances in the dataset, so every data point is used as a test sample to measure its similarity to the others.

Several noise reduction algorithms such as wavelength technique can be performed to obtain better data sets.

We developed an application in both C # and Java programming languages to both train/test our data set and diagnose the status of the bladder correctly based on the instances acquired from the people who are suffering from the nocturnal enuresis. The main screen of our implementation in C # is shown in FIG. 23.

Figure 23:
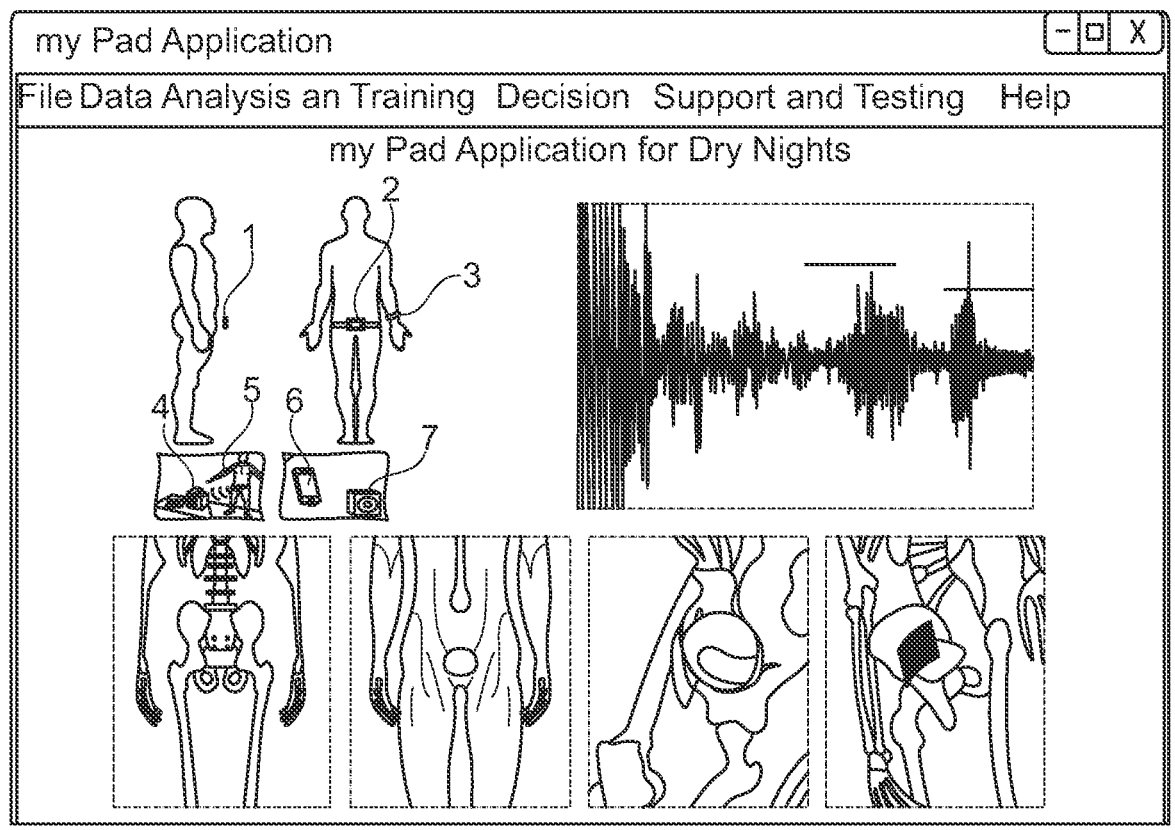
FIG. 23 is a screen shot of the Main Screen of the computer program: the main menus are "File", "Data Analysis and Training", "Decision Support and Testing" and "Help". The general design of the system along with the design of the general idea about how it works are delineated on the screen.

FIG. 23 is a screen shot of the Main Screen of the computer program: the main menus are "File", "Data Analysis and Training", "Decision Support and Testing" and "Help". The general design of the system along with the design of the general idea about how it works are delineated on the screen.

Other components of the implementation can be called from this main screen using menus at the top of the screen such as "File", "Data Analysis and Training", "Decision Support and Testing" and "Help".

Figure 24:
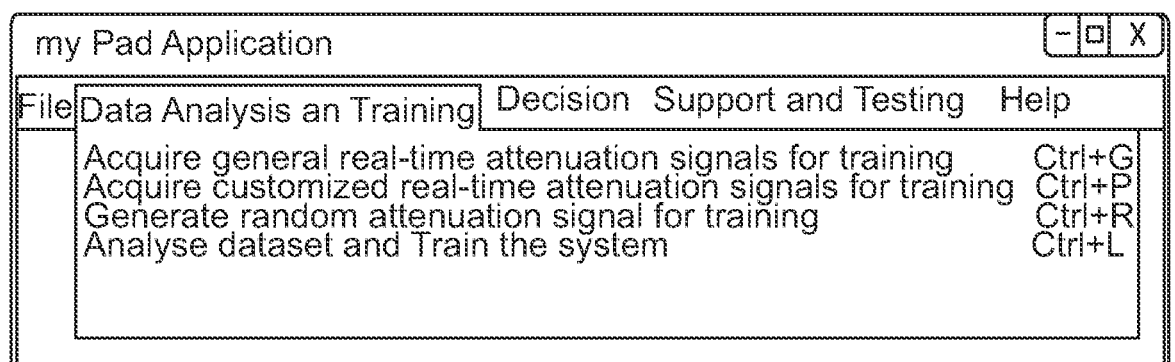
FIG. 24 is a screen shot showing the functions of the menu, "Data Analysis and Training".

The functions under the "Data Analysis and Training" are displayed in FIG. 24. The screen in FIG. 25 is displayed when the function, "Acquire general real-time attenuation signals for training" is called.

Figure 25:
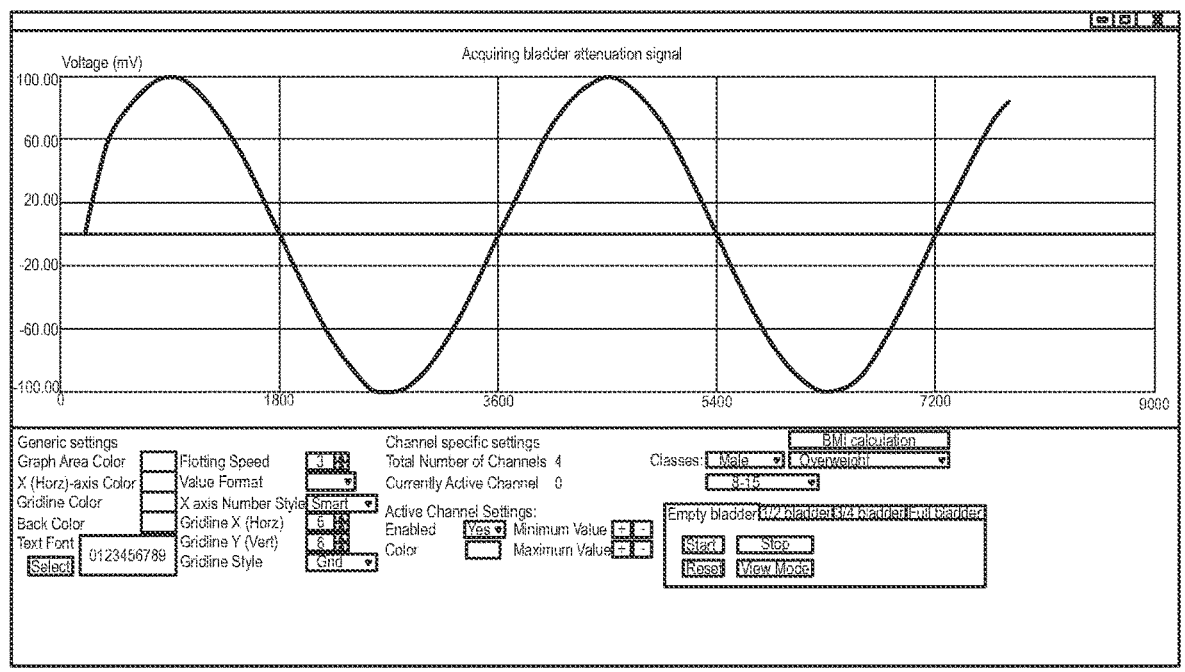
FIG. 25 is a screen shot of the screen for acquiring general real-time attenuation signals for training.

FIG. 25 is a screen shot of the screen for acquiring general real-time attenuation signals for training. The instances for attributes specific to the bladder such as attenuation signals, bladder thermal energy, pulse energy transmission, and accumulated harmonics within the urine, at a time are obtained for the classes displayed in FIG. 31 by using combo-boxes specified for the sex, age-interval, body mass index (BMI) and the states of the bladder. BMI is calculated by applying the Oxford University formula[26] to be objective rather than to depend on the subjective criteria by activating the button, "BMI calculation".

Figure 26:
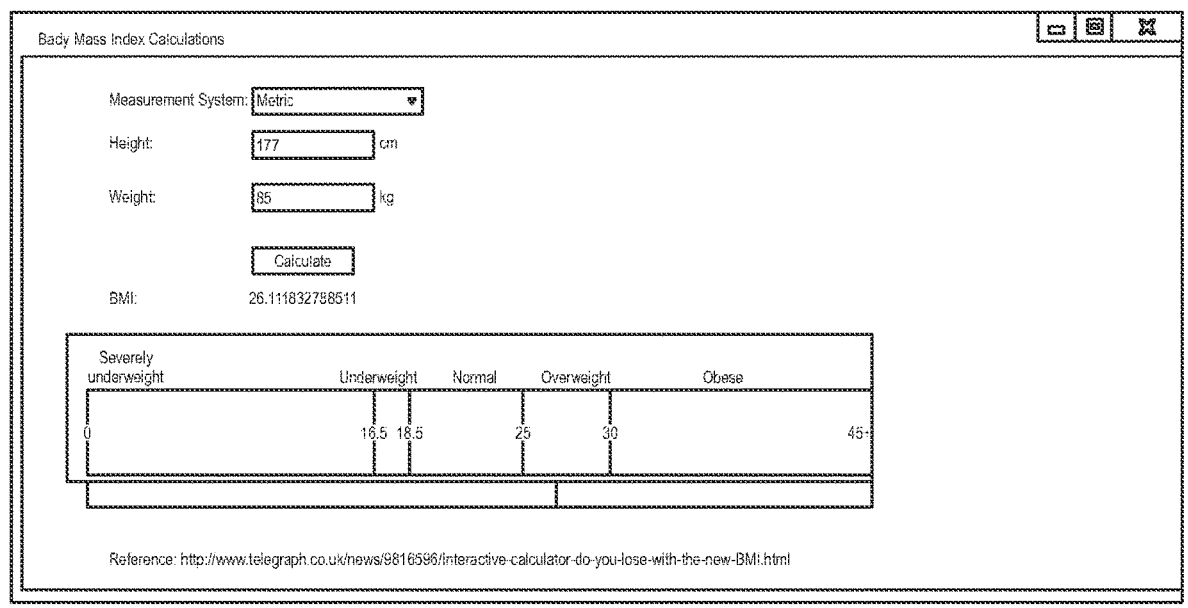
FIG. 26 is a screen shot of the screen for calculating BMI: people are categorized as severely underweight, underweight, normal, overweight and obese based on the height and weight. The person is found to be overweight in this example with a value of 26. Reflected signals at the interfaces between the abdomen and the bladder generate small amplitude values in terms of the soft tissues with regard to slim people. On the other hand, the difference in Z value between the fat (i.e., $1.34 \times 10^6$) and the soft tissue (i.e., $1.65 \times 10^6$) generates stronger amplitude. Hence, we used BMI in our intelligent application to assess the characteristics of the amplitude better, especially between the abdomen and the bladder.

FIG. 26 is a screen shot of the screen for calculating BMI: people are categorized as severely underweight, underweight, normal, overweight and obese based on the height and weight. The person is found to be overweight in this example with a value of 26.

The application has been designed to decrease the intensity and signal exposure time to the minimum by considering the safety issues (i.e. lower power helps protect patients from the side effects of ultrasound overdose). The gain parameter of the system can be tuneable between 0 and 100 to make the acquired signal more distinctive during the post-processing of the acquired signal to get the most information at the lowest output power. The Pulse Repetition Frequency (PRF: Number of pulses occurring in 1 s) of the device can be tuneable between 200 Hz and 2000 Hz in relation with pulse repetition period (i.e. PRP (i.e. the distance between two pulses) decreases as PRF increases). The device can be managed by an intelligent software to adjust the best values for the parameters. For instance, the timing (i.e., pulse emission time intervals (PETI) will be adjusted by the application automatically in terms of the data acquired from the bladder by minimizing scan time as minimum as possible, in other words, the beams will be sent to the person once (duration<25 ns) in ranging between 5 and 20 minutes during sleeping time (e.g., 8 hours) (i.e., if the bladder is detected as empty, next beam will be sent after 20 minutes later whereas the other beam will be sent to the person after 5 minutes later if the bladder is detected as % full.). We aim to employ the A-mode use of Ultrasound, and we don't aim to get an image from the bladder. That's why we don't need to apply US beams a long time and with big intensity values (W/cm$^2$) on the bladder. To summarize, the device is designed not to cause both any bio-effects regarding the mechanical index (MI) and any increase of the temperature in the body regarding the thermal index (TI) specified in the International Guidelines and Regulations for the Safe Use of Diagnostic Ultrasound in Medicine dictated by WFUMB (World Federation for Ultrasound in Medicine and Biology), AIUM (American Institute of Ultrasound in Medicine), ASUM (Australasian Society for Ultrasound in Medicine), EFSUMB (European Federation of Societies for Ultrasound in Medicine and Biology), ODS/FDA (Output Display Standard/US Food and Drug Administration) which would make our device ready-to-use worldwide product in terms of the regulations and legislations.

The transducer sends signals to the body when the button, "Start" is clicked and it stops when the button, "Stop" is clicked. The upper graphic on the screen corresponds to the electric voltage sent to the transducer. The sinusoidal lines are only drawn as long as the signals are sent to the bladder using "Start" button, otherwise drawing sinusoidal lines is deactivated.

Figure 27:
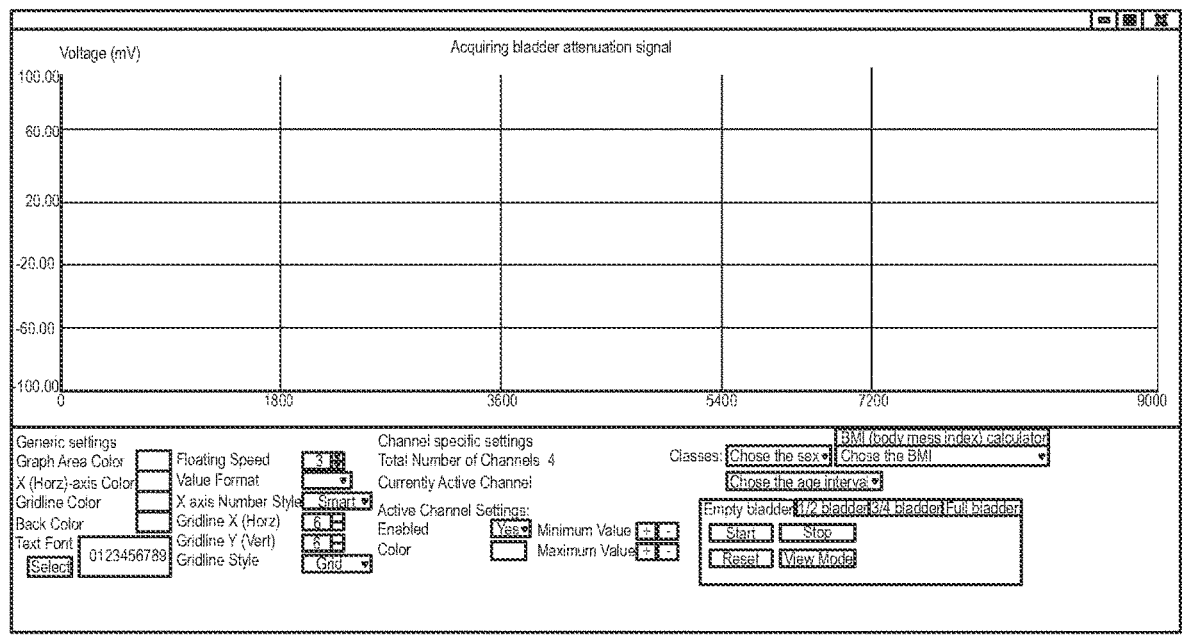
FIG. 27 shows a screen shot of the screen for acquiring customized real-time attenuation signals for training: sex, BMI and age interval attributes are obtained to feed the general data set rather than to train the system with customized instances.

The system is designed not only to use the general established classifiers but also to use the classifiers customized for any person, which is expected to result in better accuracy rate. In this sense, the screen in FIG. 27 is displayed when the function, "Acquire customized real-time attenuation signals for training" is called. This screen looks like the screen for the function, "Acquire general real-time attenuation signals for training" mentioned in the previous paragraph. However, the acquired instances in this function are specific to people who are suffering from the nocturnal enuresis. In this screen the system doesn't need sex, BMI and age interval attributes to train the system, but, we aim to use these instances to feed the general data set as well. The instances are acquired for each state of the bladder for a person for several times (e.g., 10 to 100) to make sure the classifiers are established properly for the training phase to support decision support (i.e., to find out the present state of the bladder) for further instances obtained from the same person, especially during sleeping.

Figure 28:
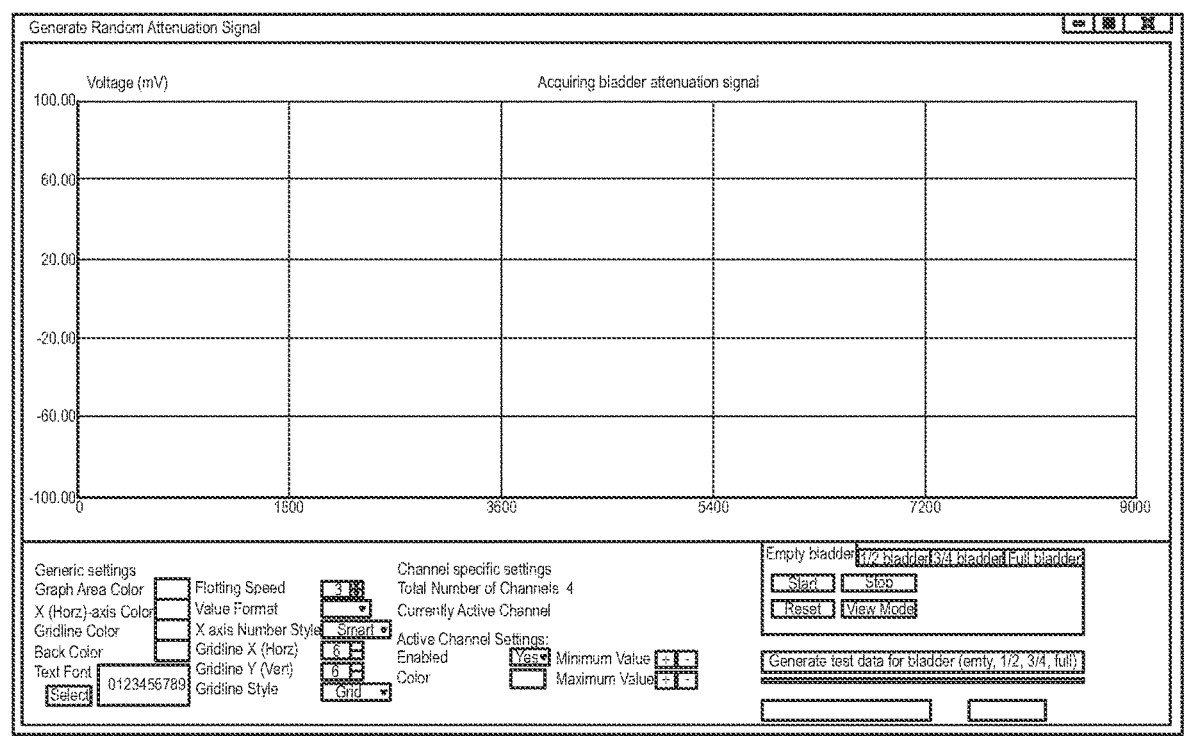
FIG. 28 is a screen shot showing random generation of the data set for each state of the bladder: the button, "Generate test data for the bladder", generates 400 instances for general dataset, 100 for each state of the bladder (empty, ½, ¾, and full). The created dataset can be displayed by clicking the button, "Open all dataset".

The screen in FIG. 28 is displayed when the function, "Generate random attenuation signals for training" is called. Our application can generate instances randomly mimicking the attenuation signals and harmonics acquired from the anterior and posterior walls of the bladder using a single-element transducer for the four states of the bladder (empty, ½, ¾, and full) by using this screen similar to real environment. The button, "Generate test data for the bladder", generates 400 instances for general dataset, 100 for each state of the bladder (i.e., empty, ½, ¾, and full). The screen in FIG. 24 is displayed when the function, "Analyse data set and Train the system" is called. 5 instances from each state of the bladder in the data set are plotted in the graph at the top of the screen in the dedicated tab controls to observe the patterns of the states. Clicking the button, "Train the system using the ML algorithms below" starts the training process regarding four ML algorithms displayed at the bottom left of the screen in which the success rates of the techniques are displayed in the dedicated text boxes. Training for each technique starts at the same time in a parallel processing programming to reduce the processing time significantly. The detailed statistical results of the techniques are shown at the bottom right of the screen in the dedicated tab controls. The system employs several machine learning (ML) algorithms on our data set and the accuracy of the algorithms are evaluated using holdout, n-fold and one leave-out cross-validation (OLOCV) depending on the number of the instances (Table 6). We selected four ML techniques that fit our data set best in terms of the accuracy rates of the techniques. These techniques are sequential minimal optimization (SMO) for training a Support Vector Classifier, Grid Search, Linear Regression and ensemble bagging meta learning algorithms.

TABLE 6

Validation techniques employed based on the # of instances

| Validation Technique | # of instances (x) |
|---|---|
| Holdout cross-validation | x >= 1000 |
| 10-fold cross-validation | 100 <= x < 1000 |
| One-leave-out cross-validation | x < 100 |

Figure 29:
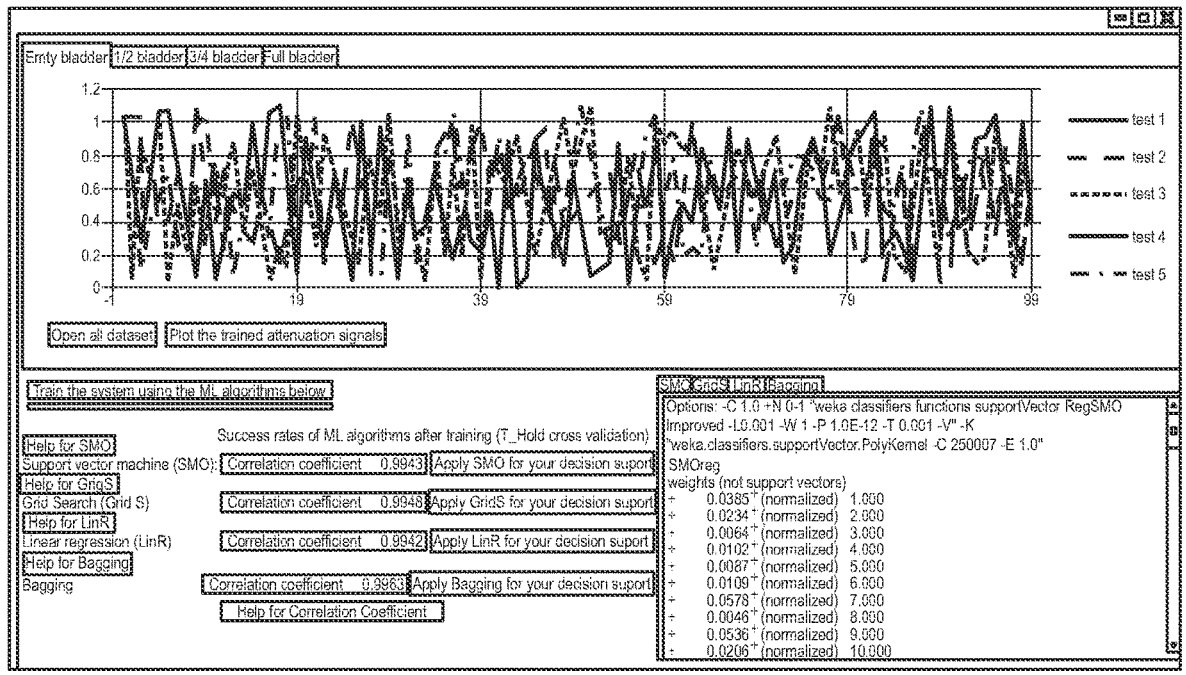
FIG. 29 is a screen shot showing training of the system based on the instances acquired: 5 instances from each state of the bladder in the data set are plotted in the graph at the top of the screen in the specified tab control to observe the patterns of the states. Clicking the button, "Train the system using the ML algorithms below" starts the training process regarding four ML algorithms displayed at the bottom left of the screen in which the success rates of the techniques are displayed in the specified text boxes. Training for each technique starts at the same time in a parallel processing programming to reduce the processing time significantly. The detailed statistical results of the techniques are shown at the bottom right of the screen in the dedicated tab controls. Information about the techniques can be reached by clicking the dedicated help buttons.
Figure 30:
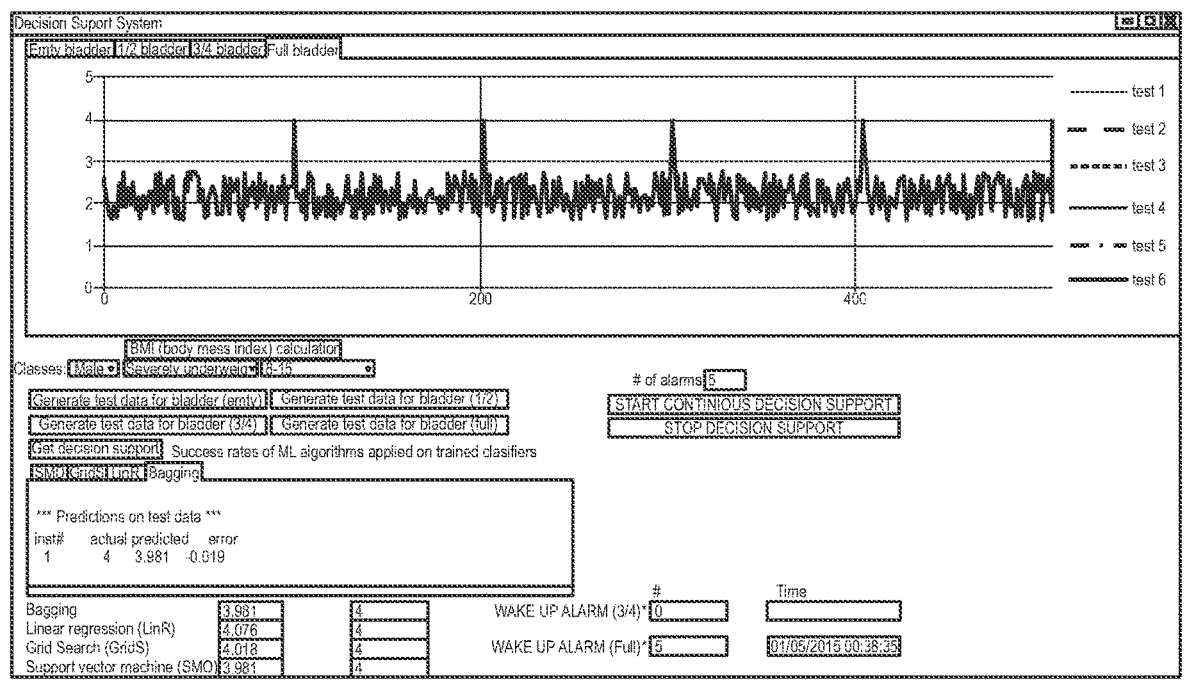
FIG. 30 is a screen shot showing a test of the system for deciding on the state of the bladder in terms of the instance obtained: a voting scheme based on the classification results of the employed techniques mentioned above is performed to decide on the present state of the bladder; majority of the decisions is applied. For the states of empty and ½ no alarm is triggered. On the other hand, an alarm is triggered for the states of ¾ and full states along with a speech (text-to-speech) warning, but, stronger for the full state.

The screen in FIG. 29 is displayed when the function, "Test the system" is called under the menu "Decision Support and Testing". The system can be fed with new generated instances mimicking the real environment to test the system to find out the present state of the bladder throughout the trained classifiers. Testing for each technique starts at the same time in a parallel processing programming to reduce the testing time significantly. The test results of the techniques are displayed in the dedicated tab controls and text boxes. A voting scheme based on the classification results of the employed techniques mentioned above is performed to decide on the present state of the bladder; majority of the decisions is applied. For the states of empty and ½ no alarm is triggered. On the other hand, an alarm is triggered for the states of ¾ and full states along with a speech (text-to-speech) warning[5], but, stronger for the full state. The desired number of alarms can be customized using the dedicated text box, "# of alarms". A log file at the background stores all the real-time information acquired from the people suffering from the nocturnal enuresis and the alarm information triggered by the system for further analysis to ensure the system works as desired.

The main screen of the user is as simple as possible. This screen just harbours the information at the bottom right of FIG. 29 related to the alarms and starting/stopping the system.

We intend to obtain the states of/measurement of the urine in the bladder using a single-element transducer by acquiring attenuation signals from the posterior and anterior walls of the bladder, and 2nd and 3rd harmonics acquired from the urine in the bladder. This data set can be acquired by employing several US signals propagated onto/into the bladder.

The system can evaluate the data set using 3 cross-validation techniques, namely Holdout cross-validation (50/50), k-fold cross-validation and leave-one-out cross-validation (LOOCV) schemes.

From initial clinical measurements it became clear that patient variability played an important role on the volume estimation.[5] The data set should include all classifiers to result in a correct decision with a higher probability when the system obtain a new instance to compare its features to the features of the classifiers trained previously.

Figure 31:
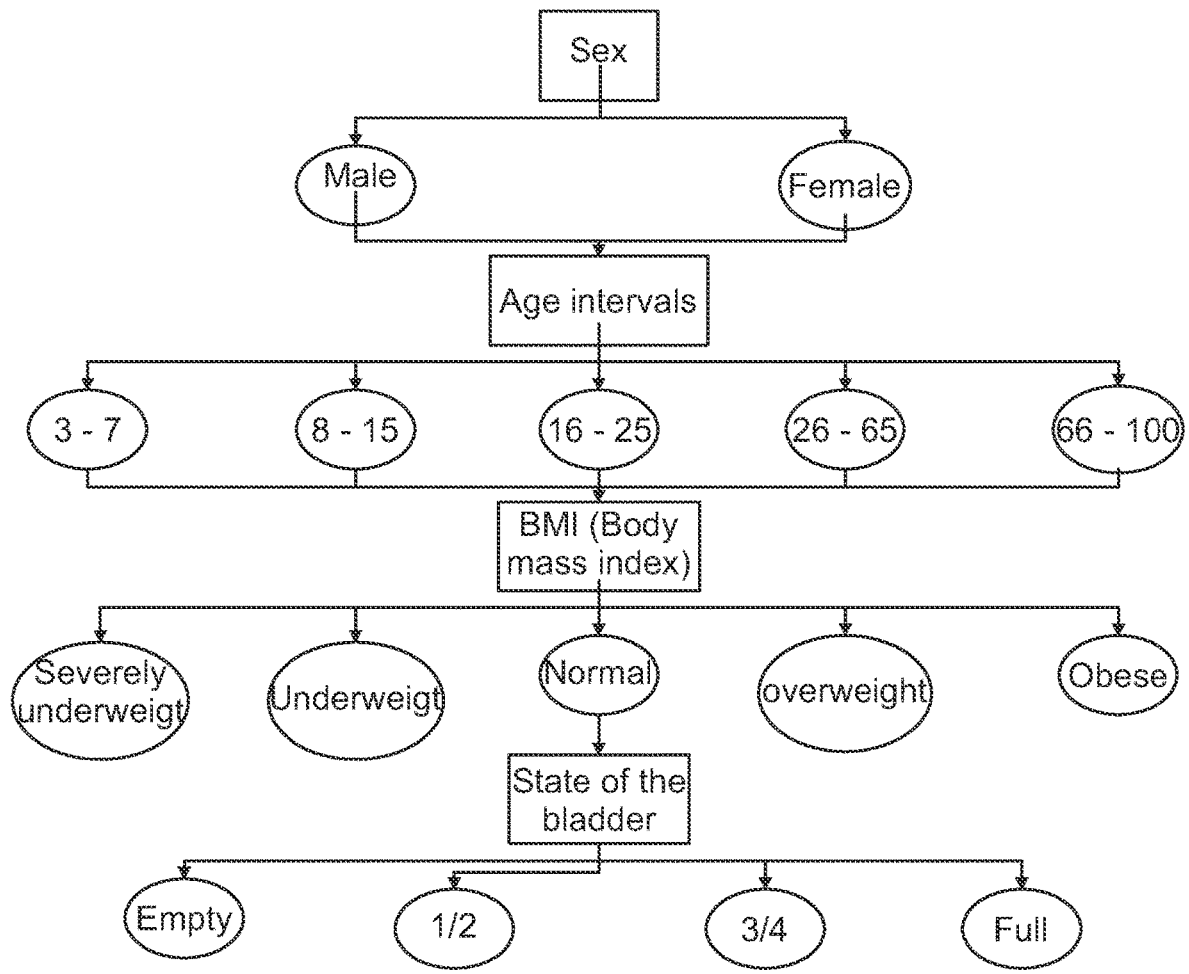
FIG. 31 is a flow chart showing the number of the classes for the general dataset: total number of classes is 200 ($2 \times 5 \times 5 \times 4 = 200$).

There should be 2 classes for males and females, 5 classes for age intervals, 5 classes for body mass index (BMI) and 4 classes for the states of the bladder regarding the different shapes and the positions of the bladder because the attenuation signals reflecting from these organs in terms of the sex, age, BMI (NB. the attenuation loss in Table 4 regarding the fat in the body) and states of the bladder are different from each other. In this respect, for the general use of the application, the system should be trained with the data set that consists of 200 classes (2*5*5*4=200) (FIG. 31). This data can be collected from patients in hospitals suffering the disease and the students who harbour the features of the classes displayed in FIG. 31.

Figure 32:
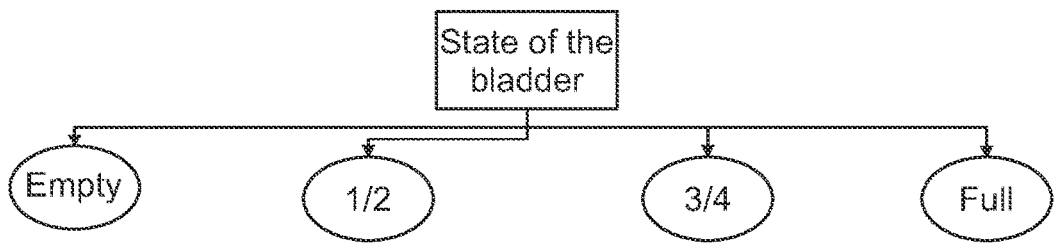
FIG. 32 is a flow chart showing the number of the classes for the customized dataset.

The system can be customized specific to any person and can be ready-to-be-used. First, the system acquires instances for each state of the bladder from a person for several times to obtain a decent data set. Then this data set is trained using the same ML techniques mentioned above for constructing four classifiers (FIG. 32). The dataset used for training is not large, thus we perform a cross-validation of the entire dataset using a leave-one-out scheme and we determined the average performance level[25]. The leave-one-out scheme was used to train the training set and to test the system to determine its accuracy. Leave-one-out cross-validation was simply an n-fold cross-validation, where n is the number of instances in the dataset[27]. Each instance was omitted in turn and the learning scheme was trained with all the remaining instances. We determined the correctness based on the remaining instances, i.e., one for success and zero for failure. The results of all n judgments, i.e., one for each member of the dataset, were averaged and this average represented the final error estimate. This scheme is attractive for two reasons. First, the greatest possible amount of data is used for training in each case, which presumably increases the likelihood that a classifier is accurate. Second, the procedure is deterministic, i.e., random sampling is not involved[27]. Therefore, the accuracy estimate obtained using the leave-one-out scheme is known to be virtually unbiased[28].

Finally, the system is tested using the blind evaluation method in terms of real-time instances acquired from the same person to make sure that it works as desired. MyPad application can be used after successful results obtained from the blind evaluation method. The system has been developed to obtain sex, age and BMI data to feed the general data sets mentioned above even though this information is not needed for the customised use of the application.

System implementation was tested on artificially generated data sets to explore the performance of the ML algorithms employed. 10 data sets (10*400=4000) were generated and the mean accuracy rate of the ML algorithms was measured using 10-fold cross-validation. The accuracy of the system is about 98% with a sensitivity value of 0.98 and a specificity value of 0.99 in terms of training the data set and constructing the classifiers using 400 instances for general data set generated artificially by the system, 100 for each state of the bladder (empty, ½, ¾, and full). A parallel processing algorithm is run to reduce the computation time (training/testing time) significantly for constructing the classifiers for each of the four ML algorithms and testing them. Thus, the required time to establish the classifier for each data set (# of instances=400) ranges from 45 sec to 110 sec. More importantly, this parallel processing scheme is exploited to specify the state of the bladder as new instances come to the system. The required time to specify the state of the bladder for an instance ranges from 20 sec to 40 sec in terms of the four ML techniques, which results in speech and sound alarms together for the ¾ and full states of the bladder.

The system is efficient and effective for predicting the state of the bladder based on the generated artificial data set and the algorithms used. As the skilled person will appreciate, such a model may be readily extrapolated to real-world examples.

Likewise, FIGS. 35-37 show our application developed in Java programming language. This application was mainly built to work on Android systems since 79% of devises currently run on Android system on the market. We aim to employ the application developed in C # for the rest of the market, namely 21%.

FIG. 35 shows the screen shots of the smartphone application showing customizing of the system based on personal features: the personal settings are defined before bladder urine assessment. The application performs its bladder urine assessment using these attributes. (a) is a screen shot of the screen for adjusting alarm options (i.e., the number of the alarm count, speech alarm (text-to-speech), and alarm sound). (b) is a screen shot of the screen for calculating BMI: people are categorized as severely underweight, underweight, normal, overweight and obese based on the height and weight. The person is found to be normal in this example with a value of 23.93. BMI is measured using the formula built by the University of Oxford, BMI=1.3*weight (kg)/height (m)$^{2.5}$=5734*weight (lb)/height (in)$^{2.5}$ (https://people.maths.ox.ac.uk/trefethen/bmi.html).

FIG. 36 has the screen shots of the smartphone application showing training of the system based on the instances acquired either from the general datasets or personal datasets: Clicking the button, "Train the system" starts the training process regarding three ML algorithms displayed at the right screen (b) in which the success rates of the techniques are displayed in the specified sections. Training for each technique starts at the same time in a parallel processing programming to reduce the processing time significantly. (b) The detailed statistical results of the techniques are shown in the dedicated tab control "Results". Information about the techniques can be reached by clicking the dedicated "help" tab.

FIG. 37 has the screen shots of the smartphone application showing a test of the system for deciding on the state of the bladder in terms of the instance obtained from either general datasets or personal datasets: (a) the application checks if the belt is positioned correctly based on the attenuation signal acquired from the bladder. The echoed pulse obtained from the anterior wall is taken as a reference point for correct belt position. (b) a voting scheme based on the classification results of the employed techniques mentioned above is performed using the button "start bladder assessment" to decide on the current state of the bladder; majority of the decisions is applied. For the states of empty and ½ no alarm is triggered. On the other hand, an alarm is triggered for the states of ¾ and full states along with a speech (text-to-speech) warning, but, stronger for the full state.

Figure 38:
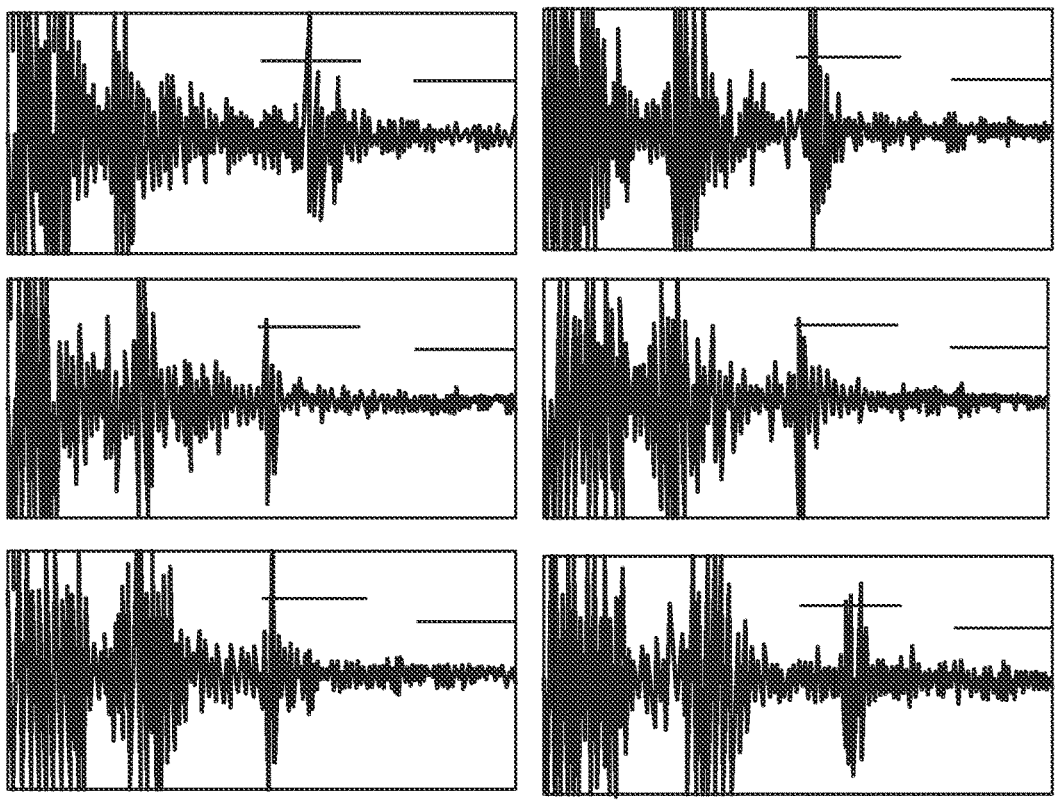
FIG. 38 shows the attenuation signals acquired from the empty bladder of a 6 years old volunteer in 20 minutes intervals: no attenuation signal from the posterior wall (i.e., no signal at the second purple gate) and an attenuation signal from the anterior wall (i.e., a signal at the first green gate).
Figure 39:
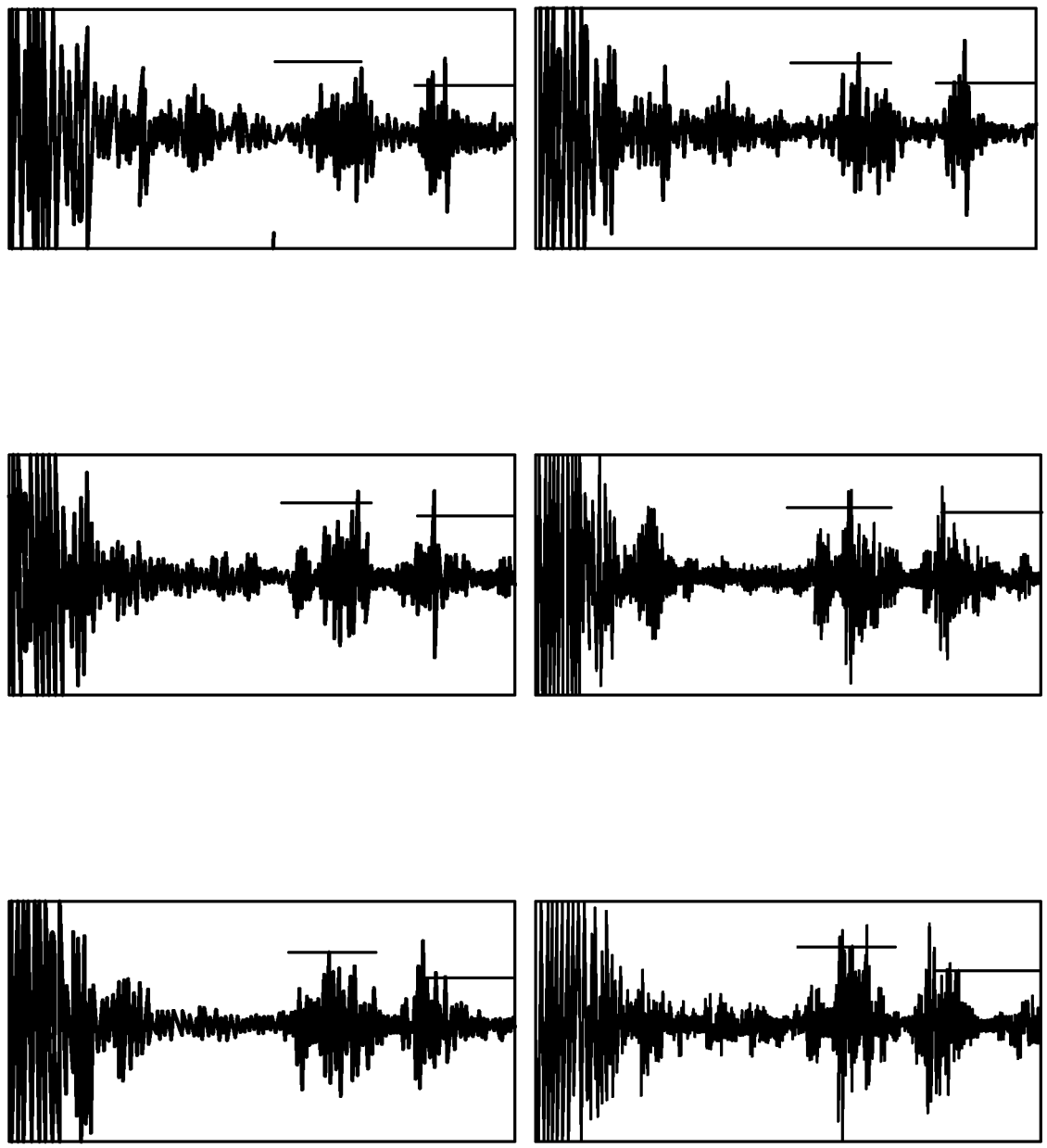
FIG. 39 shows the attenuation signals acquired from the ½ full bladder of a 6 years of volunteer expanding in 20 minutes intervals (read from left to right): an attenuation signal from the posterior wall (i.e., a signal at the second purple gate) and an attenuation signal from the anterior wall (i.e., a signal at the first green gate).
Figure 40:
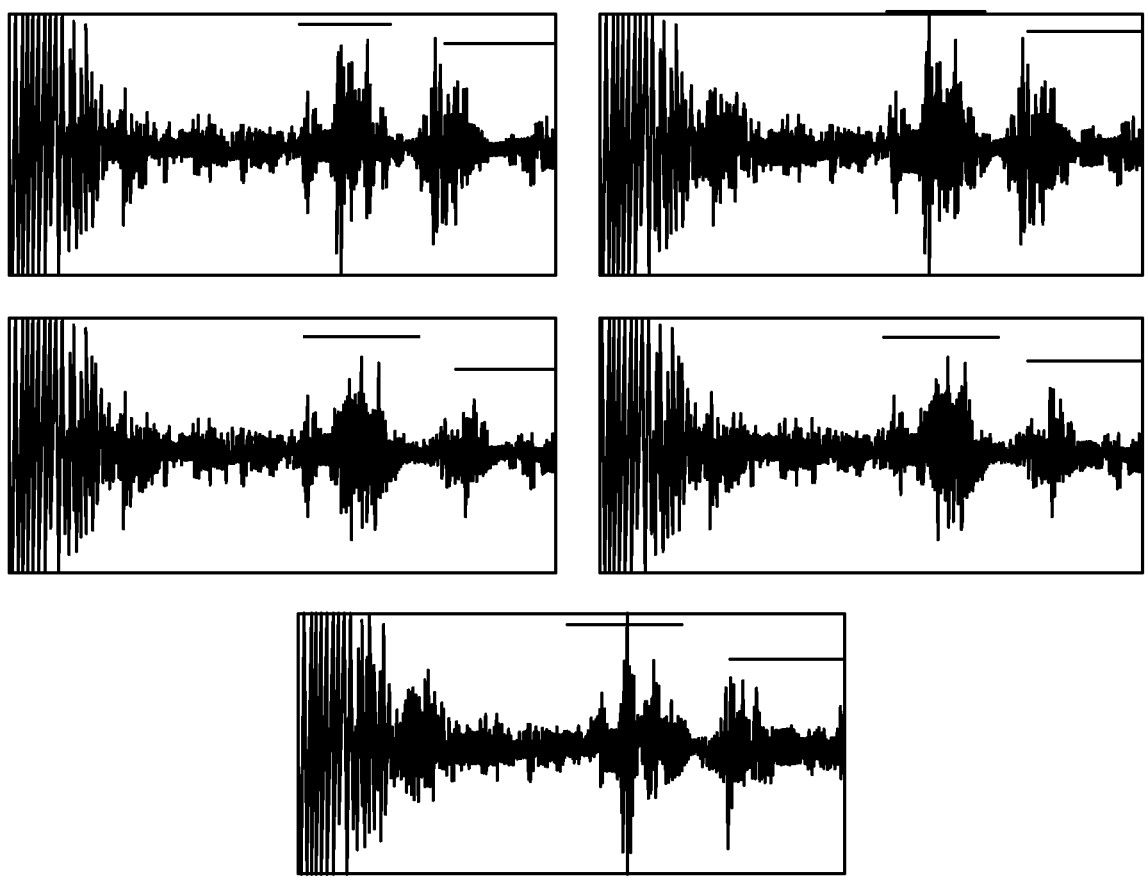
FIG. 40 shows the attenuation signals acquired from the ¾ full bladder of a 6 years of volunteer expanding in 20 minutes intervals: an attenuation signal from the posterior wall (i.e., a signal at the second purple gate) and an attenuation signal from the anterior wall (i.e., a signal at the first green gate).
Figure 41:
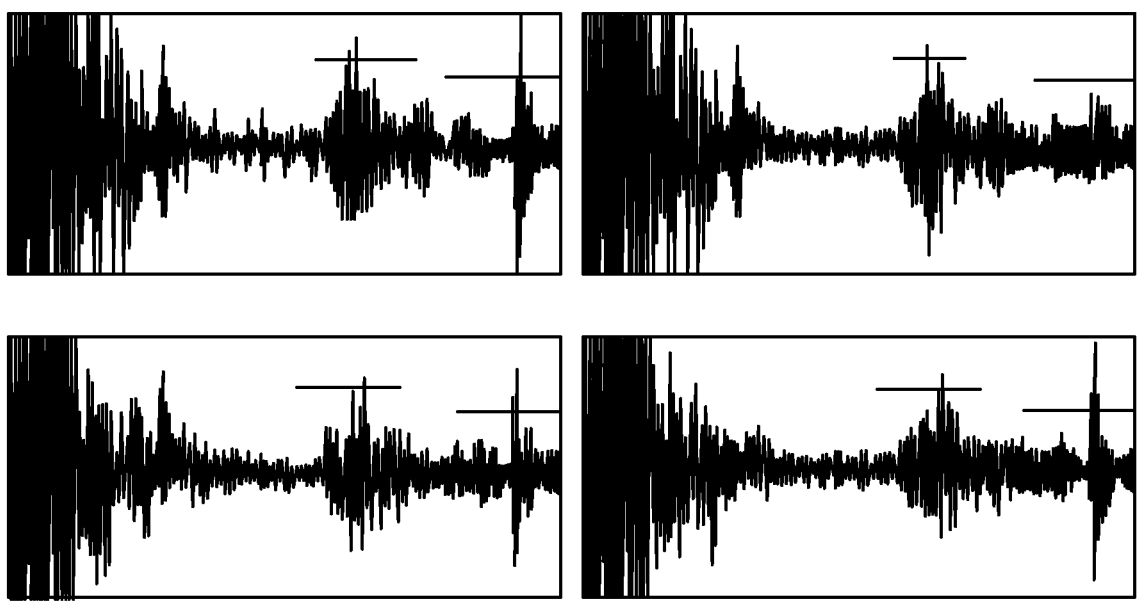
FIG. 41 shows the attenuation signals acquired from the full bladder of a 6 years of volunteer expanding/expanded considerably in 20 minutes intervals: an attenuation signal from the posterior wall (i.e., a signal at the second purple gate) and an attenuation signal from the anterior wall (i.e., a signal at the first green gate).

FIG. 38-41 shows the attenuation signals acquired from the bladder of a 6 years of volunteer in 20 minutes intervals. The distance between the bladder walls increases as the bladder expands based on the increasing volume of the urine within the bladder. FIG. 38 shows the attenuation signals acquired from the empty bladder: no attenuation signal from the posterior wall (i.e., no signal at the second purple gate) and an attenuation signal from the anterior wall (i.e., a signal at the first green gate). FIG. 39 shows the attenuation signals acquired from the % full bladder: an attenuation signal from the posterior wall (i.e., a signal at the second purple gate) and an attenuation signal from the anterior wall (i.e., a signal at the first green gate). FIG. 40 shows the attenuation signals acquired from the ¾ full bladder: an attenuation signal from the posterior wall (i.e., a signal at the second purple gate) and an attenuation signal from the anterior wall (i.e., a signal at the first green gate). FIG. 41 shows the attenuation signals acquired from the full bladder: an attenuation signal from the posterior wall (i.e., a signal at the second purple gate) and an attenuation signal from the anterior wall (i.e., a signal at the first green gate).

REFERENCES

[1] Forsythe, W., Butler, R.: 50 years of enuretic alarms; a review of the literature. Arch Dis Child 64 (1991) 879-885.

[2] Ramakrishnan, K.: Evaluation and treatment of enuresis. Am Fam Physician 78(04) (2008) 489-496.

[3] Austin, P. F., Bauer, S. B., Bower, W., Chase, J., Franco, I., Hoebeke, P., Rittig, S., Walle, J. V., von Gontard, A., Wright, A., Yang, S. S., Nevus, T.: The standardization of terminology of lower urinary tract function in children and adolescents: Update report from the standardization committee of the international children's continence society. The Journal of Urology 191(6) (2014) 1863-1865.

[4] Kiddoo, D.: Nocturnal enuresis: non-pharmacological treatments. BMJ Clinical Evidence 01(305) (2015).

[5] Merks, E. J. W.: Instantaneous Ultrasonic Assessment of Urinary Bladder Volume. PhD thesis, Erasmus University Rotterdam, Optima Grafische Communicatie, Rotterdam, the Netherlands (6 2009).

[6] Tole, N. M., Ostensen, H.: *Basic Physics of ultrasonographic imaging*. World Health Organization, 2005 (http://apps.who.int/iris/bitstream/10665/43179/1/9241592990_eng.pdf).

[7] Knapika, P., Rychlikb, W., Dudab, D., Golysznyb, R., Borowika, Cieślaa, D.: Relationship between blood, nasopharyngeal and urinary bladder temperature during intravascular cooling for therapeutic hypothermia after cardiac arrest. Resuscitation, 83(2), 2012.

[8] Pasha, M.: Business development and commercialization of urosense. Master Thesis, Case Western Reserve University, 2013.

[9] Platt, J. C.: Sequential minimal optimization: A fast algorithm for training support vector machines. Technical Report MSR-TR-98-14, Apr. 21, 1998.

[10] Otto, C.: Principles of echocardiographic image acquisition and doppler analysis. In Saunders, W., ed.: Textbook of Clinical Ecocardiography Philadelphia, PA (2000).

[11] Nelson, T. R., Elvins, T. T.: Visualization of 3d ultrasound data. computer graphics and applications. IEEE 13(6) (1993) 50-57.

[12] Humphrey, V. F.: Nonlinear propagation in ultrasonic fields: measurements, modelling and harmonic imaging. Ultrasonics 38(8) (2000) 267-272.

[13] Asmus, J.: Using the non-linear effect of ultrasound to perform a temperature measurement in water. TU Delft, Delft University of Technology Accessed: 2015-05-06.

[14] Bojorno, L.: Introduction to nonlinear acoustics. Physics Procedia 3(1) (2010) 5-16.

[15] Dongen, K. W. V.: A feasibility study for non-invasive thermometry using non-linear ultrasound. International Journal of Hyperthermia 27(6) (2011) 612-624.

[16] Dongen, K. W. V.: Effect of bubble shell nonlinearity on ultrasound nonlinear propagation through microbubble populations. The Journal of the Acoustical Society of America 129(3) (2011) 76-82.

[17] Rigby, D., Housami, F.: Using bladder ultrasound to detect urinary retention in patients. Journal of Urology 105(21) (2009).

[18] Chan, V., Perlas, A.: *Basics of ultrasound imaging*. In Narouze, S. N., ed.: Atlas of Ultrasound-Guided Procedures in Interventional Pain Management. Springer (2011).

[19] Jennings, D., A Flint, BCH Turton, L. N.: Introduction of medical electronics applications. Hodder Headline PLC (1995).

[20] Hou, Y.: Characterization of a broadband all-optical ultrasound transducer—from optical and acoustical properties to imaging. Ultrasonics, Ferroelectrics, and Frequency Control, IEEE Transactions on 55(8) (2008) 1867-1877.

[21] Platt, J. C.: Sequential minimal optimization: A fast algorithm for training support vector machines. Technical Report MSR-TR-98-14, Microsoft, Microsoft, USA (April 1998).

[22] Bozdogan, H.: Akaike's information criterion and recent developments in information complexity. Journal of Mathematical Psychology 44.

[23] Snipes, M., Taylor, D. C.: Model selection and akaike information criteria: An example from wine ratings and prices. Wine Economics and Policy 3(1) (2014) 3-9.
[24] Russell, S., Norvig, P.: Artificial intelligence, a modern approach. Pearson (2010).
[25] Kuru, K., Niranjan, M., Tunca, Y., Osvank, E., Azim, T.: Biomedical visual data analysis to build an intelligent diagnostic decision support system in medical genetics. Artif Intell Med 62.
[26] Trefethen, N.: Bmi (body mass index). http://people.maths.ox.ac.uk/trefethen/bmi.html Accessed: 2015-05-04.
[27] Witten, I. H., Frank, E., Hall, M. A.: Data mining: practical machine learning tools and techniques. 3rd edition edn. Elsevier, Berlington, USA (2011).
[28] Efron, B.: Estimating the error rate of a prediction rule: improvement on cross-validation. Journal of the American Statistical Association 78(316) (1984) 316-331.

The invention claimed is:

1. A computer-implemented method of estimating a bladder status of a subject, via a computer system comprising:
   a data-processor;
   a bladder monitor configured to acquire real-time bladder data from a bladder;
   a bladder-related event data collection facility configured to manually or automatically collect bladder-related event data for the data-processor; and
   data storage for storing time-stamped real-time bladder data, time-stamped bladder-related event data, and status-mapping data;
   wherein the data-processor is in wired or wireless communication with the bladder monitor, the bladder-related event data collection facility, and the data storage;
   wherein the method comprises:
   (i) the data-processor receiving status-mapping data from the data storage;
   (ii) the data-processor receiving real-time bladder data from the bladder monitor;
   (iii) the data-processor generating, through operating upon the real-time bladder data or part(s) thereof with the status-mapping data, a real-time bladder status indicative of a likelihood of imminent voiding;
   (iv) the data-processor determining whether the bladder status satisfies one or more predetermined pre-void trigger criteria, and:
   a. if so, triggering a pre-void alert event producing a unique output signal to enable action to be taken prior to voiding; or
   b. if not, repeating steps (ii) to (iv);
   wherein the method further comprises refining the status-mapping data, via the computer system;
   wherein the status-mapping data comprises generic status-mapping data tailored to a particular person's attributes;
   wherein the computer system manually or automatically collects data on the timing of voiding events;
   wherein, on the basis the collected data on the timing of voiding events, the computer system gradually adjusts the timing of the pre-void alert towards a time which better correlates with a likely urge to void;
   wherein generating the real-time bladder status comprises the data-processor correlating the real-time bladder data with a bladder status through operating upon the bladder data or part thereof with the status-mapping data which, after refining the status-mapping data via machine learning, includes operating upon the bladder data with one or more classifier(s) trained during the machine learning such that, where one classifier is used, said classifier predicts the bladder status directly from the bladder data fed thereto, and, where two or more classifiers are involved, each classifier produces a distinct bladder status opinion, and the opinions are aggregated to generate the bladder status.

2. A pre-void alert system, wherein the pre-void alert system is a computer system comprising:
   a data-processor;
   a bladder monitor operable to acquire real-time bladder data from a bladder of a subject;
   a bladder-related event data collection facility configured to manually or automatically collect bladder-related event data for the data-processor; and
   data storage for storing time-stamped real-time bladder data, time-stamped bladder-related event data, and status-mapping data;
   wherein the data-processor is in wired or wireless communication with the bladder monitor, the bladder-related event data collection facility, and the data storage;
   wherein:
   the data-processor is operable:
   i) to receive status-mapping data from the data storage;
   ii) to receive real-time bladder data from the bladder monitor;
   iii) to generate a real-time bladder status, through operating upon the real-time bladder data or part(s) thereof with the status-mapping data;
   iv) to determine whether the bladder status satisfies one or more predetermined pre-void trigger criteria, and:
   a. if so, triggering a pre-void alert event producing a unique output signal to enable action to be taken prior to voiding; or
   b. if not, repeating steps (ii) to (iv);
   wherein:
   the computer system is further operable to refine the status-mapping data;
   the status-mapping data comprises generic status-mapping data tailored to a particular person's attributes;
   wherein the computer system is configured to manually or automatically collect data on the timing of voiding events;
   wherein, on the basis the collected data on the timing of voiding events, the computer system is configured to gradually adjust the timing of the pre-void alert towards a time which better correlates with a likely urge to void;
   wherein the data-processor generates the real-time bladder status by correlation of the real-time bladder data with a bladder status through operating upon the bladder data or part thereof with the status-mapping data which, after refining the status-mapping data via machine learning, includes operating upon the bladder data with one or more classifier(s) trained during the machine learning such that, where one classifier is used, said classifier predicts the bladder status directly from the bladder data fed thereto, and, where two or more classifiers are involved, each classifier produces a distinct bladder status opinion, and the opinions are aggregated to generate the bladder status.

3. The method of claim 1, wherein the real-time bladder data is raw or processed data derived from real-time echoed attenuation signals from the bladder detected or recorded via ultrasound transducers.

4. The method of claim 1, wherein the bladder-related event data comprises one or more items of data selected from the group consisting of a timing of food consumption, a timing of drink consumption, an extent of food consumption, an extent of drink consumption, a timing of a bladder voiding event, a volume of a bladder voiding event, a timing of an urge to urinate, and combinations thereof.

5. The method of claim 1, wherein the bladder monitor comprises part or all of the bladder-related event data collection facility, or a remote device that is remote from the bladder monitor and configured to communicate, in a wired or wireless fashion, with the data processor comprises part or all of the bladder-related event data collection facility.

6. The method of claim 1, wherein refining the status-mapping data, via the computer system, is implemented by:
  v) the data-processor receiving real-time bladder data from the bladder monitor;
  vi) storing the real-time bladder data in the data storage with an associated time-stamp indicative of when the data was obtained;
  vii) the data-processor receiving bladder-related event data from the bladder monitor itself or the remote device;
  viii) storing the bladder-related event data in the data storage with an associated time-stamp indicative of when the data was obtained;
  ix) identifying any relationships between time-stamped real-time bladder data and time-stamped bladder-related event data; and, where a relationship is identified, on the basis of said relationship correlating the real-time bladder data with a bladder status; and
  x) refining the status-mapping data based on any correlations between bladder data and bladder status.

7. The method of claim 1, wherein the particular person's attributes include at least the person's age, gender, and body-mass index (BMI).

8. The method of claim 7, wherein BMI is calculable via the equation:

$$BMI = 1.3 \times \frac{\text{weight (kg)}}{\text{height (m)}^{2.5}}.$$

9. The method of claim 1, wherein the status-mapping data comprises refined or customized status-mapping data derived through machine learning, and the status-mapping data is particular to the particular person and encodes a person-specific predictive model by which mapping of real-time bladder data to a bladder status is facilitated.

10. The method of claim 1, wherein generating the real-time bladder status comprises the data-processor correlating the real-time bladder data with a bladder status through operating upon the bladder data or part thereof with the status-mapping data.

11. The method of claim 3, wherein each of the ultrasound transducers is configured to transmit ultrasound waves and to detect echoed attenuation signals from the bladder.

12. The method of claim 3, wherein each of the ultrasound transducers is non-imaging.

13. The method of claim 3, wherein each of the ultrasound transducers is configured to transmit pulsed ultrasound waves of a frequency between 2 MHz and 5 MHz with a pulse width between 50 ns and 5 µs at a pulse repetition frequency (PRF) between 10 Hz and 2 KHz where the power of each ultrasound pulse or the total power used by all transducers is between 0.01 W/cm$^2$ and 3 W/cm$^2$, and to detect attenuation signals echoed at a range of between 1 cm and 20 cm from the transducer.

14. The method of claim 1, wherein refining status-mapping data based on any correlations between bladder data and bladder status comprises:
  i) generating training sets from the correlated bladder data and bladder status;
  ii) generating and training one or more bladder status classifiers with the training sets; and
  iii) incorporating the one or more trained classifiers as status-mapping data.

15. The method of claim 1, wherein the bladder data comprises echoed ultrasound attenuation signals and echoed ultrasound harmonic signals, and the status-mapping data comprises one or more classifiers that generate bladder statuses utilising both the echoed ultrasound attenuation signals and the echoed ultrasound harmonic signals, or respective information derived therefrom.

16. The method of claim 1, wherein two or more echoed attenuation signals corresponding to two or more reflecting interfaces associated with a bladder are used to determine a bladder status.

17. The method of claim 1, wherein receiving real-time bladder data from the bladder monitor comprises acquiring bladder data from two or more ultrasound transducers associated with the bladder monitor.

18. The method of claim 1, wherein the bladder monitor is worn by a patient, outside of the patient's body, and configured to acquire real-time bladder data from the bladder of the patient, and a pre-void alert event is triggered before the patient is likely to void.

19. The method of claim 6, further comprising repeating (v) to (x) to further refine the status-mapping data to increase the accuracy of correlations between bladder data and bladder status.

20. The method of claim 1, wherein the method further comprises the computer system training itself, using voiding events, to specify a new alarm threshold value customised or tuned to the particular person's bladder liquid volume trigger point, which stretches the threshold value to the point of voiding.

21. The method of claim 1, wherein the status mapping data comprises a support vector machine (SVM) classifier produced by sequential minimal optimization (SMO), a grid search classifier, a linear regression classifier and an ensemble bagging classifier.

22. The method of claim 1, wherein the event data collection facility comprises a user-interface such that the bladder event data is collected through manual input via the user-interface.

23. The method of claim 1, wherein the bladder monitor comprises one or more event buttons or triggers which are operable to record the timing of one or more specific events.

24. The method of claim 1, wherein the bladder-related event data comprises a timing of a bladder voiding event, wherein said bladder voiding event is voluntary.

25. The method of claim 1, wherein the one or more classifiers comprise a support vector machine (SVM) classifier.

26. The method of claim 25, wherein the support vector machine (SVM) classifier is trained using sequential minimal optimization (SMO).

27. The method of claim 1, wherein the one or more classifiers is two or more classifiers, wherein the opinions are aggregated by average or majority voting.

28. The method of claim 27, wherein the average or majority voting is by a weighted average or weighted majority of the opinions.

29. The method of claim 27, wherein the two or more classifiers comprise two or more of or all of an (SVM) classifier produced by sequential minimal optimization (SMO), Grid Search classifier, Linear Regression classifier and ensemble bagging classifier.

30. A non-transitory computer-readable recording medium comprising software code executable to cause a computer to perform a computer-implemented method of estimating a bladder status of a subject when the software code is executed on a computer comprising:
- a data-processor;
- a bladder monitor configured to acquire real-time bladder data from a bladder;
- a bladder-related event data collection facility configured to manually or automatically collect bladder-related event data for the data-processor; and
- data storage for storing time-stamped real-time bladder data, time-stamped bladder-related event data, and status-mapping data;

wherein the data-processor is in wired or wireless communication with the bladder monitor, the bladder-related event data collection facility, and the data storage;

wherein the method comprises:
(i) the data-processor receiving status-mapping data from the data storage;
(ii) the data-processor receiving real-time bladder data from the bladder monitor;
(iii) the data-processor generating, through operating upon the real-time bladder data or part(s) thereof with the status-mapping data, a real-time bladder status indicative of a likelihood of imminent voiding;
(iv) the data-processor determining whether the bladder status satisfies one or more predetermined pre-void trigger criteria, and:
  a. if so, triggering a pre-void alert event producing a unique output signal to enable action to be taken prior to voiding; or
  b. if not, repeating steps (ii) to (iv);

wherein the method further comprises refining the status-mapping data, via the computer system;

wherein the status-mapping data comprises generic status-mapping data tailored to a particular person's attributes;

wherein the computer system manually or automatically collects data on the timing of voiding events;

wherein, on the basis the collected data on the timing of voiding events, the computer system gradually adjusts the timing of the pre-void alert towards a time which better correlates with a likely urge to void;

wherein generating the real-time bladder status comprises the data-processor correlating the real-time bladder data with a bladder status through operating upon the bladder data or part thereof with the status-mapping data which, after refining the status-mapping data via machine learning, includes operating upon the bladder data with one or more classifier(s) trained during the machine learning such that, where one classifier is used, said classifier predicts the bladder status directly from the bladder data fed thereto, and, where two or more classifiers are involved, each classifier produces a distinct bladder status opinion, and the opinions are aggregated to generate the bladder status.

* * * * *